US010150797B2

(12) United States Patent
Kramps et al.

(10) Patent No.: US 10,150,797 B2
(45) **Date of Patent: *Dec. 11, 2018**

(54) RESPIRATORY SYNCYTIAL VIRUS (RSV) VACCINE

(71) Applicant: CureVac AG, Tübingen (DE)

(72) Inventors: Thomas Kramps, Tübingen (DE); Margit Schnee, Konstanz (DE); Daniel Voss, Tübingen (DE); Benjamin Petsch, Tübingen (DE)

(73) Assignee: CureVac AG, Tübingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/488,815

(22) Filed: Apr. 17, 2017

(65) Prior Publication Data

US 2017/0218030 A1 Aug. 3, 2017

Related U.S. Application Data

(63) Continuation of application No. 15/048,439, filed on Feb. 19, 2016, now Pat. No. 9,688,729, which is a
(Continued)

(51) Int. Cl.
*A61K 39/215* (2006.01)
*C07K 14/005* (2006.01)
(Continued)

(52) U.S. Cl.
CPC ............ *C07K 14/005* (2013.01); *A61K 39/12* (2013.01); *A61K 39/155* (2013.01);
(Continued)

(58) Field of Classification Search
None
See application file for complete search history.

(56) References Cited

U.S. PATENT DOCUMENTS 9,688,729 B2 6/2017 Kramps et al.
2005/0032730 A1 2/2005 Von der Mulbe et al.
(Continued)

FOREIGN PATENT DOCUMENTS

RU 2407749 C2 12/2007
WO WO 2005-039501 5/2005
(Continued)

OTHER PUBLICATIONS

Bauer et al., "The impact of intragenic CpG content on gene expression," *Nucleic Acids Research*, 38(12):3891-3908, 2010.
(Continued)

*Primary Examiner* — Janet L Andres
*Assistant Examiner* — Stuart W Snyder
(74) *Attorney, Agent, or Firm* — Parker Highlander PLLC

(57) ABSTRACT

The present invention relates to an mRNA sequence, comprising a coding region, encoding at least one antigenic peptide or protein of RSV infections Respiratory syncytial virus (RSV) or a fragment, variant or derivative thereof. Additionally the present invention relates to a composition comprising a plurality of mRNA sequences comprising a coding region, encoding at least one antigenic peptide or protein of RSV infections Respiratory syncytial virus (RSV) or a fragment, variant or derivative thereof. Furthermore it also discloses the use of the mRNA sequence or the composition comprising a plurality of mRNA sequences for the preparation of a pharmaceutical composition, especially a vaccine, e.g. for use in the prophylaxis or treatment of RSV infections Respiratory syncytial virus (RSV) infections. The present invention further describes a method of treatment or prophylaxis of RSV infections using the mRNA sequence.

21 Claims, 23 Drawing Sheets

Specification includes a Sequence Listing.

Related U.S. Application Data continuation of application No. PCT/EP2014/002301, filed on Aug. 21, 2014.

(51) Int. Cl.

| | |
|---|---|
| ***A61K 39/12*** | (2006.01) |
| ***A61K 39/155*** | (2006.01) |
| ***C07K 16/10*** | (2006.01) |
| ***C12N 7/00*** | (2006.01) |
| *A61K 39/00* | (2006.01) |
| *A61K 48/00* | (2006.01) |

(52) U.S. Cl.

CPC ............ *C07K 16/1027* (2013.01); *C12N 7/00* (2013.01); *A61K 48/00* (2013.01); *A61K 2039/505* (2013.01); *A61K 2039/53* (2013.01); *A61K 2039/6031* (2013.01); *C07K 2317/24* (2013.01); *C12N 2760/18534* (2013.01)

(56) References Cited

U.S. PATENT DOCUMENTS

| | | | |
|---|---|---|---|
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0250225 | A1 | 10/2011 | Fotin-Mleczek et al. |
| 2012/0021043 | A1 | 1/2012 | Kramps et al. |
| 2012/0258046 | A1 | 10/2012 | Mutzke |
| 2013/0129754 | A1 | 5/2013 | Thess et al. |
| 2013/0142818 | A1 | 6/2013 | Baumhof et al. |
| 2013/0259879 | A1 | 10/2013 | Baumhof et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0306249 | A1 | 10/2015 | Baumhof et al. |
| 2015/0320847 | A1 | 11/2015 | Thess et al. |
| 2016/0130345 | A1 | 5/2016 | Fotin-Mleczek et al. |
| 2016/0166668 | A1 | 6/2016 | Kallen et al. |
| 2016/0166678 | A1 | 6/2016 | Kallen et al. |
| 2016/0166710 | A1 | 6/2016 | Baumhof |
| 2016/0166711 | A1 | 6/2016 | Schnee et al. |
| 2016/0168207 | A1 | 6/2016 | Kramps et al. |
| 2016/0168227 | A1 | 6/2016 | Kallen et al. |
| 2016/0235864 | A1 | 8/2016 | Schlake et al. |
| 2016/0304883 | A1 | 10/2016 | Grund et al. |
| 2016/0304938 | A1 | 10/2016 | Wochner |
| 2016/0326575 | A1 | 11/2016 | Von der Mulbe et al. |
| 2016/0331844 | A1 | 11/2016 | Fotin-Mleczek et al. |
| 2017/0014496 | A1 | 1/2017 | Fotin-Mleczek et al. |

FOREIGN PATENT DOCUMENTS

| | | |
|---|---|---|
| WO | WO 2006/015789 | 2/2006 |
| WO | WO 2006/050280 | 5/2006 |
| WO | WO 2009/046739 | 4/2009 |
| WO | WO 2012/019630 | 2/2012 |
| WO | WO 2012/037078 | 3/2012 |
| WO | WO 2012/116714 | 9/2012 |
| WO | WO 2012/116715 | 9/2012 |
| WO | WO 2015/101414 | 7/2015 |
| WO | WO 2015/149944 | 10/2015 |

OTHER PUBLICATIONS

Fotin-Mleczek et al., "Highly potent mRNA based cancer vaccines represent an attractive platform for combination therapies supporting an improved therapeutic effect," *The Journal of Gene Medicine*, 14(6):428-439, 2012.

Oomens et al., "The cytoplasmic tail of the human respiratory syncytial virus F protein plays critical roles in cellular localization of the F protein and infectious progeny production," *Journal of Virology*, 80(21):10465-10477, 2006.

PCT International Search Report and Written Opinion issued in International Application No. PCT/EP2014/002301, dated Mar. 6, 2015.

Petsch et al., "Protective efficacy of in vitro synthesized, specific mRNA vaccines against influenza A virus infection," *Nature Biotechnology*, 30(12):1210-1216, 2012.

Schlake et al., "Developing mRNA-vaccine technologies," *RNA Biology*, 9(11):1319-1330, 2012.

Anderson et al., "Strategic priorities for respiratory syncytial virus (RSV) vaccine development," *Vaccine*, 31S:B209-B215, 2013.

Higgins et al., "Advances in RSV vaccine research and development—A global agenda," *Vaccine*, 34(26):2870-2875, 2016.

Jones et al, "Sendai virus-based RSV vaccine protects African green monkeys from RSV infection," *Vaccine*, 30(5):959-968, 2012.

RSV-F long (GC) R1691

GGGAGAAAGCUUACCAUGGAGCUGCCCAUCCUCAAGGCCAACGCCAUCACCACCAUCCUG
GCGGCCGUGACGUUCUGCUUCGCCAGCUCCCAGAACAUCACCGAGGAGUUCUACCAGAGC
ACCUGCUCCGCCGUCAGCAAGGGCUACCUGUCCGCCCUCCGGACCGGGUGGUACACGAGC
GUGAUCACCAUCGAGCUGUCCAACAUCAAGGAGAACAAGUGCAACGGCACCGACGCGAAG
GUGAAGCUGAUCAACCAGGAGCUCGACAAGUACAAGAACGCCGUCACCGAGCUGCAGCUG
CUCAUGCAGAGCACGACCGCCGCCAACAACCGCGCGCGGCGCGAGCUGCCGCGGUUCAUG
AACUACACCCUGAACAACACCAAGAAGACGAACGUGACCCUCUCCAAGAAGCGCAAGCGG
CGCUUCCUGGGGUUCCUGCUCGGCGUGGGGAGCGCCAUCGCCUCCGGCAUCGCCGUCAGC
AAGGUGCUGCACCUGGAGGGCGAGGUGAACAAGAUCAAGUCCGCCCUCCUGAGCACCAAC
AAGGCGGUCGUGUCCCUGAGCAACGGGGUGUCCGUCCUCACCAGCAAGGUGCUGGACCUG
AAGAACUACAUCGACAAGCAGCUCCUGCCCAUCGUGAACAAGCAGUCCUGCCGGAUCAGC
AACAUCGAGACGGUCAUCGAGUUCCAGCAGAAGAACAACCGCCUGCUCGAGAUCACCCGG
GAGUUCAGCGUGAACGCCGGCGUGACCACCCCCGUCUCCACGUACAUGCUGACCAACAGC
GAGCUGCUCUCCCUGAUCAACGACAUGCCCAUCACCAACGACCAGAAGAAGCUGAUGAGC
AACAACGUGCAGAUCGUGCGCCAGCAGUCCUACAGCAUCAUGUCCAUCAUCAAGGAGGAG
GUCCUCGCCUACGUGGUGCAGCUGCCGCUGUACGGGGUCAUCGACACCCCCUGCUGGAAG
CUCCACACGAGCCCCCUGUGCACCACCAACACCAAGGAGGGCUCCAACAUCUGCCUGACG
CGGACCGACCGCGGGUGGUACUGCGACAACGCCGGCAGCGUGUCCUUCUUCCCCCAGGCC
GAGACCUGCAAGGUCCAGAGCAACCGGGUGUUCUGCGACACCAUGAACUCCCUCACGCUG
CCGAGCGAGGUGAACCUGUGCAACGUCGACAUCUUCAACCCCAAGUACGACUGCAAGAUC
AUGACCUCCAAGACCGACGUGAGCUCCAGCGUGAUCACCUCCCUCGGCGCGAUCGUCAGC
UGCUACGGGAAGACGAAGUGCACCGCCAGCAACAAGAACCGCGGCAUCAUCAAGACCUUC
UCCAACGGGUGCGACUACGUGAGCAACAAGGGCGUGGACACCGUCUCCGUGGGCAACACC
CUGUACUACGUGAACAAGCAGGAGGGGAAGAGCCUGUACGUCAAGGGCGAGCCCAUCAUC
AACUUCUACGACCCCCUCGUGUUCCCGUCCGACGAGUUCGACGCCAGCAUCUCCCAGGUG
AACGAGAAGAUCAACCAGAGCCUGGCCUUCAUCCGGAAGUCCGACGAGCUGCUGCACCAC
GUCAACGCCGGGAAGAGCACGACCAACAUCAUGAUCACCACCAUCAUCAUCGUGAUCAUC
GUGAUCCUCCUGUCCCUGAUCGCGGUCGGCCUCCUGCUGUACUGCAAGGCCCGCAGCACG
CCCGUGACCCUCUCCAAGGACCAGCUGAGCGGGAUCAACAACAUCGCCUUCUCCAACUGA
GGACUAGUUAUAAGACUGACUAGCCCGAUGGGCCUCCCAACGGGCCCUCCUCCCCUCCUU
GCACCGAGAUUAAUAAAAAAAAAAAAAAAAAAAAAAAAAAAAAAAAAAAAAAAAAAAAAA
AAAAAAAAAAAAAAAAAAUGCAUCCCCCCCCCCCCCCCCCCCCCCCCCCCCCCCAAAGGC
UCUUUUCAGAGCCACCAGAAUU

Fig. 1

RSV-F long (GC) R2510

GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCAGCACGCCCGUGACCCUCUCCAAGGACC
AGCUGAGCGGGAUCAACAACAUCGCCUUCUCCAACUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCAAAGGCUCUUUUCAGAGCCAC
CAGAAUU

Fig. 2

RSV-Fdel554-574 long (GC) R2821

GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCUGAGGACUAGUGCAUCACAUUUAAAAGC
AUCUCAGCCUACCAUGAGAAUAAGAGAAAGAAAAUGAAGAUCAAUAGCUUAUUCAUCUCU
UUUUCUUUUUCGUUGGUGUAAAGCCAACACCCUGUCUAAAAAACAUAAAUUUCUUUAAUC
AUUUUGCCUCUUUUCUCUGUGCUUCAAUUAAUAAAAAAUGGAAAGAACCUAGAUCUAAAA
AAAAAAAAAAAAAAAAAAAAAAAAAAAAAAAAAAAAAAAAAAAAAAAAAAAAAAAAAAAA
UGCAUCCCCCCCCCCCCCCCCCCCCCCCCCCCCCCCCAAAGGCUCUUUCAGAGCCACCAG
AAUU

Fig. 3

RSV-N (GC) R2831

GGGGCGCUGCCUACGGAGGUGGCAGCCAUCUCCUUCUCGGCAUCAAGCUUACCAUGGCCC
UGAGCAAGGUGAAGCUCAACGACACCCUGAACAAGGACCAGCUGCUCUCCAGCUCCAAGU
ACACCAUCCAGCGCAGCACGGGCGACUCCAUCGACACCCCCAACUACGACGUCCAGAAGC
ACAUCAACAAGCUGUGCGGGAUGCUGCUCAUCACCGAGGACGCCAACCACAAGUUCACCG
GCCUGAUCGGGAUGCUGUACGCGAUGAGCCGGCUCGGCCGCGAGGACACGAUCAAGAUCC
UGCGGGACGCCGGGUACCACGUGAAGGCCAACGGCGUGGACGUCACCACCCACCGCCAGG
ACAUCAACGGCAAGGAGAUGAAGUUCGAGGUGCUGACCCUCGCCUCCCUGACGACCGAGA
UCCAGAUCAACAUCGAGAUCGAGAGCCGGAAGUCCUACAAGAAGAUGCUGAAGGAGAUGG
GGGAGGUGGCCCCGGAGUACCGCCACGACAGCCCCGACUGCGGCAUGAUCAUCCUCUGCA
UCGCGGCCCUGGUCAUCACCAAGCUGGCCGCCGGGGACCGGUCCGGCCUCACCGCGGUGA
UCCGCCGGGCCAACAACGUGCUGAAGAACGAGAUGAAGCGCUACAAGGGGCUGCUCCCCA
AGGACAUCGCCAACAGCUUCUACGAGGUCUUCGAGAAGCACCCCCACUUCAUCGACGUGU
UCGUGCACUUCGGCAUCGCCCAGUCCAGCACGCGGGGCGGGUCCCGCGUCGAGGGCAUCU
UCGCCGGGCUGUUCAUGAACGCGUACGGCGCCGGCCAGGUGAUGCUGCGGUGGGGCGUGC
UCGCCAAGAGCGUCAAGAACAUCAUGCUGGGGCACGCCUCCGUGCAGGCCGAGAUGGAGC
AGGUGGUCGAGGUGUACGAGUACGCGCAGAAGCUGGGCGGCGAGGCCGGGUUCUACCACA
UCCUCAACAACCCGAAGGCCAGCCUGCUGUCCCUCACCCAGUUCCCGCACUUCAGCAGCG
UGGUCCUGGGGAACGCCGCCGGCCUGGGGAUCAUGGGCGAGUACCGCGGGACCCCGCGGA
ACCAGGACCUCUACGACGCGGCCAAGGCCUACGCCGAGCAGCUGAAGGAGAACGGCGUGA
UCAACUACUCCGUGCUGGACCUCACCGCCGAGGAGCUGGAGGCGAUCAAGCACCAGCUGA
ACCCCAAGGACAACGACGUCGAGCUCUGAGGACUAGUGCAUCACAUUUAAAAGCAUCUCA
GCCUACCAUGAGAAUAAGAGAAAGAAAAUGAAGAUCAAUAGCUUAUUCAUCUCUUUUUCU
UUUUCGUUGGUGUAAAGCCAACACCCUGUCUAAAAAACAUAAAUUUCUUUAAUCAUUUUG
CCUCUUUUCUCUGUGCUUCAAUUAAUAAAAAAUGGAAAGAACCUAGAUCUAAAAAAAAAA
AAAAAAAAAAAAAAAAAAAAAAAAAAAAAAAAAAAAAAAAAAAAAAAAAAAAAAUGCAUC
CCCCCCCCCCCCCCCCCCCCCCCCCCCCCCAAAGGCUCUUUUCAGAGCCACCAGAAU

Fig. 4

RSV-M$_{2-1}$ (GC) R2833

GGGGCGCUGCCUACGGAGGUGGCAGCCAUCUCCUUCUCGGCAUCAAGCUUACCAUGAGCC
GCCGGAACCCCUGCAAGUUCGAGAUCCGCGGCCACUGCCUGAACGGGAAGCGGUGCCACU
UCUCCCACAACUACUUCGAGUGGCCGCCCCACGCCCUCCUGGUGCGCCAGAACUUCAUGC
UGAACCGGAUCCUCAAGAGCAUGGACAAGUCCAUCGACACCCUGAGCGAGAUCUCCGGCG
CCGCGGAGCUGGACCGCACCGAGGAGUACGCCCUCGGGGUCGUGGGCGUGCUGGAGAGCU
ACAUCGGGUCCAUCAACAACAUCACGAAGCAGAGCGCCUGCGUCGCCAUGUCCAAGCUGC
UCACCGAGCUGAACAGCGACGACAUCAAGAAGCUGCGGGACAACGAGGAGCUCAACUCCC
CCAAGAUCCGCGUGUACAACACCGUGAUCAGCUACAUCGAGUCCAACCGGAAGAACAACA
AGCAGACCAUCCACCUGCUGAAGCGCCUCCCCGCCGACGUCCUGAAGAAGACGAUCAAGA
ACACCCUGGACAUCCACAAGAGCAUCACCAUCAACAACCCGAAGGAGCUCACCGUGUCCG
ACACGAACGACCACGCGAAGAACAACGACACCACCUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCAAAGGCUCUUUUCAGAGCCAC
CAGAAUU

Fig. 5

A
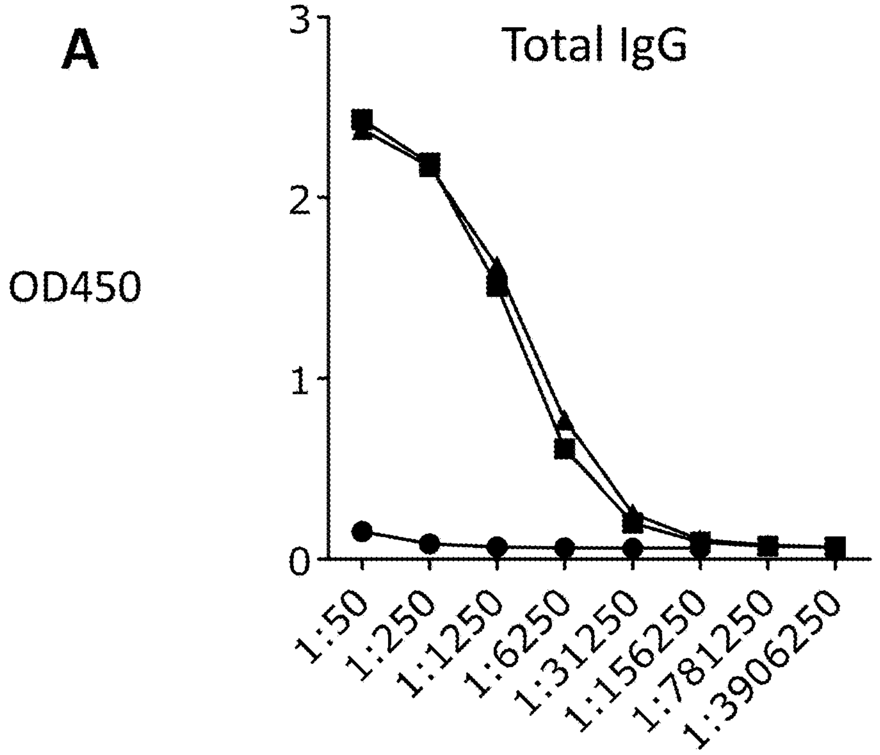
B
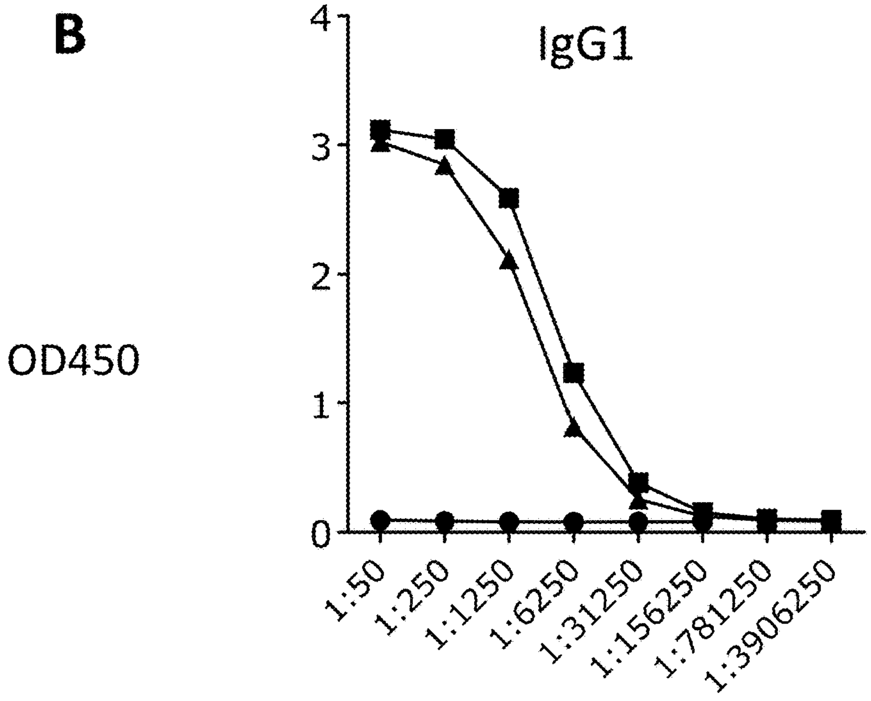
Figs. 6A-B

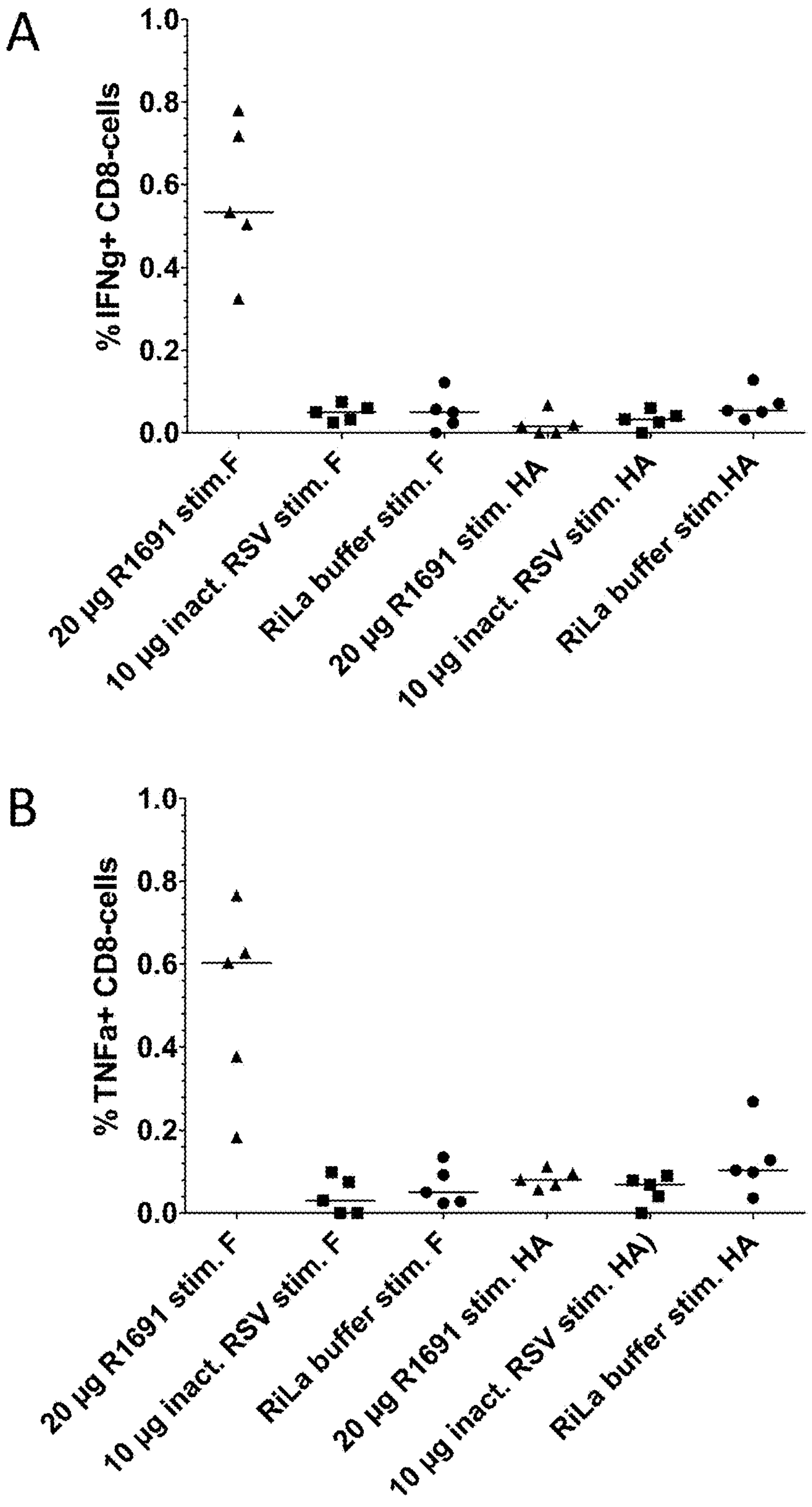
Figs. 8A-B

C
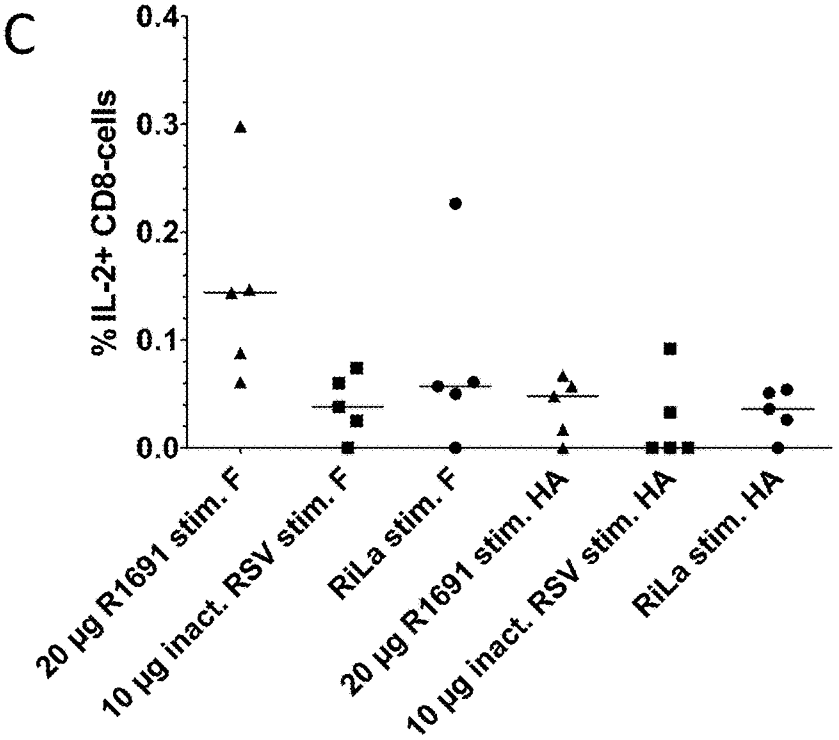
D
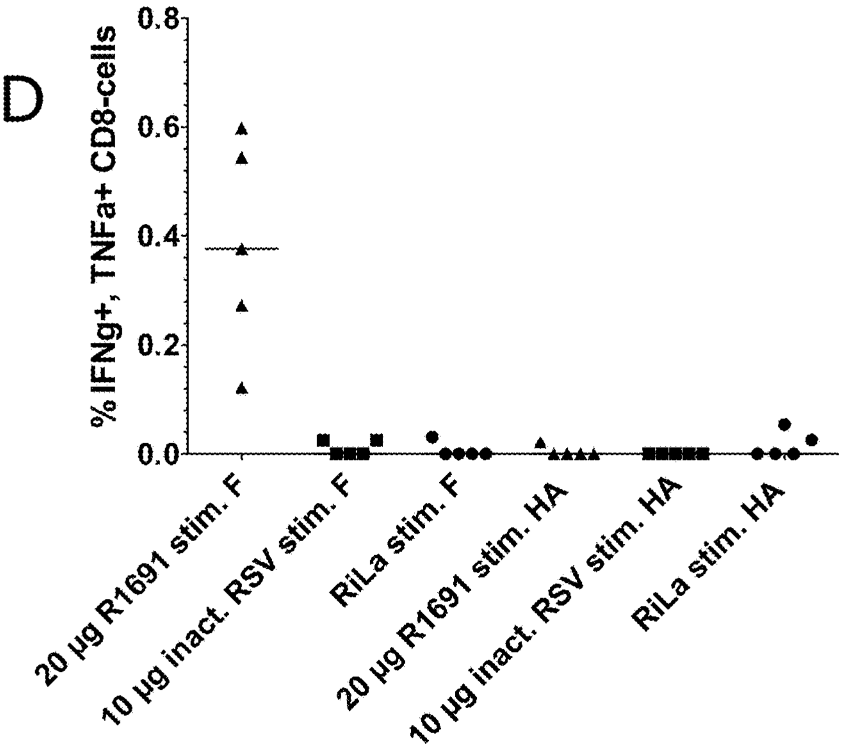
Figs. 8C-D

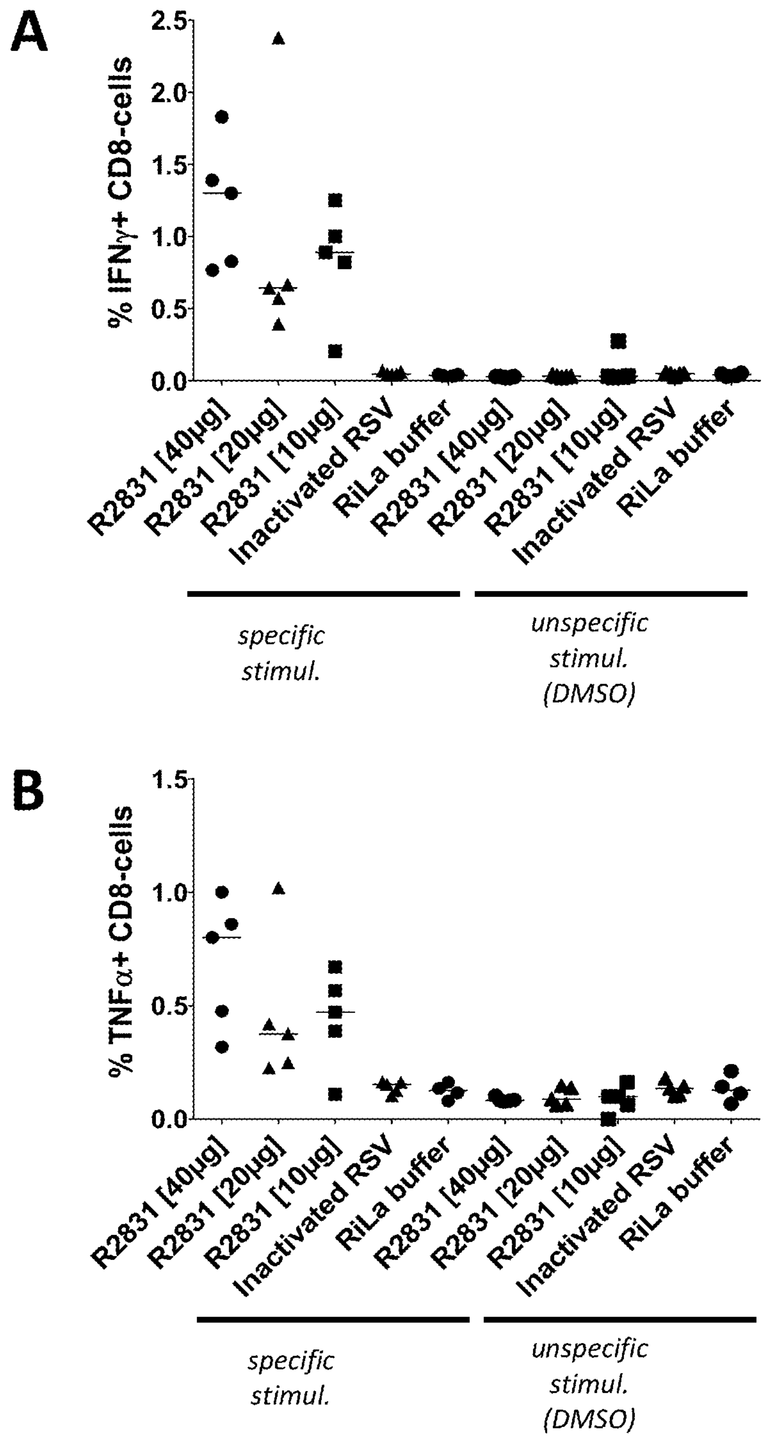
Figs. 9A-B

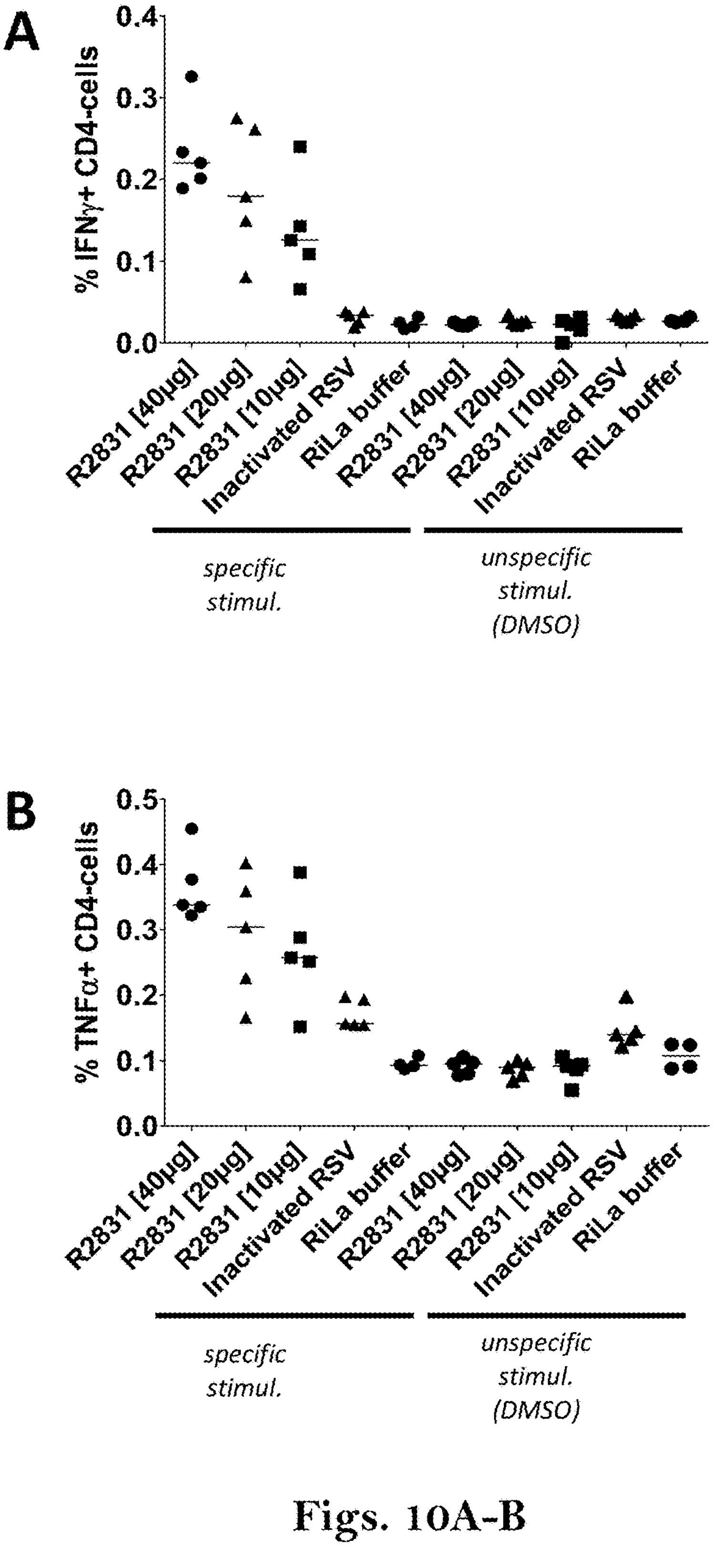
Figs. 10A-B

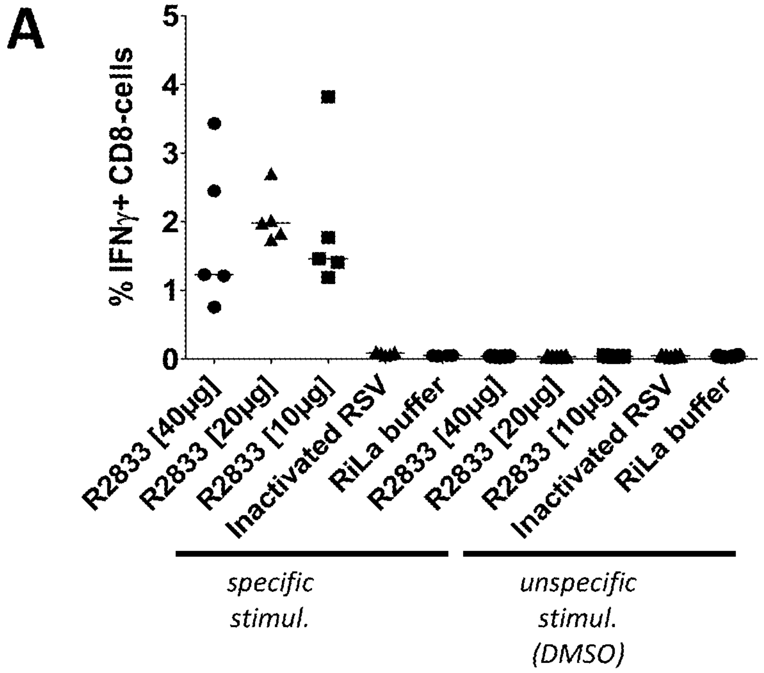
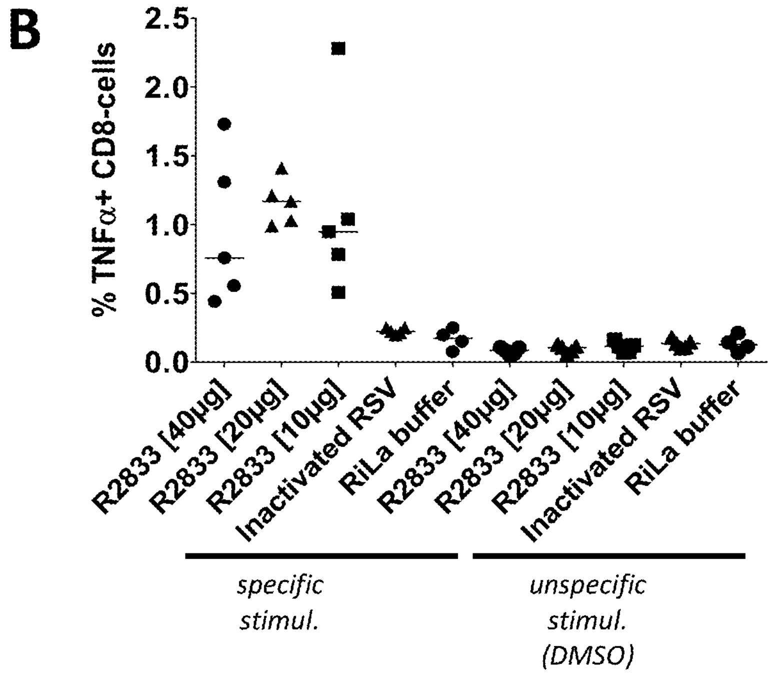
Figs. 11A-B

A
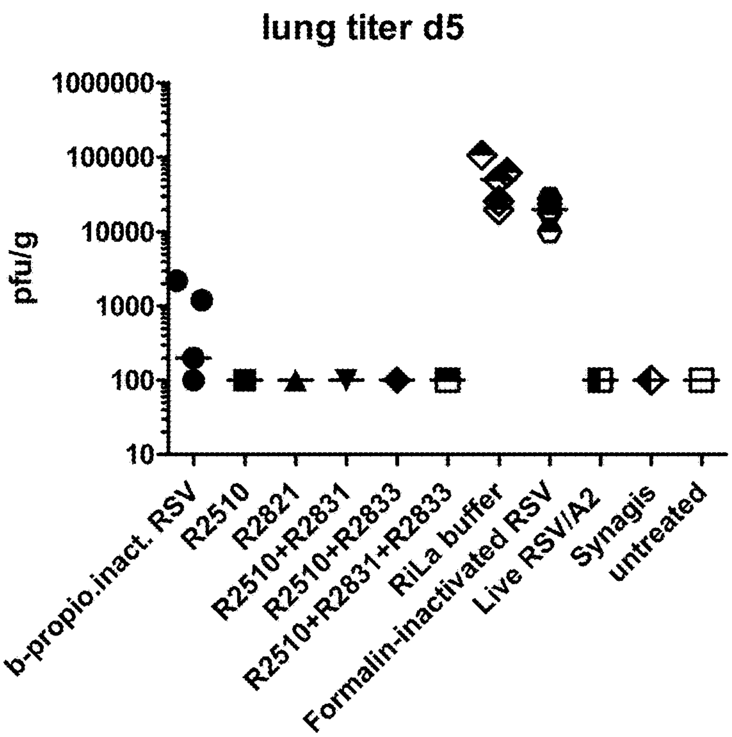
B
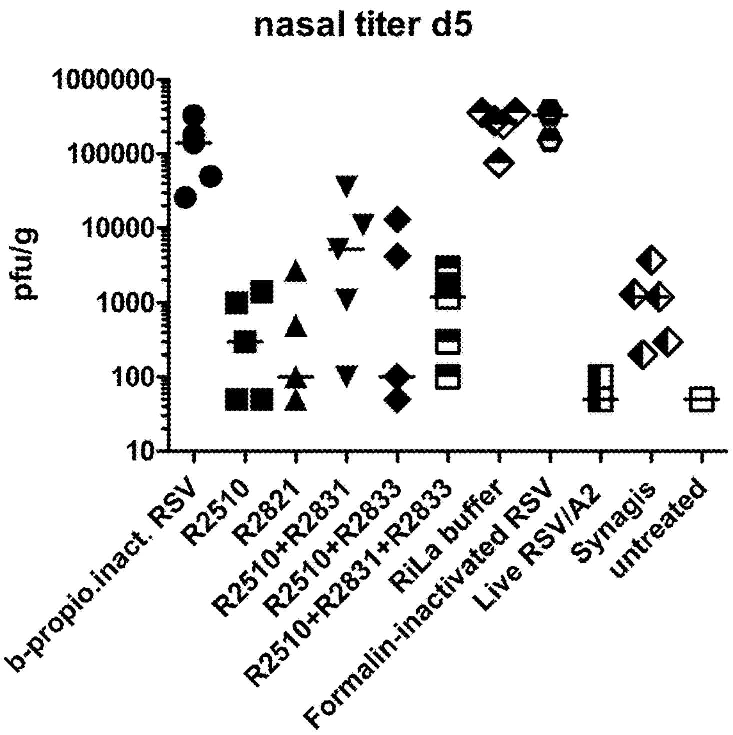
Figs. 14A-B

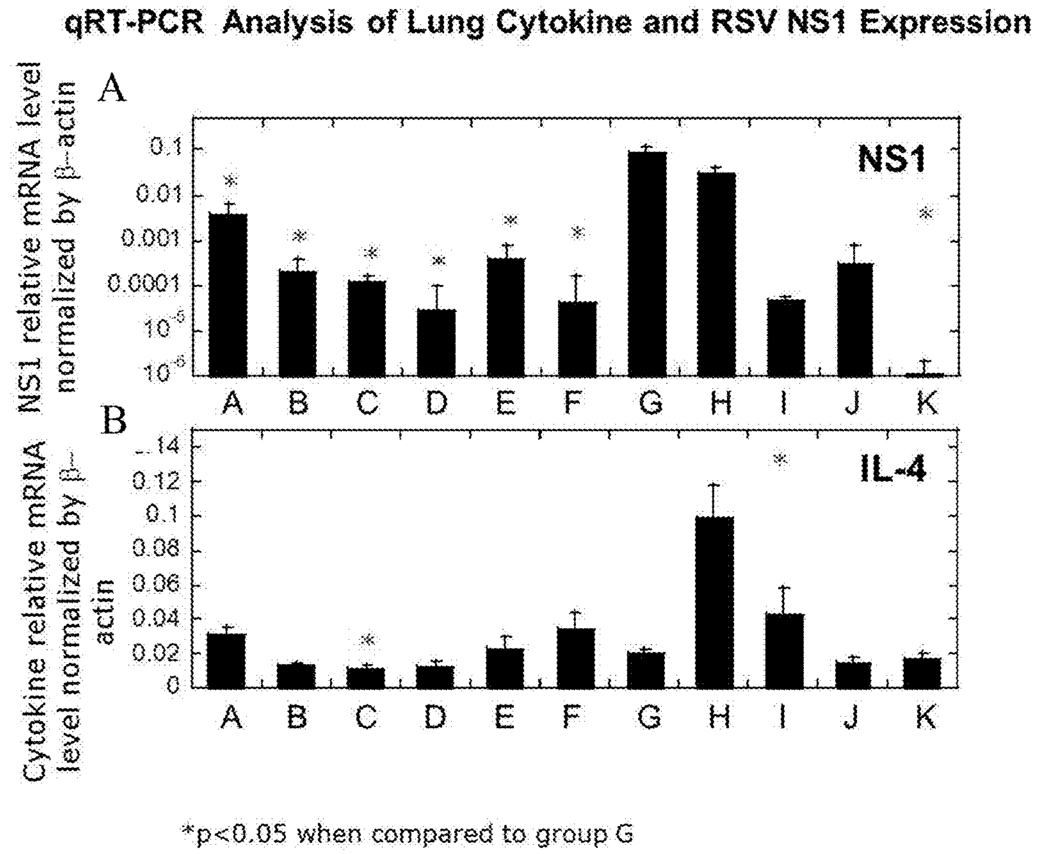
Figs. 16A-B

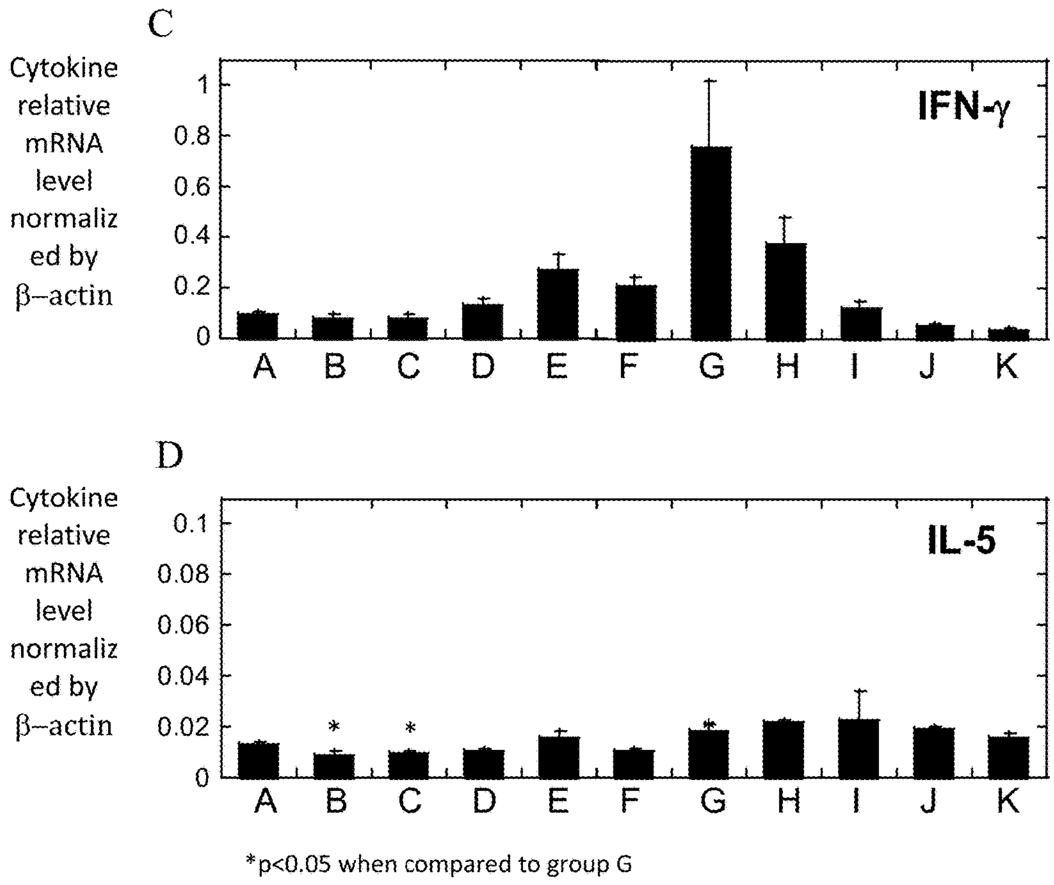
Figs. 16C-D

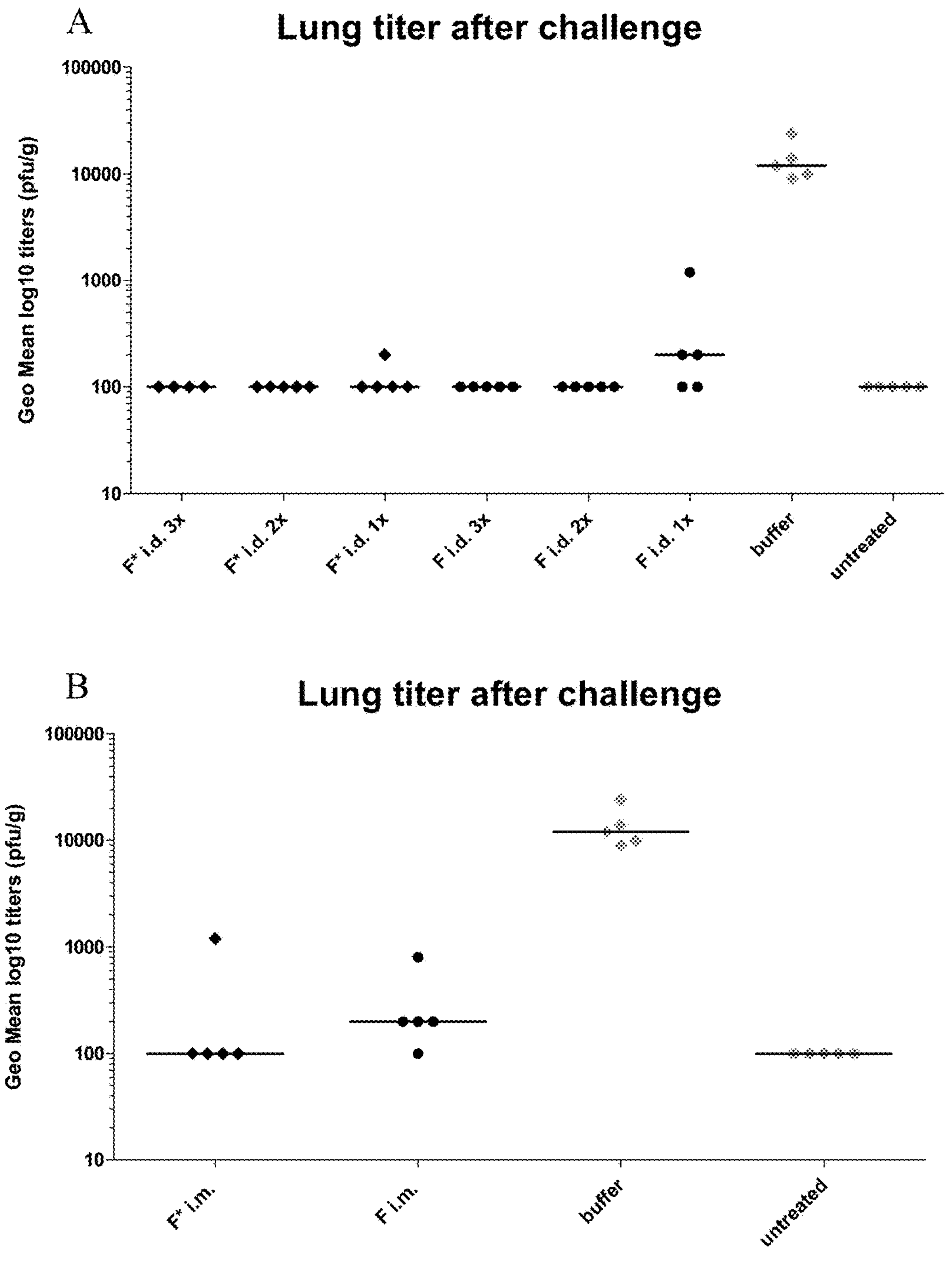
Figs. 17A-B

RESPIRATORY SYNCYTIAL VIRUS (RSV) VACCINE

The present application is a continuation of U.S. application Ser. No. 15/048,439, filed Feb. 19, 2016, which is a continuation of International Application No. PCT/EP2014/002301, filed Aug. 21, 2014, which claims priority benefit of European Application No. PCT/EP2013/002518, filed Aug. 21, 2013, the entire text of each of the above referenced disclosures being specifically incorporated herein by reference.

BACKGROUND OF THE INVENTION

The present invention relates to an mRNA sequence, comprising a coding region, encoding at least one antigenic peptide or protein of Respiratory syncytial virus (RSV) or a fragment, variant or derivative thereof. Additionally the present invention relates to a composition comprising a plurality of mRNA sequences comprising a coding region, encoding at least one antigenic peptide or protein of Respiratory syncytial virus (RSV) or a fragment, variant or derivative thereof.

Furthermore it also discloses the use of the mRNA sequence or the composition comprising a plurality of mRNA sequences for the preparation of a pharmaceutical composition, especially a vaccine, e.g. for use in the prophylaxis or treatment of RSV infections. The present invention further describes a method of treatment or prophylaxis of RSV infections using the mRNA sequence.

The global medical need and economic impact of RSV is very high. It is the most important cause of acute lower respiratory tract infections (ALRIs) that result in hospital visits during infancy and early childhood. For example, in the United States, more than 60% of infants are infected by RSV during their first RSV season, and nearly all have been infected by 2-3 years of age. Approximately 2.1 million US children less than 5 years of age are treated for RSV disease each year: 3% as inpatients, 25% in emergency departments, and 73% in pediatric practices. Globally, among children less than five years of age, RSV causes an estimated 33.8 million ALRIs each year (more than 22% of all ALRIs), resulting in 66 000-199 000 deaths, 99% of which occur in developing countries. RSV is also a common cause of respiratory disease among the elderly, resulting in as many hospitalizations as influenza in a heavily influenza-immunized population. RSV spreads by respiratory droplets and close contact with infected persons or contaminated objects. In temperate climates, there is an annual winter epidemic. Infants are at highest risk for severe RSV disease in their first 6 months, and hospitalization peaks at 2-3 months of age. Preterm birth and cardiopulmonary disease are risk factors for severe RSV disease. RSV infection of infants elicits partially protective immunity, which appears to wane more rapidly than immunity against most other respiratory viruses. Most children infected with RSV during their first year are re-infected the next year, generally with less severe disease. Re-infections continue throughout life, often with upper respiratory tract symptoms, and sometimes with lower respiratory tract or sinus involvement. Recommended treatment of RSV bronchiolitis consists primarily of respiratory support and hydration. No specific anti-viral therapy is recommended. The neutralizing monoclonal antibody Palivizumab is used for prophylaxis of infants at highest risk for severe infection but is too expensive and impractical for universal use. Currently, there is no licensed RSV vaccine, and developing a safe and effective RSV vaccine is a global public health priority.

In a vaccine trial in the 1960s, infants and young children were immunized with a formalin-inactivated whole virion RSV preparation (FIRSV) or an equivalent paramyxovirus preparation (FIPIV). Five percent of the subjects who were immunized with FI-PIV and then naturally infected by RSV during the next RSV season were hospitalized; 80% of those who were immunized with FI-RSV and then infected by RSV were hospitalized, and two children died. This enhancement of an RSV infection due to vaccination is a specific problem for the development of vaccines against RSV infections (reviewed in Shaw et al. Curr Opin Virol. 2013 June; 3(3):332-42. doi: 10.1016/j.coviro.2013.05.003. Epub 2013 May 30.).

Therefore, Respiratory syncytial virus (RSV) infections are the greatest remaining unmet infant vaccine need in developed countries and an important unmet infant vaccine need worldwide. More than 40 years of effort have not yet resulted in a licensed RSV vaccine for humans.

In summary, RSV which belongs to the virus family of Paramyxoviridae, is one of the most contagious pathogens and makes a substantial contribution to severe respiratory tract infections in infants, the elderly and immunocompromised patients.

As mentioned above, currently a humanised monoclonal antibody against the viral surface F protein is the only prophylactic product on the market which is recommended for infants considered at high risk including pre-term infants and infants with chronic lung disease (The IMpact-RSV Study Group. 1998. Palivizumab, a Humanized Respiratory Syncytial Virus Monoclonal Antibody, Reduces Hospitalization From Respiratory Syncytial Virus Infection in High-risk Infants. Pediatrics, 102(3), S.531-537, Tablan et al. 2003. Guidelines for preventing health-care—associated pneumonia, 2003: recommendations of CDC and the Healthcare Infection Control Practices Advisory Committee. MMWR. Recommendations and Reports: Morbidity and Mortality Weekly Report. Recommendations and Reports/Centers for Disease Control, 53 (RR-3), S.1-36.).

Recent studies with animal models demonstrated that sufficient amounts of neutralising antibodies targeting RSV F protein limit viral replication leading to a less severe course of disease (Singh, S. R. et al., 2007. Immunogenicity and efficacy of recombinant RSV-F vaccine in a mouse model. Vaccine, 25(33), S.6211-6223, Zhan, X. et al., 2007. Respiratory syncytial virus (RSV) F protein expressed by recombinant Sendai virus elicits B-cell and T-cell responses in cotton rats and confers protection against RSV subtypes A and B. Vaccine, 25(52), S.8782-8793, Vaughan, K., et al., 2005. DNA immunization against respiratory syncytial virus (RSV) in infant rhesus monkeys. Vaccine, 23(22), S.2928-2942).

Moreover, it could be shown that a balanced regulatory and effector T cell function is required for viral clearance and reduction of severity of illness (Liu, J. et al., 2010. Epitope-specific regulatory CD4 T cells reduce virus-induced illness while preserving CD8 T-cell effector function at the site of infection. Journal of Virology, 84(20), S.10501-10509).

Despite the above mentioned humanised monoclonal antibody, live-attenuated vaccine viruses were developed which elicit a strong immune response, but which are not recommended for use in the specific target groups (infants, children, the elderly and immunocompromised patients). Also, DNA vectors expressing RSV F protein which bears B-cell epitopes were used to induce the production of neutralizing antibodies. In this context, WO 2008/077527 and WO 96/040945 disclose vectors comprising DNA sequences encoding RSV F protein for the use as vaccines. However, the use of DNA as a vaccine may be dangerous due to unwanted insertion into the genome, possibly leading to interruption of functional genes and cancer or the formation of anti-DNA antibodies.

Therefore it is the object of the underlying invention to provide an mRNA sequence coding for antigenic peptides or proteins of Respiratory syncytial virus (RSV) for the use as vaccine for prophylaxis or treatment of RSV infections, particularly in infants, the elderly and immunocompromised patients.

These objects are solved by the subject matter of the attached claims. Particularly, the objects underlying the present invention are solved according to a first aspect by an inventive mRNA sequence comprising a coding region, encoding at least one antigenic peptide or protein of Respiratory syncytial virus (RSV) or a fragment, variant or derivative thereof.

For the sake of clarity and readability the following scientific background information and definitions are provided. Any technical features disclosed thereby can be part of each and every embodiment of the invention. Additional definitions and explanations can be provided in the context of this disclosure.

Immune System:

The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune Response:

An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. RSV infections. However, this specific response can be supported by an additional unspecific reaction (innate immune response). Therefore, the invention also relates to a compound for simultaneous stimulation of the innate and the adaptive immune system to evoke an efficient adaptive immune response.

Adaptive Immune System:

The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive Immune Response:

The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MEW molecules. The unique ability of B cells to bind and internalize soluble protein antigens via their receptors may also be important to induce T cells. Presenting the antigen on MEW molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular Immunity/Cellular Immune Response:

Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral Immunity/Humoral Immune Response:

Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate Immune System:

The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/Adjuvant Component:

An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Immunostimulatory RNA:

An immunostimulatory RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Antigen:

According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The $CD8^+$ T cells that recognize MHC class I:peptide complexes at the surface of infected cells are specialized to kill any cells displaying foreign peptides and so rid the body of cells infected with viruses and other cytosolic pathogens. The main function of $CD4^+$ T cells ($CD4^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Epitope (Also Called "Antigen Determinant"):

T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Vaccine:

A vaccine is typically understood to be a prophylactic or therapeutic material providing at least one antigen or antigenic function. The antigen or antigenic function may stimulate the body's adaptive immune system to provide an adaptive immune response.

Antigen-Providing mRNA:

An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/Multicistronic mRNA:

mRNA, that typically may have two (bicistronic) or more (multicistronic) open reading frames (ORF). An open reading frame in this context is a sequence of several nucleotide triplets (codons) that can be translated into a peptide or protein. Translation of such a mRNA yields two (bicistronic) or more (multicistronic) distinct translation products (provided the ORFs are not identical). For expression in eukaryotes such mRNAs may for example comprise an internal ribosomal entry site (IRES) sequence.

5'-CAP-Structure:

A 5'-CAP is typically a modified nucleotide, particularly a guanine nucleotide, added to the 5' end of an mRNA-molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present invention to modify the inventive mRNA sequence. Further modified 5'-CAP structures which may be used in the context of the present invention are CAP1 (methylation of the ribose of the adjacent nucleotide of m7GpppN), CAP2 (methylation of the ribose of the $2^{nd}$ nucleotide downstream of the m7GpppN), CAP3 (methylation of the ribose of the $3^{rd}$ nucleotide downstream of the m7GpppN), CAP4 (methylation of the ribose of the $4^{th}$ nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Fragments of Proteins:

"Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of Proteins:

"Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a Sequence:

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a Protein or Peptide:

A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Monocistronic mRNA:

A monocistronic mRNA may typically be an mRNA, that encodes only one open reading frame. An open reading frame in this context is a sequence of several nucleotide triplets (codons) that can be translated into a peptide or protein.

Nucleic Acid:

The term nucleic acid means any DNA- or RNA-molecule and is used synonymous with polynucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

Peptide:

A peptide is a polymer of amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Pharmaceutically Effective Amount:

A pharmaceutically effective amount in the context of the invention is typically understood to be an amount that is sufficient to induce an immune response.

Protein:

A protein typically consists of one or more peptides and/or polypeptides folded into 3-dimensional form, facilitating a biological function.

Poly (C) Sequence:

A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Poly-A-Tail:

A poly-A-tail also called "3'-poly(A) tail" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Stabilized Nucleic Acid:

A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by backbone-modification or modification of the G/C-content of the nucleic acid. Various other methods are known in the art and conceivable in the context of the invention.

Carrier/Polymeric Carrier:

A carrier in the context of the invention may typically be a compound that facilitates transport and/or complexation of another compound. Said carrier may form a complex with said other compound. A polymeric carrier is a carrier that is formed of a polymer.

Cationic Component:

The term "cationic component" typically refers to a charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The definition "cationic" may also refer to "polycationic" components.

Vehicle:

An agent, e.g. a carrier, that may typically be used within a pharmaceutical composition or vaccine for facilitating administering of the components of the pharmaceutical composition or vaccine to an individual.

3'-Untranslated Region (3'UTR):

A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-Untranslated Region (5'UTR):

A 5'-UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-CAP. In the context of the present invention, a 5'UTR corresponds to the sequence of a mature mRNA which is located between the 5'-CAP and the start codon. Preferably, the 5'UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5'Terminal Oligopyrimidine Tract (TOP):

The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

Top Motif:

In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5'end of a sequence which represents a 5'UTR or at the 5'end of a sequence which codes for a 5'UTR. Thus, preferably, a stretch of 3 or more pyrimidine nucleotides is called "TOP motif" in the sense of the present invention if this stretch is located at the 5' end of a respective sequence, such as the inventive mRNA, the 5'UTR element of the inventive mRNA, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

Top Gene:

TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 14221-1363 of the patent application PCT/EP2012/002448WO2013/143700 or homologs or variants thereof, whose disclosure is incorporated herewith by reference. In this context a particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

Fragment of a Nucleic Acid Sequence, Particularly an mRNA:

A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence.

Variant of a Nucleic Acid Sequence, Particularly an mRNA:

A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Homolog of a Nucleic Acid Sequence:

The term "homolog" of a nucleic acid sequence refers to sequences of other species than the particular sequence. It is particular preferred that the nucleic acid sequence is of human origin and therefore it is preferred that the homolog is a homolog of a human nucleic acid sequence.

Jet injection: The term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the inventive mRNA. In a further preferred embodiment, jet injection is used for intradermal injection of the inventive mRNa.

The present invention is based on the surprising finding of the present inventors that an mRNA sequence comprising a coding region, encoding at least one antigenic peptide or protein of Respiratory syncytial virus (RSV) induces antigen-specific immune responses and therefore prevent or at least minimize Respiratory syncytial virus (RSV) infections. It was very surprising for the inventors that the inventive mRNA sequence induces at least the same immune responses than vaccines based on inactivated RSV which consists of the whole virus. Even more surprisingly the inventive mRNA sequence coding for an antigenic protein of RSV induced antigen-specific CD8+-T cells in contrast to a vaccine based on an inactivated RSV. Additionally, in a cotton rat RSV challenge model, the virus titers in the nose and in the lung of mRNA vaccinated animals were much lower compared to animals vaccinated with vaccines based on an inactivated RSV virus. With regard to safety the inventors could show that the mRNA-based RSV vaccine showed no hints for vaccine-mediated disease enhancement, in terms of lung pathology, compared to a vaccine based on formalin-inactivated virus. Furthermore, it has surprisingly been found by the inventors that already one single vaccination with the inventive mRNA sequence was sufficient for eliciting an immune response against the administered antigen(s). Specifically, it has been found that one single administration, preferably by intradermal or intramuscular injection, of the inventive mRNA is highly efficient in reducing viral titers in the lung after challenge with RSV virus.

In summary, the inventive mRNA sequence comprising a coding region encoding at least one antigenic peptide or protein of Respiratory syncytial virus (RSV) could provide an effective and safe vaccine, particularly for infants, the elderly and immunocompromised patients.

In this context it is particularly preferred that the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof.

The coding region of the inventive mRNA sequence according to the first aspect of the present invention may occur as a mono-, bi-, or even multicistronic mRNA, i.e. an mRNA sequence which carries the coding sequences of one, two or more proteins or peptides. Such coding sequences in bi-, or even multicistronic mRNAs may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof. In a particularly preferred embodiment of the first aspect of the invention, the inventive mRNA sequence comprises a coding region, encoding at least one antigenic peptide or protein derived from the fusion protein F, the nucleoprotein N, or the M2-1 protein of Respiratory syncytial virus (RSV) or a fragment, variant or derivative thereof.

In this context, the amino acid sequence of the at least one antigenic peptide or protein may be selected from any peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of any RSV isolate or from any synthetically engineered RSV peptide or protein or from a fragment, variant or derivative thereof.

In a particularly preferred embodiment, the full-length protein of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

In this context, the full-length protein from the fusion protein F and the nucleoprotein N are particularly preferred. Furthermore a mutant of the F protein with a deletion of the cytoplasmic tail is particularly preferred. An example of such a deletion mutant is the RSV-Fdel 554-574 long protein according to (Oomens et al. 2006. J. Virol. 80(21):10465-77).

In a further particularly preferred embodiment, a fragment comprising at least one epitope of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

Particularly preferred are the amino acid sequences of the RSV strain long (ATCC VR-26) according to the NCBI accession No. AY911262:

Fusion Protein F of the RSV Strain ATCC VR-26 Long:

```
Amino acid sequence according to SEQ ID No. 1:
MELPILKANA ITTILAAVTF CFASSQNITE EFYQSTCSAV

SKGYLSALRT GWYTSVITIE LSNIKENKCN GTDAKVKLIN

QELDKYKNAV TELQLLMQST TAANNRARRE LPRFMNYTLN

NTKKTNVTLS KKRKRRFLGF LLGVGSAIAS GIAVSKVLHL

EGEVNKIKSA LLSTNKAVVS LSNGVSVLTS KVLDLKNYID

KQLLPIVNKQ SCRISNIETV IEFQQKNNRL LEITREFSVN

AGVTTPVSTY MLTNSELLSL INDMPITNDQ KKLMSNNVQI

VRQQSYSIMS IIKEEVLAYV VQLPLYGVID TPCWKLHTSP

LCTTNTKEGS NICLTRTDRG WYCDNAGSVS FFPQAETCKV

QSNRVFCDTM NSLTLPSEVN LCNVDIFNPK YDCKIMTSKT

DVSSSVITSL GAIVSCYGKT KCTASNKNRG IIKTFSNGCD

YVSNKGVDTV SVGNTLYYVN KQEGKSLYVK GEPIINFYDP

LVFPSDEFDA SISQVNEKIN QSLAFIRKSD ELLHHVNAGK

STTNIMITTI IIVIIVILLS LIAVGLLLYC KARSTPVTLS

KDQLSGINNI AFSN
```

Glycoprotein G of the RSV Strain ATCC VR-26 Long:

```
Amino acid sequence according to SEQ ID No. 2:
MSKNKDQRTA KTLEKTWDTL NHLLFISSGL YKLNLKSIAQ

ITLSILAMII STSLIITAII FIASANHKVT LTTAIIQDAT

SQIKNTTPTY LTQDPQLGIS FSNLSEITSQ TTTILASTTP

GVKSNLQPTT VKTKNTTTTQ TQPSKPTTKQ RQNKPPNKPN

NDFHFEVFNF VPCSICSNNP TCWAICKRIP NKKPGKKTTT

KPTKKPTFKT TKKDLKPQTT KPKEVPTTKP TEEPTINTTK

TNITTTLLTN NTTGNPKLTS QMETFHSTSS EGNLSPSQVS

TTSEHPSQPS SPPNTTRQ
```

Short Hydrophobic Protein SH of the RSV Strain ATCC VR-26 Long:

```
Amino acid sequence according to SEQ ID No. 3:
MENTSITIEF SSKFWPYFTL IHMITTIISL LIIISIMTAI

LNKLCEYNVF HNKTFELPRA RVNT
```

Matrix Protein M of the RSV Strain ATCC VR-26 Long:

```
Amino acid sequence according to SEQ ID No. 4:
METYVNKLHE GSTYTAAVQY NVLEKDDDPA SLTIWVPMFQ

SSMPADLLIK ELANVNILVK QISTPKGPSL RVMINSRSAL

LAQMPSKFTI CANVSLDERS KLAYDVTTPC EIKACSLTCL

KSKNMLTTVK DLTMKTLNPT HDIIALCEFE NIVTSKKVII

PTYLRSISVR NKDLNTLENI TTTEFKNAIT NAKIIPYSGL

LLVITVTDNK GAFKYIKPQS QFIVDLGAYL EKESIYYVTT

NWKHTATRFA IKPMED
```

Nucleoprotein N of the RSV Strain ATCC VR-26 Long:

```
Amino acid sequence according to SEQ ID No. 5:
MALSKVKLND TLNKDQLLSS SKYTIQRSTG DSIDTPNYDV

QKHINKLCGM LLITEDANHK

FTGLIGMLYA MSRLGREDTI KILRDAGYHV KANGVDVTTH

RQDINGKEMK FEVLTLASLT

TEIQINIEIE SRKSYKKMLK EMGEVAPEYR HDSPDCGMII

LCIAALVITK LAAGDRSGLT

AVIRRANNVL KNEMKRYKGL LPKDIANSFY EVFEKHPHFI

DVFVHFGIAQ SSTRGGSRVE

GIFAGLFMNA YGAGQVMLRW GVLAKSVKNI MLGHASVQAE

MEQVVEVYEY AQKLGGEAGF

YHILNNPKAS LLSLTQFPHF SSVVLGNAAG LGIMGEYRGT

PRNQDLYDAA KAYAEQLKEN

GVINYSVLDL TAEELEAIKH QLNPKDNDVE L
```

Large Polymerase L of the RSV Strain ATCC VR-26 Long:

```
Amino acid sequence according to SEQ ID No. 6:
MDPIINGNSA NVYLTDSYLK GVISFSECNA LGSYIFNGPY

LKNDYTNLIS RQNPLIEHMN

LKKLNITQSL ISKYHKGEIK LEEPTYFQSL LMTYKSMTSL

EQIATTNLLK KIIRRAIEIS DVKVYAILNK LGLKEKDKIK

SNNGQDEDNS VITTIIKDDI LSAVKDNQSH LKADKNHSTK

QKDTIKTTLL KKLMCSMQHP PSWLIHWFNL YTKLNNILTQ

YRSNEVKNHG FILIDNQTLS

GFQFILNQYG CIVYHKELKR ITVTTYNQFL TWKDISLSRL

NVCLITWISN CLNTLNKSLG

LRCGFNNVIL TQLFLYGDCI LKLFHNEGFY IIKEVEGFIM

SLILNITEED QFRKRFYNSM LNNITDAANK AQKNLLSRVC

HTLLDKTVSD NIINGRWIIL LSKFLKLIKL AGDNNLNNLS

ELYFLFRIFG HPMVDERQAM DAVKVNCNET KFYLLSSLSM

LRGAFIYRII KGFVNNYNRW
```

-continued

PTLRNAIVLP LRWLTYYKLN TYPSLLELTE RDLIVLSGLR

FYREFRLPKK VDLEMIINDK

AISPPKNLIW TSFPRNYMPS HIQNYIEHEK LKFSESDKSR

RVLEYYLRDN KFNECDLYNC

VVNQSYLNNP NHVVSLTGKE RELSVGRMFA MQPGMFRQVQ

ILAEKMIAEN ILQFFPESLT

RYGDLELQKI LELKAGISNK SNRYNDNYNN YISKCSIITD

LSKFNQAFRY ETSCICSDVL

DELHGVQSLF SWLHLTIPHV TIICTYRHAP PYIRDHIVDL

NNVDEQSGLY RYHMGGIEGW

CQKLWTIEAI SLLDLISLKG KFSITALING DNQSIDISKP

VRLMEGQTHA QADYLLALNS

LKLLYKEYAG IGHKLKGTET YISRDMQFMS KTIQHNGVYY

PASIKKVLRV GPWINTILDD

FKVSLESIGS LTQELEYRGE SLLCSLIFRN VWLYNQIALQ

LKNHALCNNK LYLDILKVLK

HLKTFFNLDN IDTALTLYMN LPMLFGGGDP NLLYRSFYRR

TPDFLTEAIV HSVFILSYYT

NHDLKDKLQD LSDDRLNKFL TCIITFDKNP NAEFVTLMRD

PQALGSERQA KITSEINRLA

VTEVLSTAPN KIFSKSAQHY TTTEIDLNDI MQNIEPTYPH

GLRVVYESLP FYKAEKIVNL

ISGTKSITNI LEKTSAIDLT DIDRATEMMR KNITLLIRIL

PLDCNRDKRE ILSMENLSIT ELSKYVRERS WSLSNIVGVT

SPSIMYTMDI KYTTSTIASG IIIEKYNVNS LTRGERGPTK

PWVGSSTQEK KTMPVYNRQV LTKKQRDQID LLAKLDWVYA

SIDNKDEFME ELSIGTLGLT

YEKAKKLFPQ YLSVNYLHRL TVSSRPCEFP ASIPAYRTTN

YHFDTSPINR ILTEKYGDED

IDIVFQNCIS FGLSLMSVVE QFTNVCPNRI ILIPKLNEIH

LMKPPIFTGD VDIHKLKQVI QKQHMFLPDK ISLTQYVELF

LSNKTLKSGS HVNSNLILAH KISDYFHNTY ILSTNLAGHW

ILIIQLMKDS KGIFEKDWGE GYITDHMFIN LKVFFNAYKT

YLLCFHKGYG KAKLECDMNT

SDLLCVLELI DSSYWKSMSK VFLEQKVIKY ILSQDASLHR

VKGCHSFKLW FLKRLNVAEF

TVCPWVVNID YHPTHMKAIL TYIDLVRMGL INIDRIHIKN

KHKFNDEFYT SNLFYINYNF

SDNTHLLTKH IRIANSELEN NYNKLYHPTP ETLENILANP

IKSNDKKTLN DYCIGKNVDS

-continued

IMLPLLSNKK LVKSSAMIRT NYSKQDLYNL FPTVVIDRII

DHSGNTAKSN QLYTTTSHQI

SLVHNSTSLY CMLPWHHINR FNFVFSSTGC KISIEYILKD

LKIKDPNCIA FIGEGAGNLL LRTVVELHPD IRYIYRSLKD

CNDHSLPIEF LRLYNGHINI DYGENLTIPA TDATNNIHWS

YLHIKFAEPI SLFVCDAELP VTVNWSKIII EWSKHVRKCK

YCSSVNKCTL IVKYHAQDDI

DFKLDNITIL KTYVCLGSKL KGSEVYLVLT IGPANIFPVF

NVVQNAKLIL SRTKNFIMPK

KADKESIDAN IKSLIPFLCY PITKKGINTA LSKLKSVVSG

DILSYSIAGR NEVFSNKLIN HKHMNILKWF NHVLNFRSTE

LNYNHLYMVE STYPYLSELL NSLTTNELKK LIKITGSLLY

NFHNE

M2-1 Protein of the RSV Strain ATCC VR-26 Long:

Amino acid sequence according to SEQ ID No. 7:
MSRRNPCKFE IRGHCLNGKR CHFSHNYFEW PPHALLVRQN

FMLNRILKSM DKSIDTLSEI

SGAAELDRTE EYALGVVGVL ESYIGSINNI TKQSACVAMS

KLLTELNSDD IKKLRDNEEL

NSPKIRVYNT VISYIESNRK NNKQTIHLLK RLPADVLKKT

IKNTLDIHKS ITINNPKELT VSDTNDHAKN NDTT

M2-2 Protein of the RSV Strain ATCC VR-26 Long:

Amino acid sequence according to SEQ ID No. 8:
MTMPKIMILP DKYPCSITSI LITSRCRVTM YNRKNTLYFN

QNNPNNHMYS PNQTFNEIHW

TSQDLIDTIQ NFLQHLGVIE DIYTIYILVS

Phosphoprotein P of the RSV Strain ATCC VR-26 Long:

Amino acid sequence according to SEQ ID No. 9:
MEKFAPEFHG EDANNRATKF LESIKGKFTS PKDPKKKDSI

ISVNSIDIEV TKESPITSNS TIINPTNETD DNAGNKPNYQ

RKPLVSFKED PIPSDNPFSK LYKETIETFD NNEEESSYSY

EEINDQTNDN ITARLDRIDE KLSEILGMLH TLVVASAGPT

SARDGIRDAM VGLREEMIEK

IRTEALMTND RLEAMARLRN EESEKMAKDT SDEVSLNPTS

EKLNNLLEGN DSDNDLSLED

F

Non-Structural Protein NS1 of the RSV Strain ATCC VR-26 Long:

Amino acid sequence according to SEQ ID No. 10:
MGSNSLSMIK VRLQNLFDND EVALLKITCY TDKLIHLTNA -continued

```
LAKAVIHTIK LNGIVFVHVI

TSSDICPNNN IVVKSNFTTM PVLQNGGYIW EMMELTHCSQ

PNGLIDDNCE IKFSKKLSDS

TMTNYMNQLS ELLGFDLNP
```

Non-Structural Protein NS2 of the RSV Strain ATCC VR-26 Long:

```
Amino acid sequence according to SEQ ID No. 11:
MDTTHNDTTP QRLMITDMRP LSLETTITSL TRDIITHRFI

YLINHECIVR KLDERQATFT FLVNYEMKLL HKVGSTKYKK

YTEYNTKYGT FPMPIFINHD GFLECIGIKP TKHTPIIYKY DLNP
```

In the context of the invention, additionally to the here disclosed amino acid sequences according to SEQ ID Nos. 1-11, also amino acid sequences of different Respiratory syncytial virus (RSV) isolates can be used according to the invention and are incorporated herewith. These Respiratory syncytial virus (RSV) isolates show preferably an identity of at least 70%, more preferably of at least 80% and most preferably of at least 90% with the amino acid sequences according to SEQ ID Nos. 1-11.

Furthermore, in this context the coding region encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof, may be selected from any nucleic acid sequence comprising a coding region derived from any Respiratory syncytial virus (RSV) isolate or a fragment or variant thereof.

Particularly preferred are the wild type mRNA sequences of the coding regions of the RSV strain long (ATCC VR-26) according to the NCBI accession No. AY911262:

mRNA Coding for the Fusion Protein F of the RSV Strain ATCC VR-26 Long:

```
mRNA sequence according to SEQ ID No. 12:
auggaguugccaauccucaaagcaaaugcaauuaccacaauccucgcugc

agucacauuuugcuuugcuucuagucaaaacaucacugaagaauuuuauc

aaucaacaugcagugcaguuagcaaaggcuaucuuagugcucuaagaacu

gguugguauacuaguguuauaacuauagaauuaaguaauaucaaggaaaa

uaaguguaauggaacagaugcuaagguaaaauugauaaaccaagaauuag

auaaauauaaaaaugcuguaacagaauugcaguugcucaugcaaagcaca

acagcagcaaacaaucgagccagaagagaacuaccaagguuuaugaauua

uacacucaacaauaccaaaaaaaccaauguaacauuaagcaagaaaagga

aaagaagauuucuugguuuuuuguuagguguuggaucugcaaucgccagu

ggcauugcuguaucuaagguccugcacuuagaaggagaagugaacaagau

caaaagugcucuacuauccacaaacaaggccguagucagcuuaucaaaug

gaguuagugucuuaaccagcaaaguguuagaccucaaaaacuauauagau

aaacaauuguuaccuauugugaauaagcaaagcugcagaauaucaaauau
```

-continued

```
agaaacugugauagaguuccaacaaaagaacaacagacuacuagagauua

ccagggaauuuaguguuaaugcagguguaacuacaccuguaagcacuuac

auguuaacuaauagugaauuauugucauuaaucaaugauaugccuauaac

aaaugaucagaaaaaguuaauguccaacaauguucaaauaguuagacagc

aaaguuacucuaucauguccauaauaaaagaggaagucuuagcauaugua

guacaauuaccacuauauggugugauagauacaccuuguuggaaauuaca

cacaucccucuauguacaaccaacacaaaagaagggucaaacaucuguu

uaacaagaacugacagaggaugguacugugacaaugcaggaucaguaucu

uucuucccacaagcugaaacauguaaaguucaaucgaaucgaguauuuug

ugacacaaugaacaguuuaacauuaccaagugaaguaaaucucugcaaug

uugacauauucaaucccaaauaugauuguaaaauuaugacuucaaaaaca

gauguaagcagcuccguuaucacaucucuaggagccauugugucaugcua

uggcaaaacuaaauguacagcauccaauaaaaaucguggaaucauaaaga

cauuuucuaacgggugugauuauguaucaaauaaaggggugacacugug

ucuguagguaacacauuauauuauguaaauaagcaagaaggcaaaagucu

cuauguaaaaggugaaccaauaauaaauuucuaugacccauuaguauucc

ccucugaugaauuugaugcaucaauaucucaagucaaugagaagauuaac

cagaguuuagcauuuauucguaaauccgaugaauuauuacaucauguaaa

ugcugguaaaucaaccacaaauaucaugauaacuacuauaauuauaguga

uuauaguaauauuguuaucauuaauugcuguuggacugcuccuauacugu

aaggccagaagcacaccagucacacuaagcaaggaucaacugagugguau

aaauaauauugcauuuaguaacuga
```

mRNA Coding for the Glycoprotein G of the RSV Strain ATCC VR-26 Long:

```
mRNA sequence according to SEQ ID No. 13:
auguccaaaaacaaggaccaacgcaccgcuaagacacuagaaaagaccug

ggacacucucaaucauuuauuauucauaucaucgggcuuauauaaguuaa

aucuuaaaucuauagcacaaaucacauuauccauucuggcaaugauaauc

ucaacuucacuuauaauuacagccaucauauucauagccucggcaaacca

caaagucacacuaacaacugcaaucauacaagaugcaacaagccagauca

agaacacaaccccaacauaccucacucaggauccucagcuuggaaucagc

uucuccaaucugucugaaauuacaucacaaaccaccaccauacuagcuuc

aacaacaccaggagucaagucaaaccugcaacccacaacagucaagacua

aaaacacaacaacaacccaaacacaacccagcaagcccacuacaaaacaa

cgccaaaacaaaccaccaaacaaacccaauaaugauuuucacuucgaagu

guuuaacuuuguacccugcagcauaugcagcaacaauccaaccugcuggg

cuaucugcaaaagaauaccaaacaaaaaaccaggaaagaaaaccaccacc

aagccuacaaaaaaaccaaccuucaagacaaccaaaaaagaucucaaacc

ucaaaccacuaaaccaaaggaaguacccaccaccaagcccacagaagagc

caaccaucaacaccaccaaaacaaacaucacaacuacacugcucaccaac

aacaccacaggaaauccaaaacucacaagucaaauggaaaccuuccacuc
```

-continued aaccuccuccgaaggcaaucuaagcccuucucaagucuccacaacauccg agcacccaucacaacccucaucuccacccaacacaacacgccaguag mRNA Coding for the Short Hydrophobic Protein SH of the RSV Strain ATCC VR-26 Long:

mRNA sequence according to SEQ ID No. 14:
auggaaaauacauccauaacaauagaauucucaagcaaauucuggccuu acuuuacacuaauacacaugaucacaacaauaaucucuuugcuaaucau aaucuccaucaugacugcaauacuaaacaaacuuugugaauauaacgua uuccauaacaaaaccuuugaguuaccaagagcucgagucaacacauag mRNA Coding for the Matrixprotein M of the RSV Strain ATCC VR-26 Long:

mRNA sequence according to SEQ ID No. 15:
auggaaacauacgugaacaagcuucacgaaggcuccacauacacagcugc uguucaauacaauguccuagaaaaagacgaugacccugcaucacuuacaa uaugggugcccauguuccaaucaucuaugccagcagauuuacuuauaaaa gaacuagcuaaugucaacauacuagugaaacaaauauccacacccaaggg accuucacuaagagucaugauaaacucaagaagugcauugcuagcacaaa ugcccagcaaauuuaccauaugugcuaauguguccuuggaugaaagaagc aaacuggcauaugauguaaccacacccugugaaaucaaggcauguagucu aacaugccuaaaaucaaaaaauauguuaacuacaguuaaagaucucacua ugaagacacucaaccccacacaugauauuauugcuuuaugugaauuugaa aacauaguaacaucaaaaaaagucauaauaccaacauaccuaagauccau cagugucagaaauaaagaucugaacacacuugaaaauauaacaaccacug aauucaaaaaugccaucacaaaugcaaaaaucaucccuuacucaggauua cuauuagucaucacagugacugacaacaaaggagcauucaaauacauaaa gccgcaaagucaauucauaguagaucuuggagcuuaccuagaaaaagaaa guauauauuauguuaccacaaauuggaagcacacagcuacacgauuugca aucaaacccauggaagauuaa mRNA Coding for the Nucleoprotein N of the RSV Strain ATCC VR-26 Long:

mRNA sequence according to SEQ ID No. 16:
auggcucuuagcaaagucaaguugaaugauacacucaacaaagaucaacu ucugucaucuagcaaauacaccauccaacggagcacaggagauaguauug auacuccuaauuaugaugugcagaaacacaucaauaaguuauguggcaug uuauuaaucacagaagaugcuaaucauaaauucacugguuaauagguau guuauaugcuaugucuagguuaggaagagaagacaccauaaaaauacuca gagaugcgggauaucauguaaaagcaaauggaguagauguaacaacacau cgucaagacaucaaugggaaagaaaugaaauuugaaguguuaacauuggc aagcuuaacaacugaaauucaaaucaacauugagauagaaucuagaaaau ccuacaaaaaaaugcuaaaagaaaugggagagguagcuccagaauacagg caugauucuccugauugugggaugauaauauuauguauagcagcauuagu -continued aauaaccaaauuggcagcaggggauagaucuggucuuacagccgugauua ggagagcuaauaauguccuaaaaaaugaaaugaaacguuacaaaggcuua cuacccaaggauauagccaacagcuucuaugaaguguuugaaaaacaucc ccacuuuauagauguuuuuguucauuuugguauagcacaaucuuccacca gagguggcaguagaguugaagggauuuuugcaggauuguuuaugaaugcc uauggugcagggcaaguaaugcuacgguggggagucuuagcaaaaucagu uaaaaauauuauguuaggacaugcuagugugcaagcagaaauggaacaag uuguugagguuuaugaauaugcccaaaaauuggguggagaagcaggauuc uaccauauauugaacaacccaaaagcaucauuauuaucuuugacucaauu ucccucacuuuuccaguguaguauuaggcaaugcugcuggccuaggcauaa ugggagaguacagagguacaccgaggaaucaagaucuauaugaugcagca aaggcauaugcugaacaacucaaagaaaauggugugauuaacuacagugu auuagacuugacagcagaagaacuagaggcuaucaaacaucagcuuaauc caaaagauaaugauguagagcuuuga mRNA Coding for the Large Polymerase L of the RSV Strain ATCC VR-26 Long:

mRNA sequence according to SEQ ID No. 17:
auggaucccauuauuaauggaaauucugcuaauguuuaucuaaccgauag uuauuuaaaagguguuaucucuuucucagaguguaaugcuuuaggaaguu acauauucaaugguccuuaucucaaaaaugauuauaccaacuuaauuagu agacaaaauccauuaauagaacacaugaaucuaaagaaacuaaauauaac acaguccuuaauaucuaaguaucauaaaggugaaauaaaauuagaagagc cuacuuauuuucagucauuacuuaugacauacaagaguaugaccucguug gaacagauugcuaccacuaauuuacuuaaaaagauaauaagaagagcuau agaaauaagugaugucaaagucuaugcuauauugaauaaacuagggcuua aagaaaaggacaagauuaaauccaacaauggacaggaugaagacaacuca guuauuacgaccauaaucaaagaugauauacuuucagcuguuaaggauaa ucaaucucaucuuaaagcagacaaaaaucacucuacaaaacaaaaagaca caaucaaaacaacacucuugaagaaauuaauguguucaaugcagcauccu ccaucaugguuaauacauugguuuaauuuauacacaaaauuaaacaacau auuaacacaguaucgaucaaaugagguuaaaaaccauggguuuauauuga uagauaaucaaacucuuaguggauuucaauuuauuuugaaucaauauggu uguauaguuuaucauaaggaacucaaaagaauuacugugacaaccuauaa ucaauucuugacauggaaagauauuagccuuaguagauuaaauguuuguu uaauuacauggauuaguaacugcuugaacacauuaaauaaaagcuuaggc uuaagaugcggauucaauaauguuaucuugacacaacuauuccuuuaugg ugauuguauacuaaagcuauuucacaaugagggguucuacauaauaaaag agguagagggauuuauuaugucucuaauuuuaaauauaacagaagaagau caauucagaaaacgauuuuauaauaguaugcucaacaacaucacagaugc ugcuaauaaagcucagaaaaaucugcuaucaagaguaugucauacauuau -continued uagauaagacaguauccgauaauauaauaaauggcagauggauaauucua uuaaguaaguuccuuaaauuaauuaagcuugcaggugacaauaaccuuaa caaucugagugaacuauauuuuuguucagaauauuuggacacccaaugg uagaugaaagacaagccauggaugcuguuaaaguuaauugcaaugagacc aaauuuuacuuguuaagcaguuugaguauguuaagaggugccuuuauaua uagaauuauaaaaggguuuguaaauaauuacaacagauggccuacuuuaa gaaaugcuauuguuuuacccuuaagaugguuaacuuacuauaaacuaaac acuuauccuucuuuguuggaacuuacagaaagagauuugauuguguuauc aggacuacguuucuaucgugaguuucgguugccuaaaaaaguggaucuug aaaugauuauaaaugauaaagcuauaucacccccuaaaaauuugauaugg acuaguuucccuagaaauuauaugccgucacacauacaaaacuauauaga acaugaaaaauuaaaauuuuccgagagugauaaaucaagaagaguauuag aguauuauuuaagagauaacaaauucaaugaaugugauuuauacaacugu guaguuaaucaaaguuaucucaacaacccuaaucaugugguaucauugac aggcaaagaaagagaacucaguguagguagaauguuugcaaugcaaccgg gaauguucagacagguucaaauauuggcagagaaaaugauagcugaaaac auuuuacaauucuuuccugaaagucuuacaagauauggugaucuagaacu acaaaaaauauuagaauugaaagcaggaauaaguaacaaaucaaaucgcu acaaugauaauuacaacaauuacauuaguaagugcucuaucaucacagau cucagcaaauucaaucaagcauuucgauaugaaacgucauguauuuguag ugaugugcuggaugaacugcaugguguacaaucucuauuuuccugguuac auuuaacuauuccucaugucacaauaauaugcacauauaggcaugcaccc cccuauauaagagaucauauuguagaucuuaacaauguagaugaacaaag uggauuauauagauaucacaugggugguauugaaggguggugucaaaaac uauggaccauagaagcuauaucacuauuggaucuaauaucucucaaaggg aaauucucaauuacugcuuuaauuaauggugacaaucaaucaauagauau aagcaaaccagucagacucauggaaggucaaacucaugcucaagcagauu auuugcuagcauuaaauagccuuaaauuacuguauaaagaguaugcaggc auaggucacaaauuaaaaggaacugagacuuauauaucacgagauaugca auuuaugaguaaaacaauucaacauaacgguguauauuacccugcuagua uaaagaaaguccuaagagugggaccguggauaaacacuauacuugaugau uucaaagugagucuagaaucuauagguaguuugacacaagaauuagaaua uagaggugaaagucuauuaugcaguuuaauauuuagaaauguaugguuau auaaucaaauugcucuacaauuaaaaaaucaugcguuauguaacaauaaa uuauauuuggacauauuaaagguucugaaacacuuaaaaaccuuuuuuaa ucuugauaauauugauacagcauuaacauuguauaugaauuuacccaugu uauuugguggugguggaucccaacuuguuauaucgaaguuucuauagaaga acuccugauuuccucacagaggcuauaguucacucuguguucauacuuag uuauuauacaaaccaugacuuaaaagauaaacuucaagauuugucagaug auagauugaauaaguucuuaacaugcauaaucacguuugacaaaaacccu aaugcugaauucguaacauugaugagagauccucaagcuuuagggucuga -continued gagacaagcuaaaauuacuagugaaaucaauagacuggcaguuacagagg uuuugaguacagcuccaaacaaaauauucuccaaaagugcacaacauuau accacuacagagauagaucuaaaugauauuaugcaaaauauagaaccuac auauccucacgggcuaagaguuguuuaugaaaguuuacccuuuuauaaag cagagaaaauaguaaaucuuauaucagguacaaaaucuauaacuaacaua cuggaaaagacuucugccauagacuuaacagauauugauagagccacuga gaugaugaggaaaaacauaacuuugcuuauaaggauacuuccauuggauu guaacagagauaaaagagaaauauugaguauggaaaaccuaaguauuacu gaauuaagcaaauauguuagggaaagaucuuggucuuuauccaauauagu ugguguuacaucacccaguaucauguauacaauggacaucaaauauacaa caagcacuauagcuaguggcauaauuauagagaaauauaauguuaacagu uuaacacguggugagagaggaccaacuaaaccauggguugguucaucuac acaagagaaaaaaacaaugccaguuuauaauagacaaguuuuaaccaaaa aacaaagagaucaaauagaucuauuagcaaaauuggauuggguguaugca ucuauagauaacaaggaugaauucauggaagaacucagcauaggaacccu uggguuaacauaugaaaaggccaaaaaauuauuuccacaauauuuaagug ucaacuauuugcaucgccuuacagucaguaguagaccaugugaauucccu gcaucaauaccagcuuauagaacaacaaauuaucacuuugacacuagccc uauuaaucgcauauuaacagaaaaguauggugaugaagauauugacauag uauuccaaaacuguauaagcuuuggccuuagcuuaaugucaguaguagaa caauuuacuaauguauguccuaacagaauuauucucauaccuaagcuuaa ugagauacauuugaugaaaccucccauauucacaggugauguugauauuc acaaguuaaaacaagugauacaaaaacagcauauguuuuuaccagacaaa auaaguuugacucaauauguggaauuauucuuaaguaacaaaacacucaa aucuggaucucauguuaauucuaauuuaauauuggcacauaaaauaucug acuauuuucauaauacuuacauuuuaaguacuaauuuagcuggacauugg auucuaauuauacaacuuaugaaagauucuaaagguauuuuugaaaaaga uuggggagagggauauauaacugaucauauguuuauuaauuugaaaguuu ucuucaaugcuuauaagaccuaucucuuguguuuucauaaagguuauggc aaagcaaaacuggagugugauaugaacacuucagaucuucuauguguauu ggaauuaauagacaguaguuauuggaagucuaugucuaagguauuuuuag aacaaaaaguuaucaaauacauucuuagccaagaugcaaguuuacauaga guaaaaggaugucauagcuucaaauuaugguuucuuaaacgucuuaaugu agcagaauuuacaguuugcccuuggguuguuaacauagauuaucauccaa cacauaugaaagcaauauuaacuuauauagaucuuguuagaaugggauug auaaauauagauagaauacacauuaaaaauaaacacaaauucaaugauga auuuuauacuucuaaucucuuuuacauuaauuauaacuucucagauaaua cucaucuauuaacuaaacauauaaggauugcuaauucagaauuagaaaau aauuacaacaaauuauaucauccuacaccagaaacccuagagaauauacu agccaauccgauuaaaaguaaugacaaaaagacacugaacgacuauugua -continued uagguaaaaauguugacucaauaauguuaccauuguuaucuaauaagaag cuuguuaaaucgucugcaaugauuagaaccaauuacagcaaacaagaccu guacaaucuauucccuacgguugugaucgauagaauuauagaucauucag guaauacagccaaauccaaccaacuuuacacuacuacuucccaucaaaua ucuuuagugcacaauagcacaucacuuuauugcaugcuuccuuggcauca uauuaauagauucaauuuuguauuuaguucuacagguuguaaaauuagua uagaguauauuuuaaaagaccuuaaaauuaaagauccuaauuguauagca uucauaggugaaggagcagggaauuuauuauugcguacagugguggaacu ucauccugacauaagauauauuuacagaagucugaaagauugcaaugauc auaguuuaccuauugaguuuuuaaggcuauacaauggacauaucaacauu gauuauggugaaaauuugaccauuccugcuacagaugcaaccaacaacau ucauuggucuuauuuacauauaaaguuugcugaaccuaucagucuuuuug uaugugaugccgaauugccuguaacagucaacuggaguaaaauuauaaua gaauggagcaagcauguaagaaaaugcaaguacuguuccucaguuaauaa auguacguuaauaguaaaauaucaugcucaagaugauauugauuucaaau uagacaauauaacuauauuaaaaacuuauguaugcuuaggcaguaaguua aagggaucggagguuuacuuaguccuuacaauagguccugcaaauauauu uccaguauuuaauguaguacaaaaugcuaaauugauacuaucaagaacca aaaauuucaucaugccuaagaaagcugauaaagagucuauugaugcaaau auuaaaaguuugauacccuuucuuuguuacccuauaacaaaaaaaggaau uaauacugcauugucaaaacuaaagaguguuguuaguggagauauacuau cauauucuauagcuggacggaaugaaguuucagcaauaaacuuauaaau cauaagcauaugaacaucuuaaagugguucaaucauguuuuaaauuucag aucaacagaacuaaacuauaaccauuuauauaugguagaaucuacauauc cuuaccuaagugaauuguuaaacagcuugacaacuaaugaacuuaaaaaa cugauuaaaaucacagguagucuguuauacaacuuucauaaugaauaa mRNA Coding for the Protein M2-1 of the RSV Strain ATCC VR-26 Long:

mRNA sequence according to SEQ ID No. 18:
Augucacgaaggaauccuugcaaauuugaaauucgaggucauugcuugaa ugguaagagaugucauuuuagucauaauuauuuugaauggccaccccaug cacugcucguaagacaaaacuuuauguuaaacagaauacuuaagucuaug gauaaaaguauagauaccuuaucagaaauaaguggagcugcagaguugga cagaacagaagaguaugcucuuggguguaguuggagugcuagagaguuaua uaggaucaauaaauaauauaacuaaacaaucagcauguguugccaugagc aaacuccucacugaacucaauagugaugauaucaaaaaacugagagacaa ugaagagcuaaauucacccaagauaagaguguacaauacugucauaucau auauugaaagcaacaggaaaaacaauaaacaaacuauccaucuguuaaaa agauugccagcagacguauugaagaaaaccaucaaaaacacauuggauau ccacaagagcauaaccaucaacaacccaaaagaauuaacuguuagugaua caaaugaccaugccaaaaauaaugauacuaccuga mRNA Coding for the Protein M2-2 of the RSV Strain ATCC VR-26 Long:

mRNA sequence according to SEQ ID No. 19:
augaccaugccaaaaauaaugauacuaccugacaaauauccuuguaguau aacuuccauacuaauaacaaguagauguagagucacuauguauaaucgaa agaacacacuauauuucaaucaaaacaacccaaauaaccauauguacuca ccgaaucaaacauucaaugaaauccauuggaccucacaagacuugauuga cacaauucaaaauuuucuacagcaucuagguguuauugaggauauauaua caauauauauauuagugucauaa mRNA Coding for the Phosphoprotein P of the RSV Strain ATCC VR-26 Long:

mRNA sequence according to SEQ ID No. 20:
auggaaaaguuugcuccugaauuccauggagaagaugcaaacaacagggc uacuaaauuccuagaaucaauaaagggcaaauucacaucaccuaaagauc ccaagaaaaaagauaguaucauaucugucaacucaauagauauagaagua accaaagaaagcccuauaacaucaaauucaaccauuauuaacccaacaaa ugagacagaugauaaugcagggaacaagcccaauuaucaaagaaaaccuc uaguaaguuucaaagaagacccuauaccaagugauaaucccuuuucaaaa cuauacaaagaaaccauagagacauuugauaacaaugaagaagaaucuag cuauucauaugaagaaauaaaugaucagacgaacgauaauauaacugcaa gauuagauaggauugaugaaaaauuaagugaaauacuaggaaugcuucac acauuaguaguagcaagugcaggaccuacaucugcuagggaugguauaag agaugccaugguugguuuaagagaagaaaugauagaaaaaaucagaacug aagcauuaaugaccaaugacagauuagaagcuauggcaagacucaggaau gaggaaagugaaaagauggcaaaagacacaucagaugaagugucucucaa uccaacaucagagaaauugaacaaccuguuggaagggaaugauagugaca augaucuaucacuugaagauuucuga mRNA Coding for the Non-Structural Protein NS1 of the RSV Strain ATCC VR-26 Long:

mRNA sequence according to SEQ ID No. 21:
augggcagcaauucguugaguaugauaaaaguuagauuacaaaauuuguu ugacaaugaugaaguagcauuguuaaaaauaacaugcuauacugacaaau uaauacauuuaacuaaugcuuuggcuaaggcagugauacauacaaucaaa uugaauggcauuguguuugugcauguuauuacaaguagugauauuugccc uaauaauaauauuguaguaaaauccaauuucacaacaaugccagugcuac aaaauggagguuauauaugggaaaugauggaauuaacacauugcucucaa ccuaauggucuaauagaugacaauugugaaauuaaauucuccaaaaaacu aagugauucaacaaugaccaauuauaugaaucaauuaucugaauuacuug gauuugaucuuaauccauaa mRNA Coding for the Non-Structural Protein NS2 of the RSV Strain ATCC VR-26 Long:

```
mRNA sequence according to SEQ ID No. 22:
auggacacaacccacaaugauaccacaccacaaagacugaugaucacaga

caugagaccguugucacuugagacuacaauaacaucacuaaccagagaca

ucauaacacacagauuuauauacuuaauaaaucaugaaugcauagugaga

aaacuugaugaaagacaggccacauuuacauuccuggucaacuaugaaau

gaaacuauugcacaaaguaggaagcacuaaauauaaaaaauauacugaau

acaacacaaaauauggcacuuucccuaugccgauauucaucaaucaugau

ggguucuuagaaugcauuggcauuaagccuacaaagcauacucccauaau

auacaaguaugaucucaauccauag
```

In the context of the invention, additionally to the here disclosed nucleic acid sequences, also nucleic acid sequences of different Respiratory syncytial virus (RSV) isolates are incorporated herewith. These different Respiratory syncytial virus (RSV) isolates show preferably an identity of at least 50%, 60%, 70%, more preferably of at least 80% and most preferably of at least 90% with the nucleic acid sequences according to SEQ ID Nos. 12-22 or of fragments thereof.

In a preferred embodiment, the mRNA sequence according to the invention does not comprise a reporter gene or a marker gene. Preferably, the mRNA sequence according to the invention does not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the mRNA sequence according to the invention does not encode luciferase. In another embodiment, the mRNA sequence according to the invention does not encode GFP or a variant thereof.

In a further preferred embodiment, the mRNA sequence according to the invention does not encode a protein (or a fragment of a protein) derived from a virus belonging to the family of Orthomyxoviridae. Preferably the mRNA sequence does not encode a protein that is derived from an influenza virus, more preferably an influenza A virus. Preferably, the mRNA sequence according to the invention does not encode an influenza A protein selected from the group consisting of hemagglutinin (HA), neuraminidase (NA), nucleoprotein (NP), M1, M2, NS1, NS2 (NEP: nuclear export protein), PA, PB1 (polymerase basic 1), PB1-F2 and PB2. In another preferred embodiment, the mRNA according to the invention does not encode ovalbumin (OVA) or a fragment thereof. Preferably, the mRNA sequence according to the invention does not encode an influenza A protein or ovalbumin.

By a further embodiment, the inventive mRNA preferably comprises at least one of the following structural elements: a 5'- and/or 3'-untranslated region element (UTR element), particularly a 5'-UTR element which comprises or consists of a nucleic acid sequence which is derived from the 5'-UTR of a TOP gene or from a fragment, homolog or a variant thereof, or a 5'- and/or 3'-UTR element which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

In a preferred embodiment of the first aspect of the present invention, the inventive mRNA comprises at least one 5'- or 3'-UTR element. In this context, an UTR element comprises or consists of a nucleic acid sequence which is derived from the 5'- or 3'-UTR of any naturally occurring gene or which is derived from a fragment, a homolog or a variant of the 5'- or 3'-UTR of a gene. Preferably, the 5'- or 3'-UTR element used according to the present invention is heterologous to the coding region of the inventive mRNA sequence. Even if 5'- or 3'-UTR elements derived from naturally occurring genes are preferred, also synthetically engineered UTR elements may be used in the context of the present invention.

In a particularly preferred embodiment of the first aspect of the present invention, the inventive mRNA sequence comprises at least one 5'-untranslated region element (5'UTR element) which comprises or consists of a nucleic acid sequence which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive mRNA is provided by the coding region.

The nucleic acid sequence, which is derived from the 5'UTR of a TOP gene, is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is preferably selected from 5'-UTR elements comprising or consisting of a nucleic acid sequence, which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5' TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'UTR of said sequences.

Preferably, the 5'UTR element comprises or consists of a nucleic acid sequence which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5' TOP motif.

In a particularly preferred embodiment, the 5'UTR element comprises or consists of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 (5'-UTR of human ribosomal protein Large 32 lacking the 5' terminal oligopyrimidine tract: GGCGCTGCCTACGGAGGTGGCAGCCATCTCCT-TCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 or more preferably to a corresponding RNA sequence, wherein, preferably, the fragment is as described above, i.e. being a continuous stretch of nucleotides representing at least 20%, preferably at least 30%, more preferably at least 40%, more preferably at least 50%, even more preferably at least 60%, even more preferably at least 70%, even more preferably at least 80%, and most preferably at least 90%. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the inventive mRNA comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 36 (5'-UTR of ATP5A1 lacking the 5' terminal oligopyrimidine tract: GCGGCTCGGCCATTTT-GTCCCAGTCAGTCCGGAGGCTGCGGCTGCAGAAG-TACCGCC TGCG-GAGTAACTGCAAAG; corresponding to SEQ ID No. 1414 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the inventive mRNA further comprises at least one 3'UTR element, which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term '3'UTR element' refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the inventive mRNA comprises a 3'UTR element which may be derivable from a gene that relates to an mRNA with an enhanced half-life (that provides a stable mRNA), for example a 3'UTR element as defined and described below.

In a particularly preferred embodiment, the 3'UTR element comprises or consists of a nucleic acid sequence which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID No. 1369-1390 of the patent application WO2013/143700 whose disclosure is incorporated herein by reference. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene according to SEQ ID No. 24.

```
Human albumin 3'UTR SEQ ID No. 24:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT (corresponding to

SEQ ID No: 1369 of the patent application

WO2013/143700).
```

In this context, it is particularly preferred that the inventive mRNA comprises a 3'-UTR element comprising a corresponding RNA sequence derived from the nucleic acids according to SEQ ID No. 1369-1390 of the patent application WO2013/143700 or a fragment, homolog or variant thereof.

Most preferably the 3'-UTR element comprises the nucleic acid sequence derived from a fragment of the human albumin gene according to SEQ ID No. 25:

```
albumin7 3'UTR
CATCACATTTAAAAGCATCTCAGCCTACCATGAGAATAAGAGAAAGAAAA

TGAAGATCAATAGCTTATTCATCTCTTTTTCTTTTTCGTTGGTGTAAAGC

CAACACCCTGTCTAAAAAACATAAATTTCTTTAATCATTTTGCCTCTTTT

CTCTGTGCTTCAATTAATAAAAAATGGAAAGAACCT (SEQ ID No.

25 corresponding to SEQ ID No: 1376 of the patent

application WO2013/143700)
```

In this context, it is particularly preferred that the 3'-UTR element of the inventive mRNA comprises or consists of a corresponding RNA sequence of the nucleic acid sequence according to SEQ ID No. 25.

In another particularly preferred embodiment, the 3'UTR element comprises or consists of a nucleic acid sequence which is derived from a 3'UTR of an α-globin gene, preferably a vertebrate α- or β-globin gene, more preferably a mammalian α- or β-globin gene, most preferably a human α- or β-globin gene according to SEQ ID No. 26-28:

```
3'-UTR of Homo sapiens hemoglobin,
alpha 1 (HBA1)
GCTGGAGCCTCGGTGGCCATGCTTCTTGCCCCTTGGGCCTCCCCCCAGCC

CCTCCTCCCCTTCCTGCACCCGTACCCCCGTGGTCTTTGAATAAAGTCTG

AGTGGGCGGC (SEQ ID No: 26 corresponding to SEQ ID

No. 1370 of the patent application WO2013/143700)

3'-UTR of Homo sapiens hemoglobin,
alpha 2 (HBA2)
GCTGGAGCCTCGGTAGCCGTTCCTCCTGCCCGCTGGGCCTCCCAACGGGC

CCTCCTCCCCTCCTTGCACCGGCCCTTCCTGGTCTTTGAATAAAGTCTGA

GTGGGCAG (SEQ ID No: 27 corresponding to SEQ ID

No. 1371 of the patent application WO2013/143700)
```

-continued

```
3'-UTR of Homo sapiens hemoglobin,
beta (HBB)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTGGAT

TCTGCCTAATAAAAAACATTTATTTTCATTGC (SEQ ID No: 28

corresponding to SEQ ID No. 1372 of the patent

application WO2013/143700)
```

For example, the 3'UTR element may comprise or consist of the center, α-complex-binding portion of the 3'UTR of an α-globin gene, such as of a human α-globin gene, preferably according to SEQ ID No. 29:

Center, α-complex-binding portion of the 3'UTR of an α-globin gene (also named herein as "muag") GCCCGATGGGCCTCCCAACGGGCCCTCCTCCCCTCCTTGCACCG (SEQ ID NO. 29 corresponding to SEQ ID No. 1393 of the patent application WO2013/143700).

In this context, it is particularly preferred that the 3'-UTR element of the inventive mRNA comprises or consists of a corresponding RNA sequence of the nucleic acid sequence according to SEQ ID No. 29 or a homolog, a fragment or variant thereof.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Preferably, the at least one 5'UTR element and the at least one 3'UTR element act synergistically to increase protein production from the inventive mRNA as described above.

In a particularly preferred embodiment, the inventive mRNA comprising a coding region, encoding at least one antigenic peptide or protein of Respiratory syncytial virus (RSV) or a fragment, variant or derivative thereof, comprises a histone stem-loop sequence/structure. Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

formula (I) (stem-loop sequence without stem bordering elements):

$$\underbrace{[N_{0-2}GN_{3-5}]}_{\text{stem1}}\ \underbrace{[N_{0-4}(U/T)N_{0-4}]}_{\text{loop}}\ \underbrace{[N_{3-5}CN_{0-2}]}_{\text{stem2}}$$

formula (II) (stem-loop sequence with stem bordering elements):

$$\underbrace{N_{1-6}}_{\substack{\text{stem1}\\ \text{bordering}\\ \text{element}}}\ \underbrace{[N_{0-2}GN_{3-5}]}_{\text{stem1}}\ \underbrace{[N_{0-4}(U/T)N_{0-4}]}_{\text{loop}}\ \underbrace{[N_{3-5}CN_{0-2}]}_{\text{stem2}}\ \underbrace{N_{1-6}}_{\substack{\text{stem2}\\ \text{bordering}\\ \text{element}}}$$

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the first inventive aspect, the inventive mRNA sequence may comprise at least one histone stem-loop sequence according to at least one of the following specific formulae (Ia) or (IIa):

formula (Ia) (stem-loop sequence without stem bordering elements):

$$\underbrace{[N_{0-1}GN_{3-5}]}_{\text{stem1}}\ \underbrace{[N_{1-3}(U/T)N_{0-2}]}_{\text{loop}}\ \underbrace{[N_{3-5}CN_{0-1}]}_{\text{stem2}}$$

formula (IIa) (stem-loop sequence with stem bordering elements):

$$\underbrace{N_{2-5}}_{\substack{\text{stem1}\\ \text{bordering}\\ \text{element}}}\ \underbrace{[N_{0-1}GN_{3-5}]}_{\text{stem1}}\ \underbrace{[N_{1-3}(U/T)N_{0-2}]}_{\text{loop}}\ \underbrace{[N_{3-5}CN_{0-1}]}_{\text{stem2}}\ \underbrace{N_{2-5}}_{\substack{\text{stem2}\\ \text{bordering}\\ \text{element}}}$$

wherein:

N, C, G, T and U are as defined above.

According to a further more particularly preferred embodiment of the first aspect, the inventive mRNA sequence may comprise at least one histone stem-loop sequence according to at least one of the following specific formulae (Ib) or (IIb):

formula (Ib) (stem-loop sequence without stem bordering elements):

$$\underbrace{[N_{1}GN_{4}]}_{\text{stem1}}\ \underbrace{[N_{2}(U/T)N_{1}]}_{\text{loop}}\ \underbrace{[N_{4}CN_{1}]}_{\text{stem2}}$$

formula (IIb) (stem-loop sequence with stem bordering elements):

| $N_{4-5}$ | $[N_1GN_4]$ | $[N_2(U/T)N_1]$ | $[N_4CN_1]$ | $N_{4-5}$ |
|---|---|---|---|---|
| stem1 bordering element | stem1 | loop | stem2 | stem2 bordering element |

wherein:

N, C, G, T and U are as defined above.

A particular preferred histone stem-loop sequence is the sequence according to SEQ ID NO: 30 CAAAGGCTCTTTTCAGAGCCACCA or more preferably the corresponding RNA sequence of the nucleic acid sequence according to SEQ ID NO: 30 (CAAAGGCUCUUUUCAGAGCCACCA SEQ ID NO: 37).

In a particular preferred embodiment of the first aspect of the present invention the inventive mRNA comprises additionally to the coding region encoding at least one antigenic peptide or protein of Respiratory syncytial virus (RSV) or a fragment, variant or derivative thereof, a poly(A) sequence, also called poly-A-tail, preferably at the 3'-terminus of the inventive mRNA. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context, the term "about" refers to a deviation of ±10% of the value(s) it is attached to. This poly(A) sequence is preferably located 3' of the coding region comprised in the inventive mRNA according to the first aspect of the present invention.

According to a further preferred embodiment, the inventive mRNA can be modified by a sequence of at least 10 cytosines, preferably at least 20 cytosines, more preferably at least 30 cytosines (so-called "poly(C) sequence"). Particularly, the mRNA may contain a poly(C) sequence of typically about 10 to 200 cytosine nucleotides, preferably about 10 to 100 cytosine nucleotides, more preferably about 10 to 70 cytosine nucleotides or even more preferably about 20 to 50 or even 20 to 30 cytosine nucleotides. This poly(C) sequence is preferably located 3' of the coding region, more preferably 3' of an optional poly(A) sequence comprised in the inventive mRNA according to the first aspect of the present invention.

In this context, the inventive mRNA sequence may comprise in a specific embodiment:

a.) a 5'-CAP structure, preferably m7GpppN;

b.) a coding region encoding at least one antigenic peptide or protein of Respiratory syncytial virus (RSV), preferably derived from the fusion protein F of Respiratory syncytial virus (RSV);

c.) a poly(A) sequence preferably comprising 64 adenosines; and d.) optionally, a poly(C) sequence, preferably comprising 30 cytosines.

In a particularly preferred embodiment of the first aspect of the present invention the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) a coding region encoding at least one antigenic peptide or protein of Rabies virus, preferably derived from the glycoprotein G (RAV-G) of Rabies virus;

c.) a poly(A) sequence preferably comprising 64 adenosines;

d.) optionally, a poly(C) sequence, preferably comprising 30 cytosines; and e.) a histone-stem-loop, preferably comprising the corresponding RNA sequence of the nucleic acid sequence according to SEQ ID NO: 30.

In a further particularly preferred embodiment of the first aspect of the present invention, the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) a coding region encoding at least one antigenic peptide or protein of Respiratory syncytial virus (RSV), preferably derived from the fusion protein F of Respiratory syncytial virus (RSV);

c.) optionally, a 3'-UTR element derived from an alpha globin gene, preferably comprising the corresponding RNA sequence of the nucleic acid sequence according to SEQ ID NO. 29, a homolog, a fragment, or a variant thereof;

d.) a poly(A) sequence preferably comprising 64 adenosines;

e.) optionally, a poly(C) sequence, preferably comprising 30 cytosines; and f.) a histone-stem-loop, preferably comprising the corresponding RNA sequence of the nucleic acid sequence according to SEQ ID NO: 30.

In another particular preferred embodiment, the inventive mRNA encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) optionally, a 5'-UTR element derived from a TOP gene, preferably derived from the corresponding RNA sequence of the nucleic acid sequence according to SEQ ID NO. 23, a homolog, a fragment, or a variant thereof;

c.) a coding region encoding at least one antigenic peptide or protein of Respiratory syncytial virus (RSV), preferably derived from the fusion protein F of Respiratory syncytial virus (RSV);

d.) optionally, a 3'UTR element derived of a gene providing a stable mRNA, preferably derived from the corresponding RNA sequence of a nucleic acid sequence according to SEQ ID NO. 25, a homolog, a fragment, or a variant thereof;

e.) a poly(A) sequence preferably comprising 64 adenosines;

f.) optionally, a poly(C) sequence, preferably comprising 30 cytosines; and g.) a histone-stem-loop, preferably comprising the corresponding RNA sequence of the nucleic acid sequence according to SEQ ID NO: 30.

The coding region might encode at least partially one of the amino acid sequences according to SEQ ID Nos. 1-11 or fragments, variants or derivatives thereof. Furthermore, the coding region of the inventive mRNA may encode a combination of at least two of these amino acid sequences or a combination of fragments, variants or derivatives thereof. Particularly preferred in this context is a combination of fusion protein F with nucleoprotein N and a combination of fusion protein F and M2-1 protein.

Additionally the coding region might be or might comprise at least partially one of the sequences according to SEQ ID No. 12 to SEQ ID No. 22, or fragments, homologs or variants thereof. Furthermore, the mRNA might comprise a combination of at least two of these sequences or a combination of fragments, homologs or variants thereof.

For further improvement of the resistance to e.g. in vivo degradation (e.g. by an exo- or endo-nuclease), the inventive mRNA may be provided as a stabilized nucleic acid, e.g. in the form of a modified nucleic acid. According to a further embodiment of the invention it is therefore preferred that the inventive mRNA is stabilized, preferably by backbone modifications, sugar modifications and/or base modifications, more preferred stabilized by modification of the G/C-content. All of these modifications may be introduced into the inventive mRNA without impairing the mRNA's function to be translated into the antigenic function derived from the Respiratory syncytial virus (RSV) peptide or protein.

A backbone modification in the context of the present invention is preferably a modification in which phosphates of the backbone of the nucleotides contained in the inventive mRNA are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the inventive mRNA, e.g. methylation of the ribose residue or the like.

According to another embodiment, the inventive mRNA may be modified and thus stabilized by modifying the G (guanosine)/C (cytosine) content of the mRNA, preferably of the coding region thereof.

Therein, the G/C content of the inventive mRNA, preferably of the coding region, is particularly increased compared to the G/C content of the coding region of its particular wild type coding sequence, i.e. the unmodified mRNA. However, the encoded amino acid sequence of the inventive mRNA is preferably not modified compared to the coded amino acid sequence of the particular wild type/unmodified mRNA.

The modification of the G/C-content of the inventive mRNA is based on the fact that RNA sequences having an increased G (guanosine)/C (cytosine) content are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotides while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the coding region of the inventive mRNA according to the invention is increased by at least 7%, more preferably by at least 15%, particularly preferably by at least 20%, compared to the G/C content of the coded region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence. In this context, it is particularly preferable to increase the G/C content of the inventive mRNA to the maximum (i.e. 100% of the substitutable codons), in particular in the coding region, compared to the wild type sequence.

According to a further preferred embodiment of the invention, the inventive mRNA is optimized for translation, preferably optimized for translation by replacing codons for less frequent tRNAs of a given amino acid by codons for more frequently occurring tRNAs of the respective amino acid. This is based on the finding that the translation efficiency is also determined by a different frequency in the occurrence of tRNAs in cells. Thus, if so-called "less frequent codons" are present in the inventive mRNA to an increased extent, the corresponding modified RNA is translated to a significantly poorer degree than in the case where codons coding for more frequent tRNAs are present. Preferably, the coding region of the inventive mRNA is modified compared to the corresponding region of the wild type RNA or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the inventive mRNA can be modified such that codons for which more frequently occurring tRNAs are available are inserted. In other words, according to the invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the inventive mRNA with the "frequent" codons without modifying the amino acid sequence of the protein encoded by the coding region of the inventive mRNA or of the coding region. This preferred embodiment allows provision of a particularly efficiently translated and stabilized (modified) inventive mRNA.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the at least one RNA of the inventive combination vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

In a particularly preferred embodiment, the inventive mRNA sequence according to the first aspect of the present invention comprises, preferably in 5'- to 3'-direction:

a) a 5'-CAP structure, as defined herein, preferably m7GpppN;
b) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or a fragment, variant or derivative thereof;
c) a 3'-UTR element as defined herein, preferably derived of a gene providing a stable mRNA, most preferably the corresponding RNA sequence of the nucleic acid sequence according to SEQ ID No. 29, or a homolog, a fragment or variant thereof;
d) a poly(A) sequence, preferably consisting of 64 adenosines
e) optionally a poly(C) sequence, preferably consisting of 30 cytosines.
f) at least one histone stem-loop sequence, preferably the corresponding RNA sequence of the nucleic acid sequence according to SEQ ID NO. 30.

Most preferably, the inventive mRNA sequence of that specific embodiment comprises the sequence modifications as shown in FIG. 1 (SEQ ID NO. 31) using the example of an inventive mRNA coding for the fusion protein F of RSV long.

In a further particularly preferred embodiment, the inventive mRNA sequence according to the first aspect of the present invention comprises preferably in 5' to 3' direction:

a) a 5'-CAP structure, as defined herein, preferably m7GpppN;
b) a 5'-UTR element as defined herein, preferably a 5'-UTR element which comprises or consists of a nucleic acid sequence which is derived from the 5'-UTR of a TOP gene, preferably the 5'-UTR of human ribosomal protein Large 32 lacking the 5' terminal oligopyrimidine tract according to SEQ ID No. 23 or the corresponding RNA sequence; or a fragment, homolog or variant thereof;
c) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof;
d) a 3'-UTR element, preferably the 3'-UTR element of human albumin according to SEQ ID No. 24 or the corresponding RNA, or a homolog, a fragment or a variant thereof;
e) a poly(A) sequence, preferably consisting of 64 adenosines
f) optionally a poly(C) sequence, preferably consisting of 30 cytosines.
g) at least one histone stem-loop sequence, preferably the corresponding RNA sequence of the nucleic acid sequence according to SEQ ID NO. 30.

Most preferably, the inventive mRNA of that specific embodiment comprises the sequence modifications as shown in FIG. 2 (SEQ ID NO. 32) using the example of an inventive mRNA coding for the fusion protein F of RSV long.

In an even more particularly preferred embodiment the inventive mRNA sequence comprises or consists of the sequences shown in FIG. 1-5 according to SEQ ID Nos. 31 and 35.

In further specific embodiments, the mRNA according to the invention may further comprise an internal ribosome entry site (IRES) sequence or IRES-motif, which may separate several open reading frames, for example if the inventive mRNA encodes for two or more antigenic peptides or proteins. An IRES-sequence may be particularly helpful if the mRNA is a bi- or multicistronic mRNA.

Additionally, the inventive mRNA may be prepared using any method known in the art, including synthetic methods such as e.g. solid phase synthesis, as well as in vitro methods, such as in vitro transcription reactions.

According to one embodiment of the present invention the mRNA comprising a coding region, encoding at least one antigenic peptide or protein of Respiratory syncytial virus (RSV) or a fragment, variant or derivative thereof may be administered naked without being associated with any further vehicle, transfection or complexation agent for increasing the transfection efficiency and/or the immunostimulatory properties of the inventive mRNA or of further comprised nucleic acid.

In a preferred embodiment, the inventive mRNA may be formulated together with a cationic or polycationic compound and/or with a polymeric carrier. Accordingly, in a further embodiment of the invention it is preferred that the inventive mRNA or any other nucleic acid comprised in the inventive pharmaceutical composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the inventive mRNA or any other nucleic acid comprised in the inventive pharmaceutical composition or vaccine can also be associated with a vehicle, transfection or complexation agent for increasing the transfection efficiency and/or the immunostimulatory properties of the inventive mRNA or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

In this context, protamine is particularly preferred.

Additionally, preferred cationic or polycationic proteins or peptides may be selected from the following proteins or peptides having the following total formula (III):

$$(Arg)_l;(Lys)_m;(His)_n;(Orn)_o;(Xaa)_x, \quad \text{(formula (III))}$$

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context the disclosure of WO 2009/030481 is incorporated herewith by reference.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIPS: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex an mRNA or a nucleic acid as defined according to the present invention, and thereby preferably condensing the mRNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the inventive mRNA or any further nucleic acid comprised in the inventive pharmaceutical composition or vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the inventive mRNA or any further nucleic acid comprised in the inventive pharmaceutical composition or vaccine may be formed by disulfide-crosslinked cationic (or polycationic) components.

Preferably, such cationic or polycationic peptides or proteins or polymers of the polymeric carrier, which comprise or are additionally modified to comprise at least one —SH moiety, are selected from, proteins, peptides and polymers as defined above for complexation agent.

In a further particular embodiment, the polymeric carrier which may be used to complex the inventive mRNA or any further nucleic acid comprised in the inventive pharmaceutical composition or vaccine may be selected from a polymeric carrier molecule according to generic formula (IV):

$$L\text{-}P^1\text{—}S\text{—}[S\text{—}P^2\text{—}S]_n\text{—}S\text{—}P^3\text{-}L \quad \text{formula (IV)}$$

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationicpeptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), (AA), or $[(AA)_x]_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), (AA), $[(AA)_x]_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context the disclosure of WO 2011/026641 is incorporated herewith by reference. Each of hydrophilic polymers P' and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (V) above (the brackets are omitted for better readability), wherein any of S, $P^1$ and $P^3$ are as defined herein, typically represent a situation, wherein one-SH-moiety of hydrophilic polymers $P^1$ and $P^3$ was condensed with one —SH-moiety of component $P^2$ of generic formula (V) above, wherein both sulphurs of these —SH-moieties form a disulfide bond —S—S— as defined herein in formula (V). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers P' and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, $\alpha,\beta$ unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH— moiety preferably at one terminal end, but may also contain two or even more —SH-moieties, which may be used to additionally attach further components as defined herein, preferably further functional peptides or proteins e.g.

a ligand, an amino acid component (AA) or $(AA)_x$, antibodies, cell penetrating peptides or enhancer peptides (e.g. TAT, KALA), etc.

In this context, it is particularly preferred that the inventive mRNA is complexed at least partially with a cationic or polycationic compound and/or a polymeric carrier, preferably cationic proteins or peptides. In this context the disclosure of WO 2010/037539 and WO 2012/113513 is incorporated herewith by reference. Partially means that only a part of the inventive mRNA is complexed with a cationic compound and that the rest of the inventive mRNA is (comprised in the inventive pharmaceutical composition or vaccine) in uncomplexed form ("free"). Preferably the ratio of complexed mRNA to:free mRNA (in the inventive pharmaceutical composition or vaccine) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed mRNA to free mRNA in the inventive pharmaceutical composition or vaccine is selected from a ratio of about 1:1 (w/w).

The complexed mRNA in the inventive pharmaceutical composition or vaccine, is preferably prepared according to a first step by complexing the inventive mRNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed mRNA after complexing the mRNA. Accordingly, the ratio of the mRNA and the cationic or polycationic compound and/or the polymeric carrier in the component of the complexed mRNA is typically selected in a range that the mRNA is entirely complexed and no free cationic or polycationic compound or polymeric carrier or only a negligibly small amount thereof remains in the composition.

Preferably the ratio of the mRNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the mRNA to the cationic or polycationic compound and/or the polymeric carrier, preferably as defined herein, in the component of the complexed mRNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of mRNA:cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic compound in the complex is a cationic or polycationic cationic or polycationic protein or peptide and/or the polymeric carrier as defined above. In this specific embodiment the complexed mRNA is also encompassed in the term "adjuvant component".

In a further aspect, the invention provides for a composition comprising a plurality or more than one, preferably 2 to 10, more preferably 2 to 5, most preferably 2 to 4 of the inventive mRNA sequences as defined herein. These inventive compositions comprise more than one inventive mRNA sequences, preferably encoding different peptides or proteins which comprise preferably different pathogenic antigens or fragments, variants or derivatives thereof. Particularly preferred in this context is that at least one mRNA sequence encodes at least one antigenic peptide or protein derived from the fusion protein F of Respiratory syncytial virus (RSV) and that at least one mRNA sequence encodes at least one antigenic peptide or protein derived from another antigen of Respiratory syncytial virus (RSV), particularly of nucleoprotein N or M2-1 protein. Further particularly preferred combinations of antigens are in this context:

F+G (serotype A)+G (serotype B)
F+G (serotype A)+G (serotype B)+M2-1
F+G (serotype A)+G (serotype B)+N
F+G (serotype A)+G (serotype B)+N+M2-1
F+M2-1+N
F+M2-1
F+N
F+G (serotype A)+G (serotype B)+N+M2-1+P+M2-2+M+L
F+G (serotype A)+G (serotype B)+N+M2-1+P+M2-2+M
F+G (serotype A)+G (serotype B)+N+M2-1+P+M2-2+L
F+G (serotype A)+G (serotype B)+N+M2-1+P+M+L
F+G (serotype A)+G (serotype B)+N+M2-1+M2-2+M+L
F+G (serotype A)+G (serotype B)+N+P+M2-2+M+L
F+G (serotype A)+G (serotype B)+M2-1+P+M2-2+M+L Accordingly, in a further particular preferred aspect, the present invention also provides a pharmaceutical composition, comprising at least one inventive mRNA sequence as defined herein or an inventive composition comprising a plurality of inventive mRNA sequences as defined herein and optionally a pharmaceutically acceptable carrier and/or vehicle.

As a first ingredient, the inventive pharmaceutical composition comprises at least one inventive mRNA sequence as defined herein.

As a second ingredient, the inventive pharmaceutical composition may optionally comprise at least one additional pharmaceutically active component. A pharmaceutically active component in this connection is a compound that has a therapeutic effect to heal, ameliorate or prevent a particular indication or disease as mentioned herein, preferably RSV infections. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc. Particularly preferred in this context are RSV vaccines, or RSV immune globulines, e.g. Palivizumab (Synagis®).

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

In a preferred embodiment, the inventive pharmaceutical composition is administered via intradermal or intramuscular injection, preferably by using conventional needle-based injection technique or by using a needle-free system, e.g. jet injection. In a further preferred embodiment, the inventive pharmaceutical composition may be administered by jet injection as defined herein. Preferably, the inventive pharmaceutical composition may be administered intramuscularly by jet injection. According to another embodiment, the pharmaceutical composition is administered intradermally via jet injection.

In a preferred embodiment, the pharmaceutical composition may be administered once, twice or three times, preferably by intradermal or intramuscular injection, preferably by jet injection. According to a certain embodiment, a single administration of the inventive pharmaceutical composition, preferably via intradermal or intramuscular injection, preferably by using jet injection, is sufficient for eliciting an immune response against the at least one antigen encoded by the mRNA sequence according to the invention. In a preferred embodiment, the single administration of the pharmaceutical composition elicits an immune response resulting in virus neutralisation. In this context, one single intradermal or intramuscular injection of the pharmaceutical composition is particularly preferred. Preferably, further administrations of the pharmaceutical composition may optionally be carried out in order to enhance and/or prolong the immune response.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive mRNA sequence as vehicle, transfection or complexation agent.

Furthermore, the inventive pharmaceutical composition may comprise one or more additional adjuvants, which are suitable to initiate or increase an immune response of the innate immune system, i.e. a non-specific immune response, particularly by binding to pathogen-associated molecular patterns (PAMPs). With other words, when administered, the pharmaceutical composition or vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the inventive pharmaceutical composition or vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGIn-sn-glyceroldipalmitoyl); NAGO (neuraminidase-galactose oxidase); nanospheres or nanoparticles of any composition; NISVs (non-ionic surfactant vesicles); PLEURAN™ (□β-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl- 2-ethoxymethyl-1H-imidazo[4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In a further preferred embodiment, it is also possible that the inventive pharmaceutical composition contains besides the antigen-providing mRNA further components, which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

The inventive pharmaceutical composition can additionally contain one or more auxiliary substances in order to increase its immunogenicity or immunostimulatory capacity, if desired. A synergistic action of the inventive mRNA sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives, which may be included in the inventive pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context, it is particularly preferred that the optionally comprised adjuvant component comprises the same inventive mRNA as comprised in the inventive pharmaceutical composition as antigen-providing mRNA e.g. mRNA coding for an antigenic peptide or protein of RSV infections Respiratory syncytial virus (RSV) or fragments, variants or derivatives thereof.

Despite, the inventive pharmaceutical composition may comprise further components for facilitating administration and uptake of components of the pharmaceutical composition. Such further components may be an appropriate carrier or vehicle, additional adjuvants for supporting any immune response, antibacterial and/or antiviral agents.

Accordingly, in a further embodiment, the inventive pharmaceutical composition furthermore comprises a pharmaceutically acceptable carrier and/or vehicle.

Such a pharmaceutically acceptable carrier typically includes the liquid or non-liquid basis of a composition comprising the components of the inventive pharmaceutical composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the pharmaceutical composition according to the invention. The term "compatible" as used here means that these constituents of the inventive pharmaceutical composition are capable of being mixed with the components of the inventive pharmaceutical composition in such a manner that no interaction occurs which would substantially reduce the pharmaceutical effectiveness of the pharmaceutical composition under typical use conditions.

A further component of the inventive pharmaceutical composition may be an immunotherapeutic agent that can be selected from immunoglobulins, preferably IgGs, monoclonal or polyclonal antibodies, polyclonal serum or sera, etc, most preferably immunoglobulins directed against Respiratory syncytial virus (RSV), e.g. Palivizumab. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive antigen-providing mRNA.

Furthermore, in a specific embodiment, additionally to the antigen-providing mRNA further antigens can be included in the inventive pharmaceutical composition and are typically substances such as cells, cell lysates, viruses, attenuated viruses, inactivated viruses, proteins, peptides, nucleic acids or other bio- or macromolecules or fragments thereof. Preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or from fragments, variants or derivatives thereof. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses.

The inventive pharmaceutical composition or vaccine as defined herein may furthermore comprise further additives or additional compounds. Further additives, which may be included in the pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent. Additionally the inventive pharmaceutical composition may comprise small interfering RNA (siRNA) directed against genes of Respiratory syncytial virus (RSV), e.g. siRNA directed against the gene encoding the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV). The inventive pharmaceutical composition typically comprises a "safe and effective amount" of the components of the inventive pharmaceutical composition, particularly of the inventive mRNA sequence(s) as defined herein. As used herein, a "safe and effective amount" means an amount of the inventive mRNA sequence(s) as defined herein as such that is sufficient to significantly induce a positive modification of a disease or disorder or to prevent a disease, preferably RSV infections as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive mRNA sequence as defined herein or the inventive composition comprising a plurality of inventive mRNA sequences as defined herein) may be provided or used as a vaccine. Typically, such a vaccine is as defined above for pharmaceutical compositions. Additionally, such a vaccine typically contains the inventive mRNA sequence as defined herein or the inventive composition comprising a plurality of inventive mRNA sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

In a preferred embodiment, the inventive vaccine is administered via intradermal or intramuscular injection, preferably by using conventional needle-based injection technique or by using a needle-free system, e.g. jet injection. In a further preferred embodiment, the inventive vaccine may be administered by jet injection as defined herein. Preferably, the inventive vaccine is administered intramuscularly by jet injection. According to another embodiment, the vaccine is administered intradermally via jet injection.

In a preferred embodiment, the vaccine may be administered once, twice or three times, preferably by intradermal or intramuscular injection, preferably by jet injection. According to a certain embodiment, a single administration of the inventive vaccine, preferably via intradermal or intramuscular injection, preferably by using jet injection, is sufficient for eliciting an immune response against the at least one antigen encoded by the mRNA sequence according to the invention. In a preferred embodiment, the single administration of the vaccine elicits an immune response resulting in virus neutralisation. In this context, one single intradermal or intramuscular injection of the vaccine is particularly preferred. Preferably, further administrations of the vaccine may optionally be carried out in order to enhance and/or prolong the immune response.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

In a further aspect, the invention is directed to a kit or kit of parts comprising the components of the inventive mRNA sequence, the inventive composition comprising a plurality of inventive mRNA sequences, the inventive pharmaceutical composition or vaccine and optionally technical instructions with information on the administration and dosage of the components.

Beside the components of the inventive mRNA sequence, the inventive composition comprising a plurality of inventive mRNA sequences, the inventive pharmaceutical composition or vaccine the kit may additionally contain a pharmaceutically acceptable vehicle, an adjuvant and at least one further component as defined herein, as well as means for administration and technical instructions. The components of the inventive mRNA sequence, the inventive composition comprising a plurality of inventive mRNA sequences, the inventive pharmaceutical composition or vaccine and e.g. the adjuvant may be provided in lyophilized form. In a preferred embodiment, prior to use of the kit for vaccination, the provided vehicle is than added to the lyophilized components in a predetermined amount as written e.g. in the provided technical instructions. By doing so the inventive mRNA sequence, the inventive composition comprising a plurality of inventive mRNA sequences, the inventive pharmaceutical composition or vaccine, according to the above described aspects of the invention is provided that can afterwards be used in a method as described above, also.

The present invention furthermore provides several applications and uses of the inventive mRNA sequence as defined herein, of the inventive composition comprising a plurality of inventive mRNA sequences as defined herein, of the inventive pharmaceutical composition, of the inventive vaccine, all comprising the inventive mRNA sequence as defined herein or of kits comprising same.

In a further aspect, the invention provides an mRNA sequence encoding at least one antigenic peptide or protein of Respiratory syncytial virus (RSV), or a fragment, variant or derivative thereof, and a composition, a pharmaceutical composition, a vaccine and a kit, all comprising the mRNA sequence for use in a method of prophylactic and/or therapeutic treatment of RSV infections. Consequently, in a further aspect, the present invention is directed to the first medical use of the inventive mRNA sequence, the inventive composition comprising a plurality of inventive mRNA sequences, the inventive pharmaceutical composition, the inventive vaccine, and the inventive kit as defined herein as a medicament. Particularly, the invention provides the use of an mRNA sequence encoding at least one antigenic peptide or protein of Respiratory syncytial virus (RSV), or a fragment, variant or derivative thereof as defined above for the preparation of a medicament.

According to another aspect, the present invention is directed to the second medical use of the mRNA sequence encoding at least one antigenic peptide or protein of Respiratory syncytial virus (RSV), or a fragment, variant or derivative thereof, as defined herein, optionally in form of a composition comprising a plurality of inventive mRNA sequences, a pharmaceutical composition or vaccine, kit or kit of parts, for the treatment of RSV infections as defined herein. Particularly, the mRNA sequence encoding at least one antigenic peptide or protein of Respiratory syncytial virus (RSV), or a fragment, variant or derivative thereof to be used in a method as said above is a mRNA sequence formulated together with a pharmaceutically acceptable vehicle and an optionally additional adjuvant and an optionally additional further component as defined above e.g. a further antigen or a RSV immune globuline. In this context particularly the (prophylactic) treatment of infants, the elderly and immunocompromised patients is preferred. And even more preferred is the (prophylactic) treatment of preterm infants and infants with chronic lung disease.

The inventive mRNA sequence may alternatively be provided such that it is administered for preventing or treating RSV infections by several doses, each dose containing the inventive mRNA sequence encoding at least one antigenic peptide or protein of RSV infections Respiratory syncytial virus (RSV), or a fragment, variant or derivative thereof, e.g. the first dose containing at least one mRNA encoding at least one antigenic peptide or protein derived from the fusion protein F (or fragments, variants or derivatives thereof) and the second dose containing at least one mRNA sequence encoding at least one antigenic peptide or protein derived from a different antigen of Respiratory syncytial virus (RSV), preferably from the nucleoprotein N (or fragments, variants or derivatives thereof), from the M2-1 protein or the glycoprotein G (or fragments, variants or derivatives thereof). By that embodiment, both doses are administered in a staggered way, i.e. subsequently, shortly one after the other, e.g. within less than 10 minutes, preferably less than 2 minutes, and at the same site of the body to achieve the same immunological effect as for administration of one single composition containing both, e.g. the mRNA encoding the fusion protein F and the mRNA encoding the nucleoprotein N.

According to a specific embodiment, the inventive mRNA sequence, or the inventive pharmaceutical composition or vaccine may be administered to the patient as a single dose. In certain embodiments, the inventive mRNA sequence or the inventive pharmaceutical composition or vaccine may be administered to a patient as a single dose followed by a second dose later and optionally even a third, fourth (or more) dose subsequent thereto etc. In accordance with this embodiment, booster inoculations with the inventive mRNA sequence or the inventive pharmaceutical composition or vaccine may be administered to a patient at specific time intervals, preferably as defined below, following the second (or third, fourth, etc.) inoculation. In this context, it is particularly preferred that several doses comprise the same mRNA sequence encoding the same antigenic peptide or protein of Respiratory syncytial virus (RSV), e.g. fusion protein F. In that embodiment the doses are given in a specific time period e.g. 20-30 days. For example for post-exposure prophylaxis at least 5 doses of the inventive mRNA sequence or inventive pharmaceutical composition or vaccine can be administered in 20-30 days.

In a preferred embodiment, inventive mRNA sequence, inventive pharmaceutical composition or vaccine is administered via intradermal or intramuscular injection, preferably by using conventional needle-based injection technique or by using a needle-free system, e.g. jet injection. In a further preferred embodiment, the inventive mRNA sequence, inventive pharmaceutical composition or vaccine may be administered by jet injection as defined herein. Preferably, the inventive mRNA sequence, inventive pharmaceutical composition or vaccine is administered intramuscularly by jet injection. According to another embodiment, the inventive mRNA sequence, inventive pharmaceutical composition or vaccine is administered intradermally via jet injection.

In a preferred embodiment, the inventive mRNA sequence, inventive pharmaceutical composition or vaccine may be administered once, twice or three times, preferably by intradermal or intramuscular injection, preferably by jet injection. According to a certain embodiment, a single administration of the inventive mRNA sequence, inventive pharmaceutical composition or vaccine, preferably via intradermal or intramuscular injection, preferably by using jet injection, is sufficient for eliciting an immune response against the at least one antigen encoded by the mRNA sequence according to the invention. In a preferred embodiment, the single administration of the inventive mRNA sequence, inventive pharmaceutical composition or vaccine elicits an immune response resulting in virus neutralisation. In this context, one single intradermal or intramuscular injection of the inventive mRNA sequence, inventive pharmaceutical composition or vaccine is particularly preferred. Preferably, further administrations of the inventive mRNA sequence, inventive pharmaceutical composition or vaccine may optionally be carried out in order to enhance and/or prolong the immune response.

In certain embodiments, such booster inoculations with the inventive mRNA sequence or inventive pharmaceutical composition or vaccine may utilize an additional compound or component as defined for the inventive mRNA sequence or inventive pharmaceutical composition or vaccine as defined herein.

According to a further aspect, the present invention also provides a method for expression of an encoded antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) comprising the steps, e.g. a) providing the inventive mRNA sequence as defined herein or the inventive composition comprising a plurality of inventive mRNA sequences as defined herein, b) applying or administering the inventive mRNA sequence as defined herein or the inventive composition comprising a plurality of inventive mRNA sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, preferably RSV infections as defined herein.

In this context, in vitro is defined herein as transfection or transduction of the inventive mRNA as defined herein or of the inventive composition comprising a plurality of inventive mRNA sequences as defined herein into cells in culture outside of an organism; in vivo is defined herein as transfection or transduction of the inventive mRNA or of the inventive composition comprising a plurality of inventive mRNA sequences into cells by application of the inventive mRNA or of the inventive composition to the whole organism or individual and ex vivo is defined herein as transfection or transduction of the inventive mRNA or of the inventive composition comprising a plurality of inventive mRNA sequences into cells outside of an organism or individual and subsequent application of the transfected cells to the organism or individual.

Likewise, according to another aspect, the present invention also provides the use of the inventive mRNA sequence as defined herein or of the inventive composition comprising a plurality of inventive mRNA sequences as defined herein, preferably for diagnostic or therapeutic purposes, for expression of an encoded antigenic peptide or protein, e.g. by applying or administering the inventive mRNA sequence as defined herein or of the inventive composition comprising a plurality of inventive mRNA sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of RSV infections.

In a further aspect, the invention provides a method of treatment or prophylaxis of RSV infections comprising the steps:

a) providing the inventive mRNA sequence, the composition comprising a plurality of inventive mRNA sequences, the pharmaceutical composition or the kit or kit of parts comprising the inventive mRNA sequence as defined above;
b) applying or administering the mRNA sequence, the composition, the pharmaceutical composition or the kit or kit of parts to a tissue or an organism;
c) optionally administering RSV immune globuline.

Taken together, the invention provides in a certain aspect an mRNA sequence comprising a coding region encoding at least one antigenic peptide or protein of Respiratory syncytial virus (RSV). The inventive mRNA sequence is for use in a method of prophylactic and/or therapeutic treatment of infections caused by syncytial virus (RSV). Accordingly, the invention relates to an mRNA sequence as defined herein for use in a method of prophylactic and/or therapeutic treatment of RSV infections.

In the present invention, if not otherwise indicated, different features of alternatives and embodiments may be combined with each other, where suitable. Furthermore, the term “comprising” shall not be narrowly construed as being limited to “consisting of” only, if not specifically mentioned. Rather, in the context of the present invention, “consisting of” is an embodiment specifically contemplated by the inventors to fall under the scope of “comprising”, wherever “comprising” is used herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE FIGURES

The figures shown in the following are merely illustrative and shall describe the present invention in a further way. These figures shall not be construed to limit the present invention thereto.

FIG. 1: G/C optimized mRNA sequence of R1691 coding for RSV-F protein of the RSV long strain (RSV-F long) as comprised in the RSV-F long mRNA vaccine (SEQ ID NO. 31).

FIG. 2: G/C optimized mRNA sequence of R2510 coding for RSV-F protein of the RSV long strain (RSV-F long) as comprised in the RSV-F long mRNA vaccine (SEQ ID NO. 32).

FIG. 3: G/C optimized mRNA sequence of R2821 coding for RSV-F del554-574 mutant protein of the RSV long strain (RSV-F long) (SEQ ID NO. 33).

FIG. 4: G/C optimized mRNA sequence of R2831 coding for RSV-N protein of the RSV long strain (RSV-F long) (SEQ ID NO. 34).

FIG. 5: G/C optimized mRNA sequence of R2833 coding for RSV-M2-1 protein of the RSV long strain (RSV-F long) (SEQ ID NO. 35).

FIGS. 6A-C: show that the RSV-F long mRNA vaccine induces antibody titers against the RSV-F protein comparable to those against inactivated RSV.

Female BALB/c mice were intradermally (i.d.) injected with the RSV-F long mRNA vaccine (160 μg of R1691) or Ringer-Lactate (RiLa buffer) as buffer control. One group was intramuscularly (i.m.) injected with 10 μg of the inactivated RSV long vaccine. All animals received boost injections on days 21 and 35, blood samples were collected on day 49 for the determination of antibody titers of pooled sera as described in Example 2.

As can be seen, the RSV-F long mRNA vaccine induces anti-F protein antibodies of the IgG1 and IgG2a subclasses. Antibody titers are displayed in the graph (n=5 mice/group).

Figure 7:
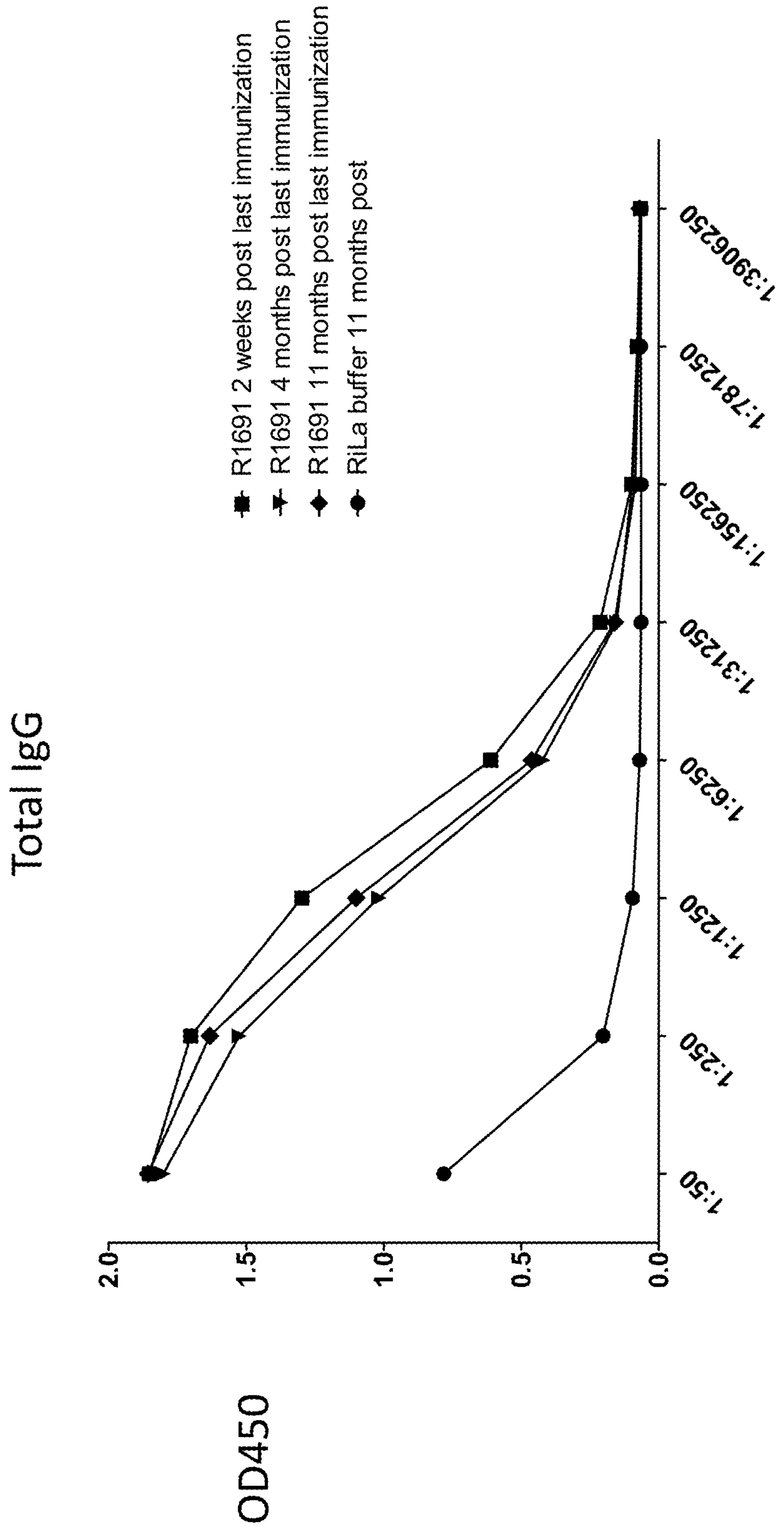

FIG. 7: shows that the RSV-F long mRNA vaccine (R1691) induces a long-lived immune response in mice.

The experiment was performed as described in Example 3 and antibody total IgG titers determined by ELISA.

As can be seen, the antibody titers are stable for at least eleven months after the last boost vaccination.

FIGS. 8A-D: show that the RSV-F long mRNA vaccine (R1691) induces RSV Fusion (F) protein-specific multifunctional $CD8^+$ T cells in mice.

The experiment was performed as described in Example 4 and T cells were analysed by intracellular cytokine staining for the antigen-specific induction of cytokines. Cells were stimulated with a RSV-F peptide (stim. F; KYKNAVTEL) or a control influenza HA peptide (stim. HA; IYSTVASSL). The line in the graph represents the median value (n=5 mice/group).

As can be seen, the RSV-F long mRNA vaccine induces RSV Fusion (F) protein-specific multifunctional $CD8^+$ T cells in contrast to the vaccine based on inactivated RSV which is not able to induce F protein-specific $CD8^+$ T cells.

Figure 9C:
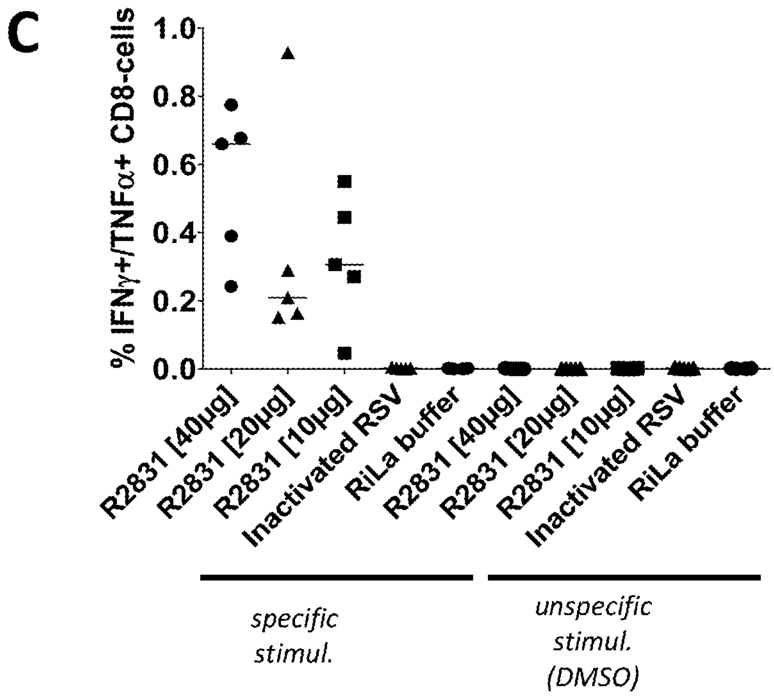

FIGS. 9A-C: show that the RSV-N mRNA vaccine (R2831) induces Nucleoprotein (N)-specific multifunctional $CD8^+$ T cells in mice.

The experiment was performed as described in Example 5 and T cells were analysed by intracellular cytokine staining for the antigen-specific induction of cytokines after stimulation with ProMix RSV-N (15mer peptides). The line in the graph represents the median value (n=5 mice/group).

As can be seen, the RSV-N mRNA vaccine induces RSV Nucleoprotein (N)-specific multifunctional $CD8^+$ T cells in contrast to the vaccine based on inactivated RSV which is not able to induce N protein-specific $CD8^+$ T cells.

Figure 10C:
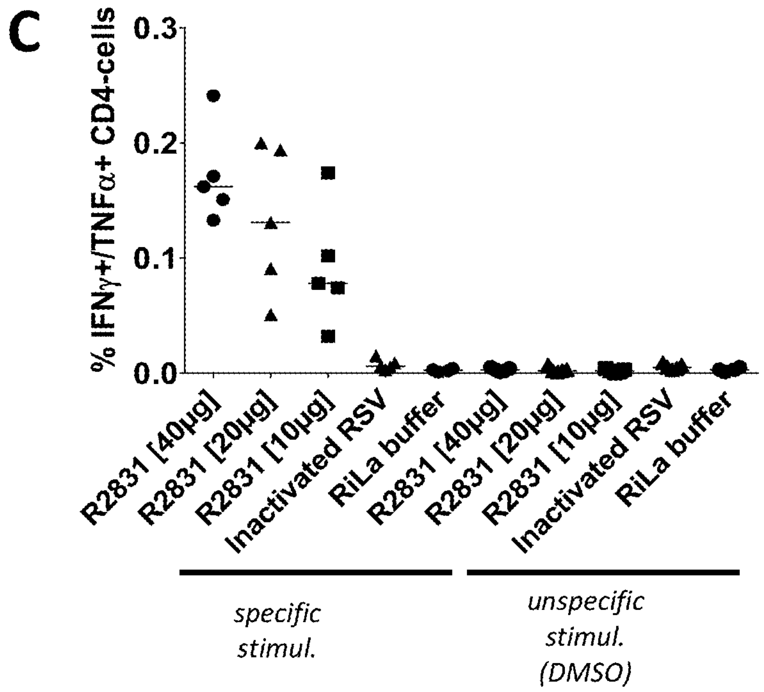

FIGS. 10A-C: show that the RSV-N mRNA vaccine (R2831) induces Nucleoprotein (N)-specific multifunctional $CD4^+$ T cells in mice.

The experiment was performed as described in Example 5 and T cells were analysed by intracellular cytokine staining for the antigen-specific induction of cytokines after stimulation with ProMix RSV-N (15mer peptides). The line in the graph represents the median value (n=5 mice/group).

As can be seen, the RSV-N mRNA vaccine induces RSV Nucleoprotein (N)-specific multifunctional $CD4^+$ T cells in contrast to the vaccine based on inactivated RSV which is not able to induce N protein-specific $CD4^+$ T cells.

Figure 11C:
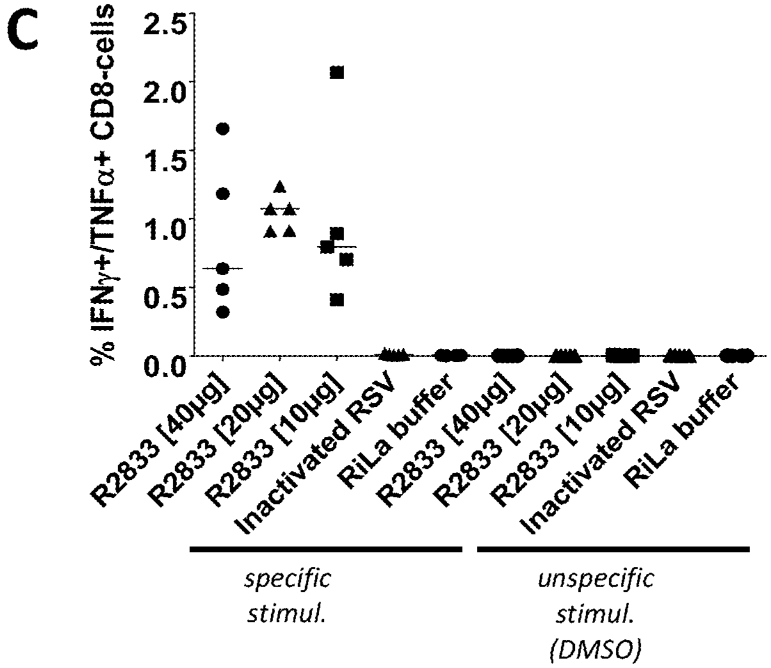

FIGS. 11A-C: show that the RSV-M2-1 mRNA vaccine (R2833) induces M2-1-specific multifunctional $CD8^+$ T cells in mice.

The experiment was performed as described in Example 5 and T cells were analysed by intracellular cytokine staining for the antigen-specific induction of cytokines after stimulation with a M2-1 specific 9mer peptide. The line in the graph represents the median value (n=5 mice/group).

As can be seen, the RSV-M2-1 mRNA vaccine induces RSV RSV-M2-1-specific multifunctional $CD8^+$ T cells in contrast to the vaccine based on inactivated RSV which is not able to induce M2-1 protein-specific $CD8^+$ T cells.

Figure 12:
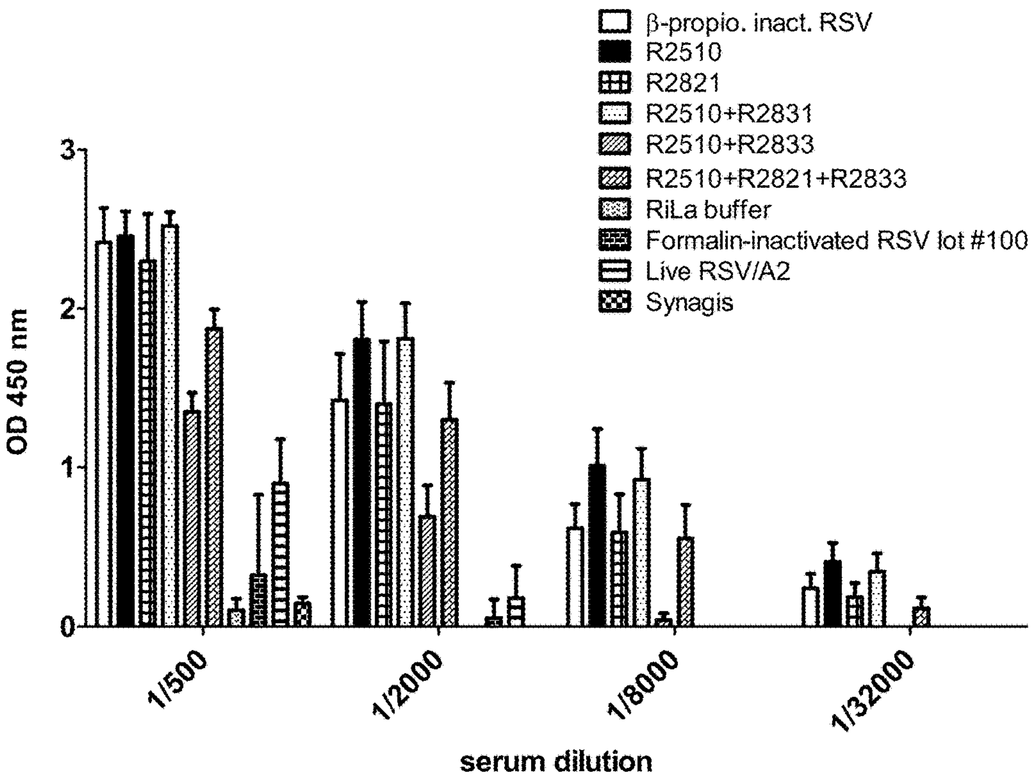

FIG. 12: shows that RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833) induce humoral immune responses in cotton rats.

The experiment was performed as described in Example 6 and RSV-F specific total IgG antibody titers were determined by ELISA on day 49. Serum was analyzed in different dilution, as given below the graph.

Figure 13:
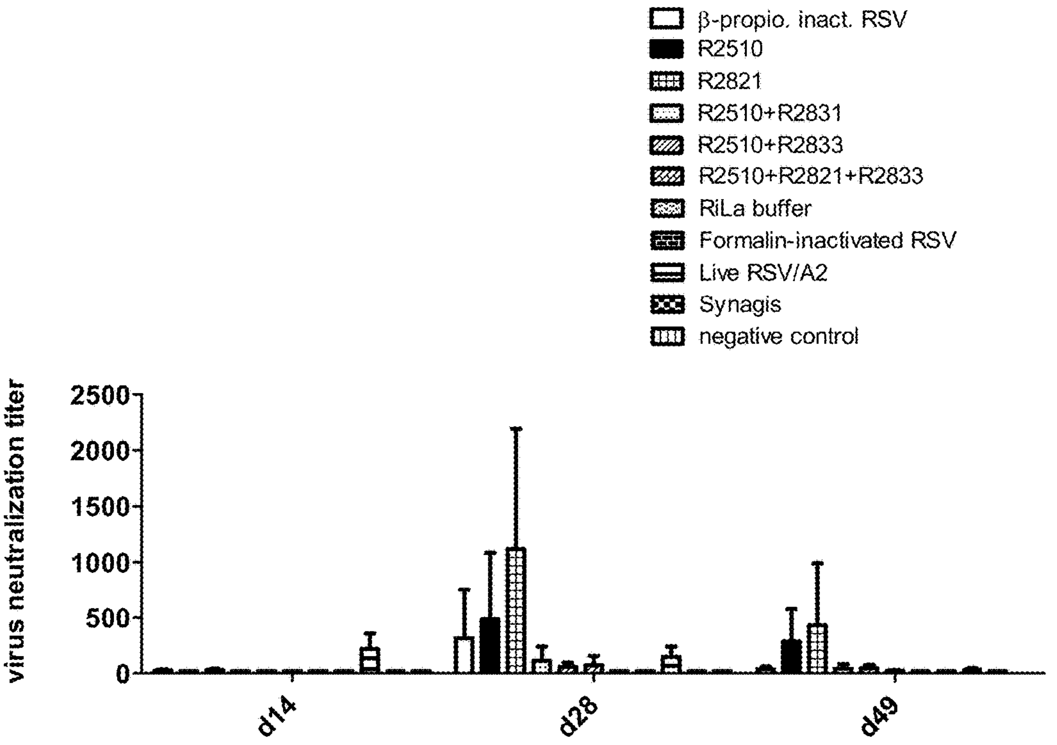

FIG. 13: shows that RSV-F mRNA vaccines either alone (RSV-F, R2510; RSV-Fdel554-574 mutant, R2821) or in combination with mRNAs encoding other RSV proteins (RSV-N=R2831; RSV-M2-1=R2833) induce the formation of functional antibodies in cotton rats as shown by virus neutralizing antibody titers.

The experiment was performed as described in Example 6 and virus neutralizing titers on day 49 were determined by plaque reduction assay.

FIGS. 14A-B: show that RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833) reduce lung and nasal titers in cotton rats challenged with RSV virus.

The experiment was performed as described in Example 6.

(A) Lung titers on day 5 after RSV challenge infection. All animal groups vaccinated with mRNA vaccines showed virus titers below the level of detection of the performed virus titration demonstrating protection of vaccinated cotton rats in terms of viral lung titers. In comparison to the mRNA vaccines the vaccine based on formalin-inactivated virus were not able to prevent virus titers in the lung.

(B) Nasal titers on day 5 after RSV challenge infection. The viral titer in the nasal tissue was also strongly reduced in groups vaccinated with mRNA. In comparison to the mRNA vaccines the vaccine based on formalin-inactivated virus were not able to reduce the nasal virus titers.

Figure 15:
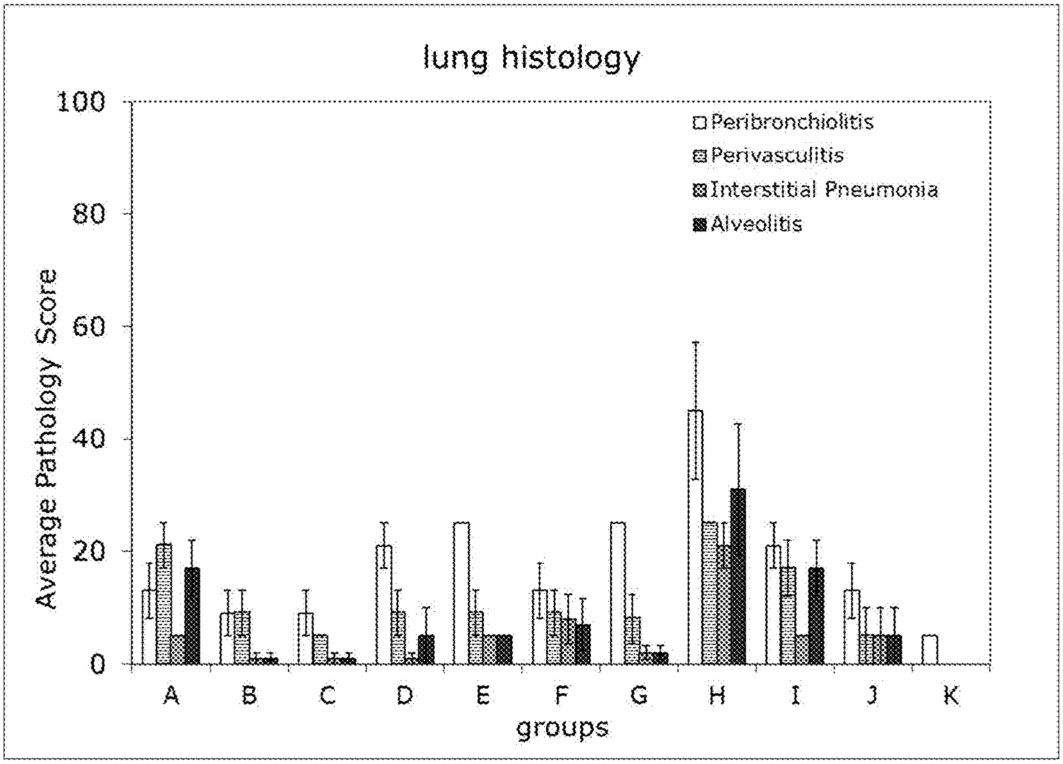

FIG. 15: shows the results of the lung histopathology analysis from the RSV cotton rat challenge study described in Example 6.

FIGS. 16A-D: show the results of the quantitative reverse transcription polymerase chain reaction (RT-PCR) of viral genome copy numbers (by measuring copy numbers of the RSV NS-1 gene) or expressed cytokines from lung tissue of the RSV infected animals (or controls) of the RSV cotton rat challenge study described in Example 6.

FIGS. 17A-B: show that RSV-F mRNA vaccines (RSV-F=R2510; RSV F* (RSV-Fde1554-574 mutant)=R2821) reduce lung titers in cotton rats challenged with RSV virus. The experiment was performed as described in Example 7.

(A) Lung titers on day 5 after RSV challenge infection. All animal groups vaccinated intradermally with mRNA vaccines showed reduced virus titers compared to the buffer control group demonstrating protection of vaccinated cotton rats in terms of viral lung titers. Already one single dose of RSV-F mRNA vaccines efficiently reduced viral titers in the lung.

(B) Lung titers on day 5 after RSV challenge infection. The viral titer in the lung was also strongly reduced in groups intramuscularly vaccinated with mRNA.

EXAMPLES

The examples shown in the following are merely illustrative and shall describe the present invention in a further way. These examples shall not be construed to limit the present invention thereto.

Example 1: Preparation of the mRNA Vaccine

1. Preparation of DNA and mRNA Constructs

For the present examples DNA sequences, encoding the RSV-F protein (R1691 and R2510), the RSV-F del554-574 (R2821) mutant protein, the RSV N-protein (R2831) and the RSV M2-1 protein (R2833) of the RSV long strain were prepared and used for subsequent in vitro transcription reactions. The RSV-Fde1554-574 mutant protein has been described previously (Oomens et al. 2006. J. Virol. 80(21): 10465-77).

According to a first preparation, the DNA sequences coding for the above mentioned mRNAs were prepared. The construct R1691 was prepared by modifying the wild type coding sequence by introducing a GC-optimized sequence for stabilization, followed by a stabilizing sequence derived from the alpha-globin-3'-UTR (muag (mutated alpha-globin-3'-UTR) according to SEQ ID No. 29), a stretch of 64 adenosines (poly(A)-sequence), a stretch of 30 cytosines (poly(C)-sequence), and a histone stem loop according to SEQ ID No. 30. In SEQ ID NO: 31 (see FIG. 1) the sequence of the corresponding mRNA is shown. The constructs R2510, R2821, R2831 and R2833 were prepared by introducing a 5'-TOP-UTR derived from the ribosomal protein 32L according to SEQ ID No. 23, modifying the wild type coding sequence by introducing a GC-optimized sequence for stabilization, followed by a stabilizing sequence derived from the albumin-3'-UTR (albumin7 according to SEQ ID No. 25), a stretch of 64 adenosines (poly(A)-sequence), a stretch of 30 cytosines (poly(C)-sequence), and a histone stem loop according to SEQ ID No. 30. In SEQ ID NOs: 32-35 (see FIG. 2-5) the sequences of the corresponding mRNAs are shown.

TABLE 1

| mRNA constructs | | | |
|---|---|---|---|
| RNA | Antigen | FIG. | SEQ ID NO. |
| R1691 | RSV F | 1 | SEQ ID NO. 31 |
| R2510 | RSV F | 2 | SEQ ID NO. 32 |
| R2821 | RSV Fdel554-574 | 3 | SEQ ID NO. 33 |
| R2831 | RSV N | 4 | SEQ ID NO. 34 |
| R2833 | RSV $M_{2-1}$ | 5 | SEQ ID NO. 35 |

2. In Vitro Transcription

The respective DNA plasmids prepared according to paragraph 1 were transcribed in vitro using T7 polymerase in the presence of a CAP analog ($m^7GpppG$). Subsequently the mRNA was purified using PureMessenger® (CureVac, Tubingen, Germany; WO2008/077592A1).

3. Reagents

Complexation Reagent: protamine

4. Preparation of the Vaccine

The mRNA was complexed with protamine by addition of protamine to the mRNA in the ratio (1:2) (w/w) (adjuvant component). After incubation for 10 minutes, the same amount of free mRNA used as antigen-providing RNA was added.

For example: RSV-F long vaccine (R1691): comprising an adjuvant component consisting of mRNA coding for RSV F protein long (R1691) according to SEQ ID NO. 31 complexed with protamine in a ratio of 2:1 (w/w) and the antigen-providing free mRNA coding for RSV F protein long (R1691) according to SEQ ID NO. 31 (ratio 1:1; complexed RNA:free RNA).

Example 2: Induction of a Humoral Immune Response by the RSV-F Long mRNA Vaccine in Mice Immunization On day zero, BALB/c mice were intradermally (i.d.) injected with the RSV-F long mRNA vaccine (R1691 according to Example 1; 25 μg/mouse/vaccination day) or Ringer-lactate (RiLa) as buffer control as shown in Table 2. A control group was intramuscularly (i.m.) injected with 10 μg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 μg/μL was achieved. All animals received boost injections on day 14 and day 28. Blood samples were collected on day 42 for the determination of anti-RSV F antibody titers.

TABLE 2

| Animal groups | | | | | |
|---|---|---|---|---|---|
| Group | Strain sex | No. mice | Route volume | Vaccine dose | Vaccination schedule |
| 1 | BALB/c Female | 5 | i.d. 2 × 50 µl | R1691 2 µg | d0: prime, d14: boost, d28: boost, d42: blood collection |
| 2 | BALB/c Female | 5 | i.m. 2 × 25 µl | Inactivated RSV long 10 µg | d0: prime, d14: boost, d28: boost, d42: blood collection |
| 3 | BALB/c Female | 5 | i.d. 2 × 50 µl | 80% Ringer Lactate (RiLa) buffer | d0: prime, d14: boost, d28: boost, d42: blood collection |

Determination of Anti-RSV F Protein Antibodies by ELISA

ELISA plates are coated with recombinant human RSV fusion glycoprotein (rec.hu F-protein, final conc.: 5 µg/mL) (Sino Biological Inc.). Coated plates are incubated using given serum dilutions and binding of specific antibodies to the F protein is detected using biotinylated isotype specific anti-mouse antibodies in combination with streptavidin-HRP (horse radish peroxidase) with ABTS substrate.

Results

Figure 6C:
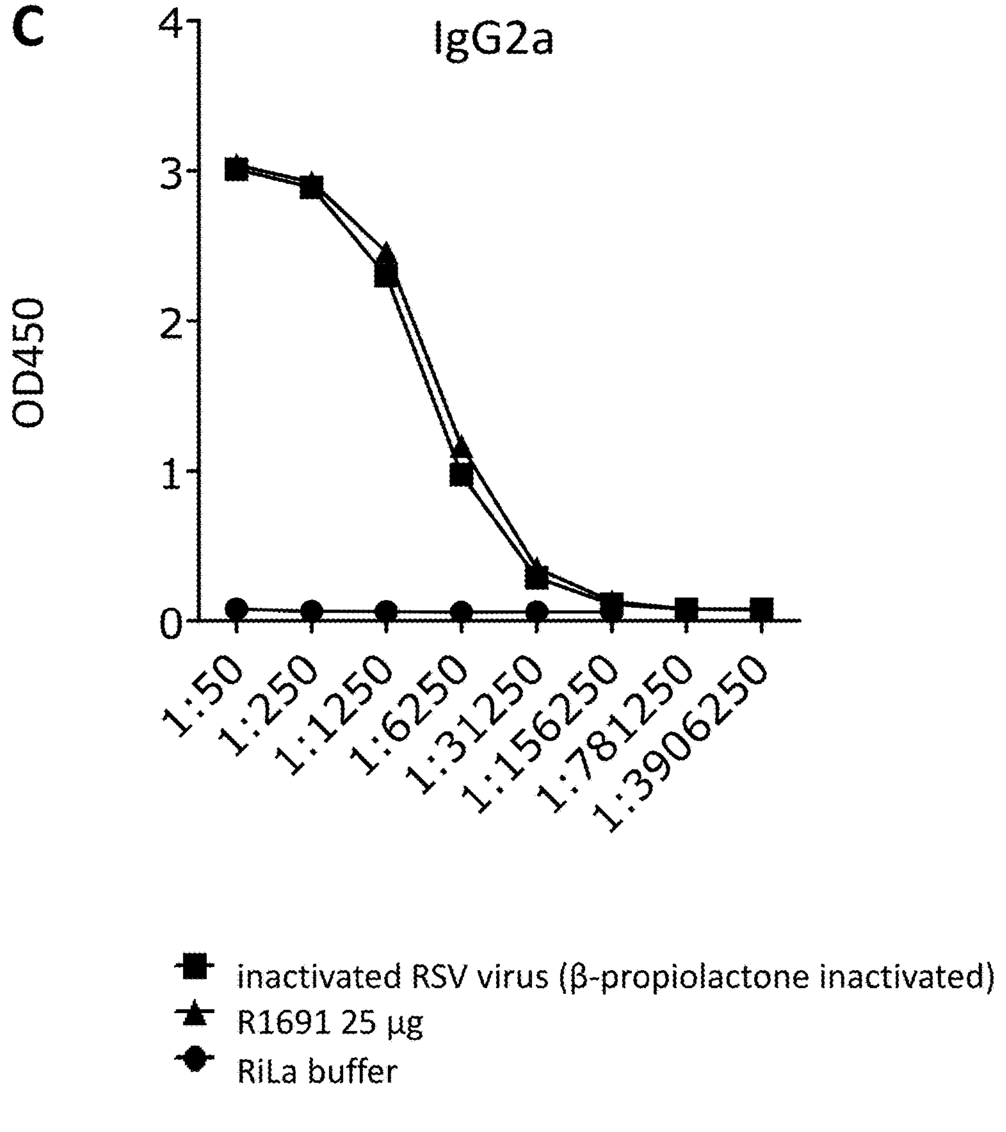

As can be seen in FIG. 6, the RSV-F long mRNA vaccine induces antibody titers (total IgG, IgG1 and IgG2a) against the RSV F protein comparable to those against inactivated RSV.

Example 3: Induction of a Long-Lived Humoral Immune Response by the RSV-F Long mRNA Vaccine in Mice Immunization BALB/c mice were intradermally (i.d.) injected with 20 µg of the RSV-F long mRNA vaccine (R1691) or Ringer Lactate (RiLa) buffer according to the vaccination schedule shown in Table 3. Blood was collected 2 weeks, 4 months and 11 months after the last immunization.

TABLE 3

| Animal groups | | | | | |
|---|---|---|---|---|---|
| Group | Strain sex | Number of mice | Route volume | Vaccine dose | Vaccination schedule (day) |
| 1 | BALB/c Female | 5 | i.d. 100 µl | R1691 20 µg | d0, d14, d28 |
| 4 | BALB/c Female | 5 | i.d. 100 µl | 80% RiLa buffer | d0, d14, d28 |

Results

As can be seen in FIG. 7, the RSV-F long mRNA vaccine induced a long-lived immune response as demonstrated by stable antibody titers for at least 11 months after the last boost vaccination.

Example 4: Induction of a Cellular Immune Response by the RSV-F Long mRNA Vaccine in Mice Immunization On day zero, BALB/c mice were intradermally (i.d.) injected with the RSV-F long mRNA vaccine R1691 (20 µg/mouse/vaccination day) or Ringer-lactate (RiLa) as buffer control as shown in Table 4. A control group was intramuscularly (i.m.) injected with 10 µg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 µg/µL was achieved.

All animals received boost injections on days 14 and 28. Spleens were collected on day 34 for the analysis of antigen-specific T cells.

TABLE 4

| Animal groups | | | | | |
|---|---|---|---|---|---|
| Group | Strain sex | Number of mice | Route volume | Vaccine dose | Vaccination schedule |
| 1 | BALB/c Female | 5 | i.d. 2 × 50 µl | R1691 20 µg | d0: prime, d14: boost, d28: boost, d34: spleen collection |
| 2 | BALB/c Female | 5 | i.m. 2 × 25 µl | Inactivated RSV long 10 µg | d0: prime, d14: boost, d28: boost, d34: spleen collection |
| 0 | BALB/c Female | 5 | i.d. 2 × 50 µl | Ringer Lactate (RiLa) buffer | d0: prime, d14: boost, d28: boost, d34: spleen collection |

Intracellular Cytokine Staining

Splenocytes from vaccinated and control mice were isolated according to a standard protocol. Briefly, isolated spleens were grinded through a cell strainer and washed in PBS/1% FBS followed by red blood cell lysis. After an extensive washing step with PBS/1% FBS splenocytes were seeded into 96-well plates ($2\times10^6$ cells/well). The next day cells were stimulated with a RSV-F peptide (KYKNAVTEL; 5 µg/ml; H-2kd-restructed T-cell epitope) or an irrelevant control peptide derived from the influenza HA protein (IYSTVASSL; 5 µg/ml; purchased from EMC Microcollections) and 2.5 µg/ml of an anti-CD28 antibody (BD Biosciences) for 6 hours at 37° C. in the presence of the mixture of GolgiPlug™/GolgiStop™ (Protein transport inhibitors containing Brefeldin A and Monensin, respectively; BD Biosciences). After stimulation cells were washed and stained for intracellular cytokines using the Cytofix/Cytoperm reagent (BD Biosciences) according to the manufacturer's instructions. The following antibodies were used for staining: CD8-PECy7 (1:200), CD3-FITC (1:200), IL2-PerCP-Cy5.5 (1:100), TNFα-PE (1:100), IFNγ-APC (1:100) (eBioscience), CD4-BD Horizon V450 (1:200) (BD Biosciences) and incubated with Fcγ-block diluted 1:100. Aqua Dye was used to distinguish live/dead cells (Invitrogen). Cells were collected using a Canto II flow cytometer (Beckton Dickinson). Flow cytometry data were analysed using FlowJo software (Tree Star, Inc.). Statistical analysis was performed using GraphPad Prism software, Version 5.01. Statistical differences between groups were assessed by the Mann Whitney test.

Results

As can be seen from FIG. 8, the RSV-F long mRNA vaccine (R1691) induced IFNγ positive, TNFα positive and IFNγ/TNFα double-positive multifunctional $CD8^+$ T cells directed against RSV F protein. Surprisingly the vaccine based on inactivated RSV virus was not able to induce antigen-specific $CD8^+$ T cells.

Example 5: Induction of Cellular Immune Responses by the RSV-N and RSV-$M_{2-1}$ mRNA Vaccines in Mice Immunization On day zero, BALB/c mice were intradermally (i.d.) injected with different doses of the RSV-N mRNA vaccine R2831, the RSV-M2-1 mRNA vaccine R2833 or Ringer-lactate (RiLa) as buffer control as shown in Table 5. A control group was intramuscularly (i.m.) injected with 10 μg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 μg/μL was achieved. All animals received boost injections on days 7 and 21. Spleens were collected on day 27 for the analysis of antigen-specific T cells.

TABLE 5

| Animal groups | | | | | |
|---|---|---|---|---|---|
| Group | Strain sex | No. mice | Route volume | Vaccine dose | Vaccination schedule |
| 1 | BALB/c Female | 5 | i.d. 1 × 50 μl | R2831 RSV-N 40 μg | d0: prime, d7: boost, d21: boost, d27: spleen collection |
| 2 | BALB/c Female | 5 | i.d. 1 × 25 μl | R2831 RSV-N 20 μg | d0: prime, d7: boost, d21: boost, d27: spleen collection |
| 3 | BALB/c Female | 5 | i.d. 1 × 12.5 μl | R2831 RSV-N 10 μg | d0: prime, d7: boost, d21: boost, d27: spleen collection |
| 4 | BALB/c Female | 5 | i.d. 1 × 50 μl | R2833 RSV-$M_{2-1}$ 40 μg | d0: prime, d7: boost, d21: boost, d27: spleen collection |
| 5 | BALB/c Female | 5 | i.d. 1 × 25 μl | R2833 RSV-$M_{2-1}$ 20 μg | d0: prime, d7: boost, d21: boost, d27: spleen collection |
| 6 | BALB/c Female | 5 | i.d. 1 × 12.5 μl | R2833 RSV-$M_{2-1}$ 10 μg | d0: prime, d7: boost, d21: boost, d27: spleen collection |
| 7 | BALB/c Female | 5 | i.m. 2 × 25 μl | Inactiv. RSV long 10 μg | d0: prime, d7: boost, d21: boost, d27: spleen collection |

TABLE 5-continued

| Animal groups | | | | | |
|---|---|---|---|---|---|
| Group | Strain sex | No. mice | Route volume | Vaccine dose | Vaccination schedule |
| 8 | BALB/c Female | 5 | i.d. 1 × 50 μl | 100% RiLa buffer | d0: prime, d7: boost, d21: boost, d27: spleen collection |

Intracellular cytokine staining was performed as described in Example 4 except that cells were treated with the following stimulators at:

M2-1 peptide (5 μg/ml) group 4 to 8; (SYIGSINNI from Proimmune); ProMix N (1 μg/ml) 1-3, group 7 and 8; (PX39 from Proimmune); control: medium+DMSO+anti-CD28, group 1-8 as descripted above.

Results

As can be seen from FIG. 9, the RSV-N mRNA vaccine (R2831) induced IFNγ positive, TNFα positive and IFNγ/TNFα double-positive multifunctional $CD8^+$ T cells directed against RSV N protein in mice.

Surprisingly the vaccine based on inactivated RSV virus was not able to induce antigen-specific $CD8^+$ T cells.

As can be seen from FIG. 10, the RSV-N mRNA vaccine (R2831) induced IFNγ positive, TNFα positive and IFNγ/TNFα double-positive multifunctional $CD4^+$ T cells directed against RSV N protein in mice.

Surprisingly the vaccine based on inactivated RSV virus was not able to induce antigen-specific $CD4^+$ T cells.

As can be seen from FIG. 11, the RSV-M2-1 mRNA vaccine (R2833) induced IFNγ positive, TNFα positive and IFNγ/TNFα double-positive multifunctional $CD8^+$ T cells directed against RSV M2-1 protein in mice.

Surprisingly the vaccine based on inactivated RSV virus was not able to induce antigen-specific $CD8^+$ T cells.

Example 6: RSV Cotton Rat Challenge Study I

For the development of RSV vaccines the cotton rat is an accepted animal model, especially for the challenge infection. Cotton rats respond to formalin-inactivated RSV virus vaccine preparations with enhanced lung pathology. This allows the evaluation of the safety of a vaccination in terms of enhanced disease phenomenon.

To broaden and optimize the RSV-specific immune response, mRNA vaccines encoding different RSV proteins (RSV F, mutant RSV-Fdel554-574, N and M2-1) were prepared according to Example 1. In order to assess the effect of single or combined vaccines, these vaccines were administered either alone or in combination (cocktail vaccine) as shown in Table 5. Vaccine volumes of 2×50 μl were injected intradermally (i.d.) into the back skin of cotton rats. Additional groups were immunized intramuscularly (i.m.) with β-propiolactone inactivated RSV (INSTITUT VIRION/SERION GmbH-SERION IMMUNDIAGNOSTICA GmbH), formalin-inactivated RSV (Sigmovir) or live RSV/A2 (Sigmovir) ($10^5$ plaque forming units, pfu) to compare their immunogenicity to mRNA vaccines. Another group received i.m. injections of the monoclonal anti-RSV antibody SYNAGIS® (Palivizumab) as passive immunization. SYNAGIS® was administered with a dose of 15 mg/kg on the day prior to RSV challenge infection. Therefore the animals were weighed and the appropriate amount of SYNAGIS® was calculated according to the animals' weight. The maximal volume for i.m. injection was 200 μl per 100 g rat. After immunization the cotton rats were challenged by intranasal (i.n.) infection with RSV/A2 virus ($10^5$ PFU in 100 μl; Sigmovir).

TABLE 5

| Animal groups | | | | | | | | |
|---|---|---|---|---|---|---|---|---|
| Groups | Vaccine dose | Volume | Antigen | Route | # of adminis-trations | N per group | Vaccination (day) | Bleed (day) |
| A | β-propiolactone inactivated RSV 20 μg | 100 μl | — | IM | 3 | 5 | 0, 14, 28 | 14, 28, 49 |
| B | R2510 80 μg | 2 × 50 μl | RSV F | ID | 3 | 5 | 0, 14, 28 | 14, 28, 49 |
| C | R2821 80 μg | 2 × 50 μl | RSV F mutant | ID | 3 | 5 | 0, 14, 28 | 14, 28, 49 |
| D | R2510 + R2831 "cocktail I" each 40 μg | 2 × 50 μl | RSV F + RSV N | ID | 3 | 5 | 0, 14, 28 | 14, 28, 49 |
| E | R2510 + R2833 "cocktail II" each 40 μg | 2 × 50 μl | RSV F + RSV $M_{2-1}$ | ID | 3 | 5 | 0, 14, 28 | 14, 28, 49 |
| F | R2510 + R2831 + R2833 "cocktail III" each 26.666 μg | 2 × 50 μl | RSV F + RSV $M_{2-1}$ + RSV N | ID | 3 | 5 | 0, 14, 28 | 14, 28, 49 |
| G | RiLa | 2 × 50 μl | — | ID | 3 | 5 | 0, 14, 28 | 14, 28, 49 |
| H | FI-RSV Lot#100 (diluted 1:100 in PBS) | 100 μl | — | IM | 2 | 5 | 0, 28 | 28, 49 |
| I | Live RSV/A2 $10^5$ pfu | 100 μl | — | IM | 1 | 5 | 0 | 49 |
| J | SYNAGIS ® (15 mg/kg) | | — | IM | 1 | 5 | 48 | 49 |
| K | Neg. control | | — | N/A | N/A | 5 | — | — |

The following assays were performed to analyze the immune responses: RSV F-protein serum IgG ELISA, RSV virus neutralizing antibody titers (VNT), RSV viral titrations and pulmonary histopathology.

RSV F-Protein Serum IgG ELISA

The induction of anti-RSV F protein antibodies were determined by ELISA according to Example 2.

RSV Virus Neutralizing Antibody Titers (VNT)

Sera were analysed by the virus neutralization test (VNT). Briefly, sera samples were diluted 1:10 with EMEM, heat inactivated and serially diluted further 1:4. Diluted sera samples were incubated with RSV (25-50 PFU) for 1 hour at room temperature and inoculated in duplicates onto confluent HEp-2 monolayers in 24 well plates. After one hour incubation at 37° C. in a 5% $CO_2$ incubator, the wells were overlayed with 0.75% Methylcellulose medium. After 4 days of incubation, the overlay was removed and the cells were fixed with 0.1% crystal violet stain for one hour and then rinsed and air dried. The corresponding reciprocal neutralizing antibody titers were determined at the 60% reduction end-point of the virus control.

RSV Viral Titrations and Pulmonary Histopathology

On day 54 nasal tissue was harvested and homogenized for viral titrations. The lung was harvested en bloc and tri-sected for viral titration (left section), histopathology (right section), and PCR analysis (lingular lobe). In addition, RSV viral genome copy numbers (by measuring copy numbers of the RSV NS-1 gene) and cytokine mRNA levels were determined by quantitative reverse transcription polymerase chain reaction (qRT-PCR).

Results

As can be seen from FIG. 12, the RSV-F mRNA vaccines either alone (RSV-F=R2510; RSV-Fde1554-574 mutant=R2821) or in combination with mRNAs encoding other RSV proteins (RSV-N=R2831; RSV-M2-1=R2833), induce RSV F specific humoral immune responses in cotton rats as shown by total IgG antibody titers on day 49.

As can be seen from FIG. 13, the RSV-F mRNA vaccines either alone (RSV-F=R2510; RSV-Fde1554-574 mutant=R2821) or in combination with mRNAs encoding other RSV proteins (RSV-N, R2831=RSV-M2-1=R2833), induce the formation of RSV specific functional antibodies in cotton rats as shown by virus neutralizing antibody titers.

As can be seen from FIG. 14, the RSV-F mRNA vaccines either alone (RSV-F=R2510; RSV-Fde1554-574 mutant=R2821) or in combination with mRNAs encoding other RSV proteins (RSV-N=R2831; RSV-M2-1=R2833), reduce lung and nasal viral titers in cotton rats challenged with RSV virus.

As can be seen in FIG. 14A, all animal groups vaccinated with mRNA vaccines showed virus titers below the level of detection of the performed virus titration demonstrating protection of vaccinated cotton rats in terms of viral lung titers. By contrast, the Formalin-inactivated virus vaccine reduced only minimally the lung virus titer compared to the RiLa buffer control group. The effect of the β-propiolactone inactivated RSV vaccine was more pronounced but did not reduce the virus lung titer below the detection level in all animals of this group. As can be seen in FIG. 14B, the viral titer in the nasal tissue was also strongly reduced in groups vaccinated with mRNA. Nasal viral titers of the Formalin-inactivated virus were comparable to the viral titer in the RiLa vaccinated group. The β-propiolactone inactivated virus vaccine was more effective (at least for two of five animals). In contrast thereto, all mRNA vaccinated groups had reduced nasal virus titer compared to RiLa vaccinated group.

As can be seen from FIG. 15, the lung histopathology analysis from the RSV cotton rat challenge study reveals different pathology scores for the various animal groups.

From the histopathology it can be concluded that none of the mRNA vaccinated groups displayed enhanced lung pathology as it is the case for the group that was vaccinated using the Formalin-inactivated RSV vaccine. The average pathology scores for peribronchiolitis (PB), perivasculitis (PV), insterstitial pneumonia (IP) and alveolitis (A) are much lower for all groups vaccinated with mRNA compared to group H (Formalin-inactivated RSV). In addition the groups being vaccinated with R2510 (group B; RSV F) or R2821 (group C; RSV F mutant) seem to exhibit reduced lung pathology compared to the RiLa buffer vaccinated and subsequently RSV infected group (G).

As can be seen in FIG. 16, the quantitative RT-PCR reveals different expression patterns for the various animal groups. The quantification of RSV genome copies by measuring the RSV NS-1 gene is displayed in A. Genome copy numbers are reduced by vaccination using mRNA vaccines compared to the RiLa buffer control (group G). This is not the case for the group that was vaccinated using formalin-inactivated-RSV (group H). As it is shown in B, the vaccination using the formalin-inactivated-RSV vaccine (group H) induces enhanced expression of the TH2 cytokine IL-4 compared to the control group that was vaccinated with RiLa buffer (group G). By contrast, the vaccination with mRNA R2821 encoding the RSV-F mutant significantly reduced IL-4 mRNA expression compared to the RiLa control group in the lung after RSV challenge infection. C. Expression of INF-γ□mRNA. D. Expression of IL-5 mRNA. The expression of IL-5 is significant reduced in groups vaccinated using R2510 or R2821 compared to RiLa buffer vaccinated animals. The expression of the viral NS-1 RNA or cytokine mRNAs, which were isolated from lung tissue, is measured on day 5 post-challenge. The statistical analysis was performed with the student T-test (* $p<0.05$ when compared to group G (RiLa control)).

Example 7: RSV Cotton Rat Challenge Study II mRNA vaccines encoding RSV F protein (F) or mutant RSV-F protein (F*) (RSV F del554-574) were prepared according to Example 1. In order to assess the effect of single or several vaccinations (prime and boost vaccinations), these vaccines were administered once, twice or 3 times (as shown in Table 6). Vaccine volumes of 2×50 μl were injected intradermally (i.d.) into the back skin of cotton rats. Additional groups were immunized intramuscularly (i.m.) with vaccine volumes of 1×100 μl into the right hind leg. As a control, one group was injected intradermally with Ringer-Lactate buffer (buffer). After immunization, the cotton rats were challenged by intranasal (i.n.) infection with RSV/A2 virus ($10^5$ PFU in 100 μl; Sigmovir). As a control, one group was not treated and remained unchallenged with virus (untreated).

TABLE 5

| Animal groups | | | | | | | | |
|---|---|---|---|---|---|---|---|---|
| Groups | Vaccine dose | Volume | Antigen | Route | # of adminis-trations | N per group | Vaccination (day) | Challenge (day) |
| F* i.d. 3x | R2821 80 μg | 2 × 50 μl | RSV F mutant | ID | 3 | 5 | 0, 14, 28 | 49 |
| F* i.d. 2x | R2821 80 μg | 2 × 50 μl | RSV F mutant | ID | 2 | 5 | 0, 14 | 49 |
| F* i.d. 1x | R2821 80 μg | 2 × 50 μl | RSV F mutant | ID | 1 | 5 | 0 | 49 |
| F i.d. 3x | R2510 80 μg | 2 × 50 μl | RSV F | ID | 3 | 5 | 0, 14, 28 | 49 |
| F i.d. 2x | R2510 80 μg | 2 × 50 μl | RSV F | ID | 2 | 5 | 0, 14 | 49 |
| F i.d. 1x | R2510 80 μg | 2 × 50 μl | RSV F | ID | 1 | 5 | 0 | 49 |
| F* i.m. | R2821 80 μg | 1 × 100 μl | RSV F mutant | IM | 2 | 5 | 0, 14 | 49 |
| F i.m. | R2510 80 μg | 1 × 100 μl | RSV F | IM | 2 | 5 | 0, 14 | 49 |
| Buffer | — | 2 × 50 μl | | ID | 3 | 5 | 0, 14, 28 | 49 |
| untreated | — | | — | N/A | N/A | 5 | — | — |

RSV Viral Titrations

The determination of RSV viral titers was conducted as described in Example 6.

Results

As shown in FIG. 17A, already one single intradermal vaccination with mRNA vaccines coding for RSV F protein (F) or mutant RSV-F protein (F*) (RSV F del554-574) was highly efficient in reducing the viral titer in the lung compared to the buffer control group. A second and third vaccination (“boost vaccinations) reduced the viral titers below detection level.

As shown in FIG. 17B, already two intramuscular vaccinations with mRNA vaccines coding for RSV F protein (F) or mutant RSV-F protein (F*) (RSV F del554-574) strongly reduced the viral titer in the lung compared to the buffer control group.

The invention claimed is:

1. A method of treatment or prophylaxis of Respiratory syncytial virus (RSV) infections comprising the steps:

a) providing an mRNA sequence encoding at least one antigenic polypeptide from the fusion protein F, the nucleoprotein N, the M2-1 protein, or the M2-2 protein of RSV, wherein the G/C content of the sequence encoding the antigenic polypeptide is increased compared with the G/C content of the coding region of the wild type mRNA encoding the antigenic polypeptide; and b) applying or administering the mRNA sequence to a subject, wherein the polypeptide coding sequence of the mRNA sequence encoding the antigenic polypeptide comprises a sequence at least 90% identical to the polypeptide coding sequence of SEQ ID NO: 31, 32, 33, 34 or 35.

2. The method according to claim 1, wherein the mRNA further comprises a 5'-cap structure, a poly(A) sequence, and/or a poly(C) sequence.

3. The method according to claim 2, wherein the 5'cap structure is m7GpppN.

4. The method according to claim 2, wherein the poly(A) sequence comprises a sequence of 25 to 400 adenosine nucleotides.

5. The method according to claim 1, wherein the mRNA further comprises at least one histone stem-loop.

6. The method according to claim 1, wherein the mRNA sequence further comprises a stabilizing sequence from the alpha globin 3' UTR, positioned 3' relative to the polypeptide coding region of the mRNA sequence.

7. The method according to claim 1, wherein the mRNA sequence comprises from a 5' to 3': a 5'-cap structure, a 5' UTR sequence, the sequence encoding the at least one antigenic polypeptide, a 3' UTR, a poly(A) sequence, a poly(C) sequence and a histone stem-loop sequence.

8. The method according to claim 1, wherein the at least one antigenic polypeptide is from the RSV fusion protein F.

9. The method according to claim 1, wherein the mRNA sequence is complexed with a cationic or polycationic compound.

10. The method according to claim 9, wherein the cationic or polycationic compound is protamine, poly-L-lysine (PLL), or poly-arginine.

11. The method according to claim 9, wherein the cationic or polycationic compound is protamine.

12. The method according to claim 9, wherein the weight ratio of the mRNA sequence to the cationic or polycationic compound is in the range from 6:1 to 0.25:1.

13. The method of claim 1, wherein the mRNA sequence is administered by injection.

14. The method of claim 13, wherein the mRNA sequence is administered by intradermal or intramuscular injection.

15. The method of claim 1, wherein the mRNA sequence is formulated in a Ringer's lactate solution.

16. The method of claim 1, further comprising administering mRNA sequences encoding at least 2 different antigenic polypeptides from RSV.

17. The method of claim 16, wherein the mRNA sequences encoding the at least 2 different antigenic polypeptides are administered separately.

18. The method of claim 16, wherein the mRNA sequences encoding the at least 2 different antigenic polypeptides are administered in the same formulation.

19. The method according to claim 1, wherein the polypeptide coding sequence of the mRNA sequence encoding the antigenic polypeptide comprises a sequence at least 95% identical to the polypeptide coding sequence of SEQ ID NO: 31, 32, 33, 34 or 35.

20. The method according to claim 1, wherein the polypeptide coding sequence of the mRNA sequence encoding the antigenic polypeptide comprises a sequence according to the polypeptide coding sequence of SEQ ID NO: 31, 32, 33, 34 or 35.

21. The method of claim 1, further defined as a method for inducing an RSV-specific T-cell response in the subject.

* * * * *

SEQUENCE LISTING

<160> NUMBER OF SEQ ID NOS: 37

<210> SEQ ID NO 1
<211> LENGTH: 574
<212> TYPE: PRT
<213> ORGANISM: respiratory syncytial virus

<400> SEQUENCE: 1

Met Glu Leu Pro Ile Leu Lys Ala Asn Ala Ile Thr Thr Ile Leu Ala
1 5 10 15

Ala Val Thr Phe Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Asn
65 70 75 80

Gln Glu Leu Asp Lys Tyr Lys Asn Ala Val Thr Glu Leu Gln Leu Leu
85 90 95

Met Gln Ser Thr Thr Ala Ala Asn Asn Arg Ala Arg Arg Glu Leu Pro
100 105 110

Arg Phe Met Asn Tyr Thr Leu Asn Asn Thr Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Ile Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Arg Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Ser Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Glu Thr Cys Lys Val Gln Ser Asn Arg Val Phe Cys Asp
355 360 365

-continued

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His His Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 2
<211> LENGTH: 298
<212> TYPE: PRT
<213> ORGANISM: respiratory syncytial virus

<400> SEQUENCE: 2

```
Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175
```

```
Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295


<210> SEQ ID NO 3
<211> LENGTH: 64
<212> TYPE: PRT
<213> ORGANISM: respiratory syncytial virus

<400> SEQUENCE: 3

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
            20                  25                  30

Ile Ile Ser Ile Met Thr Ala Ile Leu Asn Lys Leu Cys Glu Tyr Asn
        35                  40                  45

Val Phe His Asn Lys Thr Phe Glu Leu Pro Arg Ala Arg Val Asn Thr
    50                  55                  60


<210> SEQ ID NO 4
<211> LENGTH: 256
<212> TYPE: PRT
<213> ORGANISM: respiratory syncytial virus

<400> SEQUENCE: 4

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Leu
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140
```

-continued

```
Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 5
<211> LENGTH: 391
<212> TYPE: PRT
<213> ORGANISM: respiratory syncytial virus

<400> SEQUENCE: 5

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys His Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
```

```
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390


<210> SEQ ID NO 6
<211> LENGTH: 2165
<212> TYPE: PRT
<213> ORGANISM: respiratory syncytial virus

<400> SEQUENCE: 6

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Leu Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Ile Leu Ile Asp Asn Gln Thr Leu Ser
225                 230                 235                 240
```

-continued

```
Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Val Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
```

-continued

```
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Arg Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Val Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg  Thr Pro Asp Phe Leu  Thr Glu Ala
        995                 1000                1005

Ile Val  His Ser Val Phe Ile  Leu Ser Tyr Tyr Thr  Asn His Asp
    1010                1015                1020

Leu Lys  Asp Lys Leu Gln Asp  Leu Ser Asp Asp Arg  Leu Asn Lys
    1025                1030                1035

Phe Leu  Thr Cys Ile Ile Thr  Phe Asp Lys Asn Pro  Asn Ala Glu
    1040                1045                1050

Phe Val  Thr Leu Met Arg Asp  Pro Gln Ala Leu Gly  Ser Glu Arg
    1055                1060                1065

Gln Ala  Lys Ile Thr Ser Glu  Ile Asn Arg Leu Ala  Val Thr Glu
    1070                1075                1080
```

```
Val Leu  Ser Thr Ala Pro Asn  Lys Ile Phe Ser Lys  Ser Ala Gln
    1085                 1090                 1095

His Tyr  Thr Thr Thr Glu Ile  Asp Leu Asn Asp Ile  Met Gln Asn
    1100                 1105                 1110

Ile Glu  Pro Thr Tyr Pro His  Gly Leu Arg Val Val  Tyr Glu Ser
    1115                 1120                 1125

Leu Pro  Phe Tyr Lys Ala Glu  Lys Ile Val Asn Leu  Ile Ser Gly
    1130                 1135                 1140

Thr Lys  Ser Ile Thr Asn Ile  Leu Glu Lys Thr Ser  Ala Ile Asp
    1145                 1150                 1155

Leu Thr  Asp Ile Asp Arg Ala  Thr Glu Met Met Arg  Lys Asn Ile
    1160                 1165                 1170

Thr Leu  Leu Ile Arg Ile Leu  Pro Leu Asp Cys Asn  Arg Asp Lys
    1175                 1180                 1185

Arg Glu  Ile Leu Ser Met Glu  Asn Leu Ser Ile Thr  Glu Leu Ser
    1190                 1195                 1200

Lys Tyr  Val Arg Glu Arg Ser  Trp Ser Leu Ser Asn  Ile Val Gly
    1205                 1210                 1215

Val Thr  Ser Pro Ser Ile Met  Tyr Thr Met Asp Ile  Lys Tyr Thr
    1220                 1225                 1230

Thr Ser  Thr Ile Ala Ser Gly  Ile Ile Ile Glu Lys  Tyr Asn Val
    1235                 1240                 1245

Asn Ser  Leu Thr Arg Gly Glu  Arg Gly Pro Thr Lys  Pro Trp Val
    1250                 1255                 1260

Gly Ser  Ser Thr Gln Glu Lys  Lys Thr Met Pro Val  Tyr Asn Arg
    1265                 1270                 1275

Gln Val  Leu Thr Lys Lys Gln  Arg Asp Gln Ile Asp  Leu Leu Ala
    1280                 1285                 1290

Lys Leu  Asp Trp Val Tyr Ala  Ser Ile Asp Asn Lys  Asp Glu Phe
    1295                 1300                 1305

Met Glu  Glu Leu Ser Ile Gly  Thr Leu Gly Leu Thr  Tyr Glu Lys
    1310                 1315                 1320

Ala Lys  Lys Leu Phe Pro Gln  Tyr Leu Ser Val Asn  Tyr Leu His
    1325                 1330                 1335

Arg Leu  Thr Val Ser Ser Arg  Pro Cys Glu Phe Pro  Ala Ser Ile
    1340                 1345                 1350

Pro Ala  Tyr Arg Thr Thr Asn  Tyr His Phe Asp Thr  Ser Pro Ile
    1355                 1360                 1365

Asn Arg  Ile Leu Thr Glu Lys  Tyr Gly Asp Glu Asp  Ile Asp Ile
    1370                 1375                 1380

Val Phe  Gln Asn Cys Ile Ser  Phe Gly Leu Ser Leu  Met Ser Val
    1385                 1390                 1395

Val Glu  Gln Phe Thr Asn Val  Cys Pro Asn Arg Ile  Ile Leu Ile
    1400                 1405                 1410

Pro Lys  Leu Asn Glu Ile His  Leu Met Lys Pro Pro  Ile Phe Thr
    1415                 1420                 1425

Gly Asp  Val Asp Ile His Lys  Leu Lys Gln Val Ile  Gln Lys Gln
    1430                 1435                 1440

His Met  Phe Leu Pro Asp Lys  Ile Ser Leu Thr Gln  Tyr Val Glu
    1445                 1450                 1455

Leu Phe  Leu Ser Asn Lys Thr  Leu Lys Ser Gly Ser  His Val Asn
    1460                 1465                 1470
```

-continued

```
Ser Asn  Leu Ile Leu Ala His  Lys Ile Ser Asp Tyr  Phe His Asn
    1475                 1480                 1485

Thr Tyr  Ile Leu Ser Thr Asn  Leu Ala Gly His Trp  Ile Leu Ile
    1490                 1495                 1500

Ile Gln  Leu Met Lys Asp Ser  Lys Gly Ile Phe Glu  Lys Asp Trp
    1505                 1510                 1515

Gly Glu  Gly Tyr Ile Thr Asp  His Met Phe Ile Asn  Leu Lys Val
    1520                 1525                 1530

Phe Phe  Asn Ala Tyr Lys Thr  Tyr Leu Leu Cys Phe  His Lys Gly
    1535                 1540                 1545

Tyr Gly  Lys Ala Lys Leu Glu  Cys Asp Met Asn Thr  Ser Asp Leu
    1550                 1555                 1560

Leu Cys  Val Leu Glu Leu Ile  Asp Ser Ser Tyr Trp  Lys Ser Met
    1565                 1570                 1575

Ser Lys  Val Phe Leu Glu Gln  Lys Val Ile Lys Tyr  Ile Leu Ser
    1580                 1585                 1590

Gln Asp  Ala Ser Leu His Arg  Val Lys Gly Cys His  Ser Phe Lys
    1595                 1600                 1605

Leu Trp  Phe Leu Lys Arg Leu  Asn Val Ala Glu Phe  Thr Val Cys
    1610                 1615                 1620

Pro Trp  Val Val Asn Ile Asp  Tyr His Pro Thr His  Met Lys Ala
    1625                 1630                 1635

Ile Leu  Thr Tyr Ile Asp Leu  Val Arg Met Gly Leu  Ile Asn Ile
    1640                 1645                 1650

Asp Arg  Ile His Ile Lys Asn  Lys His Lys Phe Asn  Asp Glu Phe
    1655                 1660                 1665

Tyr Thr  Ser Asn Leu Phe Tyr  Ile Asn Tyr Asn Phe  Ser Asp Asn
    1670                 1675                 1680

Thr His  Leu Leu Thr Lys His  Ile Arg Ile Ala Asn  Ser Glu Leu
    1685                 1690                 1695

Glu Asn  Asn Tyr Asn Lys Leu  Tyr His Pro Thr Pro  Glu Thr Leu
    1700                 1705                 1710

Glu Asn  Ile Leu Ala Asn Pro  Ile Lys Ser Asn Asp  Lys Lys Thr
    1715                 1720                 1725

Leu Asn  Asp Tyr Cys Ile Gly  Lys Asn Val Asp Ser  Ile Met Leu
    1730                 1735                 1740

Pro Leu  Leu Ser Asn Lys Lys  Leu Val Lys Ser Ser  Ala Met Ile
    1745                 1750                 1755

Arg Thr  Asn Tyr Ser Lys Gln  Asp Leu Tyr Asn Leu  Phe Pro Thr
    1760                 1765                 1770

Val Val  Ile Asp Arg Ile Ile  Asp His Ser Gly Asn  Thr Ala Lys
    1775                 1780                 1785

Ser Asn  Gln Leu Tyr Thr Thr  Thr Ser His Gln Ile  Ser Leu Val
    1790                 1795                 1800

His Asn  Ser Thr Ser Leu Tyr  Cys Met Leu Pro Trp  His His Ile
    1805                 1810                 1815

Asn Arg  Phe Asn Phe Val Phe  Ser Ser Thr Gly Cys  Lys Ile Ser
    1820                 1825                 1830

Ile Glu  Tyr Ile Leu Lys Asp  Leu Lys Ile Lys Asp  Pro Asn Cys
    1835                 1840                 1845

Ile Ala  Phe Ile Gly Glu Gly  Ala Gly Asn Leu Leu  Leu Arg Thr
    1850                 1855                 1860

Val Val  Glu Leu His Pro Asp  Ile Arg Tyr Ile Tyr  Arg Ser Leu
```

```
    1865                1870                1875

Lys Asp  Cys Asn Asp His Ser  Leu Pro Ile Glu Phe  Leu Arg Leu
    1880                1885                1890

Tyr Asn  Gly His Ile Asn Ile  Asp Tyr Gly Glu Asn  Leu Thr Ile
    1895                1900                1905

Pro Ala  Thr Asp Ala Thr Asn  Asn Ile His Trp Ser  Tyr Leu His
    1910                1915                1920

Ile Lys  Phe Ala Glu Pro Ile  Ser Leu Phe Val Cys  Asp Ala Glu
    1925                1930                1935

Leu Pro  Val Thr Val Asn Trp  Ser Lys Ile Ile Ile  Glu Trp Ser
    1940                1945                1950

Lys His  Val Arg Lys Cys Lys  Tyr Cys Ser Ser Val  Asn Lys Cys
    1955                1960                1965

Thr Leu  Ile Val Lys Tyr His  Ala Gln Asp Asp Ile  Asp Phe Lys
    1970                1975                1980

Leu Asp  Asn Ile Thr Ile Leu  Lys Thr Tyr Val Cys  Leu Gly Ser
    1985                1990                1995

Lys Leu  Lys Gly Ser Glu Val  Tyr Leu Val Leu Thr  Ile Gly Pro
    2000                2005                2010

Ala Asn  Ile Phe Pro Val Phe  Asn Val Val Gln Asn  Ala Lys Leu
    2015                2020                2025

Ile Leu  Ser Arg Thr Lys Asn  Phe Ile Met Pro Lys  Lys Ala Asp
    2030                2035                2040

Lys Glu  Ser Ile Asp Ala Asn  Ile Lys Ser Leu Ile  Pro Phe Leu
    2045                2050                2055

Cys Tyr  Pro Ile Thr Lys Lys  Gly Ile Asn Thr Ala  Leu Ser Lys
    2060                2065                2070

Leu Lys  Ser Val Val Ser Gly  Asp Ile Leu Ser Tyr  Ser Ile Ala
    2075                2080                2085

Gly Arg  Asn Glu Val Phe Ser  Asn Lys Leu Ile Asn  His Lys His
    2090                2095                2100

Met Asn  Ile Leu Lys Trp Phe  Asn His Val Leu Asn  Phe Arg Ser
    2105                2110                2115

Thr Glu  Leu Asn Tyr Asn His  Leu Tyr Met Val Glu  Ser Thr Tyr
    2120                2125                2130

Pro Tyr  Leu Ser Glu Leu Leu  Asn Ser Leu Thr Thr  Asn Glu Leu
    2135                2140                2145

Lys Lys  Leu Ile Lys Ile Thr  Gly Ser Leu Leu Tyr  Asn Phe His
    2150                2155                2160

Asn Glu
    2165


<210> SEQ ID NO 7
<211> LENGTH: 194
<212> TYPE: PRT
<213> ORGANISM: respiratory syncytial virus

<400> SEQUENCE: 7

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45
```

-continued

Ser Met Asp Lys Ser Ile Asp Thr Leu Ser Glu Ile Ser Gly Ala Ala
    50              55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Leu Thr Val Ser Asp Thr Asn Asp His Ala Lys Asn Asn Asp
            180                 185                 190

Thr Thr

<210> SEQ ID NO 8
<211> LENGTH: 90
<212> TYPE: PRT
<213> ORGANISM: respiratory syncytial virus

<400> SEQUENCE: 8

Met Thr Met Pro Lys Ile Met Ile Leu Pro Asp Lys Tyr Pro Cys Ser
1               5                   10                  15

Ile Thr Ser Ile Leu Ile Thr Ser Arg Cys Arg Val Thr Met Tyr Asn
            20                  25                  30

Arg Lys Asn Thr Leu Tyr Phe Asn Gln Asn Asn Pro Asn Asn His Met
        35                  40                  45

Tyr Ser Pro Asn Gln Thr Phe Asn Glu Ile His Trp Thr Ser Gln Asp
    50                  55                  60

Leu Ile Asp Thr Ile Gln Asn Phe Leu Gln His Leu Gly Val Ile Glu
65                  70                  75                  80

Asp Ile Tyr Thr Ile Tyr Ile Leu Val Ser
                85                  90

<210> SEQ ID NO 9
<211> LENGTH: 241
<212> TYPE: PRT
<213> ORGANISM: respiratory syncytial virus

<400> SEQUENCE: 9

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Asn Ala Gly Asn Lys Pro Asn Tyr Gln
65                  70                  75                  80

Arg Lys Pro Leu Val Ser Phe Lys Glu Asp Pro Ile Pro Ser Asp Asn

-continued

```
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Glu Asp
225                 230                 235                 240

Phe


<210> SEQ ID NO 10
<211> LENGTH: 139
<212> TYPE: PRT
<213> ORGANISM: respiratory syncytial virus

<400> SEQUENCE: 10

Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile His Leu Thr Asn Ala Leu Ala Lys Ala Val Ile His Thr
        35                  40                  45

Ile Lys Leu Asn Gly Ile Val Phe Val His Val Ile Thr Ser Ser Asp
    50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Ile Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu Ser Glu Leu Leu Gly Phe Asp Leu Asn Pro
    130                 135


<210> SEQ ID NO 11
<211> LENGTH: 124
<212> TYPE: PRT
<213> ORGANISM: respiratory syncytial virus

<400> SEQUENCE: 11

Met Asp Thr Thr His Asn Asp Thr Thr Pro Gln Arg Leu Met Ile Thr
1               5                   10                  15

Asp Met Arg Pro Leu Ser Leu Glu Thr Thr Ile Thr Ser Leu Thr Arg
            20                  25                  30
```

-continued

```
Asp Ile Ile Thr His Arg Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
        115                 120


<210> SEQ ID NO 12
<211> LENGTH: 1725
<212> TYPE: RNA
<213> ORGANISM: respiratory syncytial virus

<400> SEQUENCE: 12

auggaguugc caauccucaa agcaaaugca auuaccacaa uccucgcugc agucacauuu      60

ugcuuugcuu cuagucaaaa caucacugaa gaauuuuauc aaucaacaug cagugcaguu     120

agcaaaggcu aucuuagugc ucuaagaacu gguugguaua cuaguguuau aacuauagaa     180

uuaaguaaua ucaaggaaaa uaaguguaau ggaacagaug cuaagguaaa auugauaaac     240

caagaauuag auaaauauaa aaaugcugua acagaauugc aguugcucau gcaaagcaca     300

acagcagcaa acaaucgagc cagaagagaa cuaccaaggu uuaugaauua uacacucaac     360

aauaccaaaa aaaccaaugu aacauuaagc aagaaaagga aaagaagauu ucuugguuuu     420

uuguuaggug uuggaucugc aaucgccagu ggcauugcug uaucuaaggu ccugcacuua     480

gaaggagaag ugaacaagau caaaagugcu cuacuaucca caaacaaggc cguagucagc     540

uuaucaaaug gaguuagugu cuuaaccagc aaaguguuag accucaaaaa cuauauagau     600

aaacaauugu uaccuauugu gaauaagcaa agcugcagaa uaucaaauau agaaacugug     660

auagaguucc aacaaaagaa caacagacua cuagagauua ccagggaauu uaguguuaau     720

gcagguguaa cuacaccugu aagcacuuac auguuaacua auagugaauu auugucauua     780

aucaaugaua ugccuauaac aaaugaucag aaaaaguuaa uguccaacaa uguucaaaua     840

guuagacagc aaaguuacuc uaucaugucc auaauaaaag aggaagucuu agcauaugua     900

guacaauuac cacuauaugg ugugauagau acaccuuguu ggaaauuaca cacaucccu     960

cuauguacaa ccaacacaaa agaagggguca aacaucuguu uaacaagaac ugacagagga    1020

ugguacugug acaaugcagg aucaguaucu uucuucccac aagcugaaac auguaaaguu    1080

caaucgaauc gaguauuuug ugacacaaug aacaguuuaa cauuaccaag ugaaguaaau    1140

cucugcaaug uugacauauu caaucccaaa uaugauugua aaauuaugac uucaaaaaca    1200

gauguaagca gcuccguuau cacaucucua ggagccauug ugucaugcua uggcaaaacu    1260

aaauguacag cauccaauaa aaaucgugga aucauaaaga cauuuucuaa cgggugugau    1320

uauguaucaa auaaaggggu ggacacugug ucuguaggua acacauuaua uuauguaaau    1380

aagcaagaag gcaaaagucu cuauguaaaa ggugaaccaa uaauaaauuu cuaugaccca    1440

uuaguauucc ccucugauga auuugaugca ucaauaucuc aagucaauga gaagauuaac    1500

cagaguuuag cauuuauucg uaaauccgau gaauuauuac aucauguaaa ugcugguaaa    1560
```

-continued ucaaccacaa auaucaugau aacuacuaua auuauaguga uuauaguaau auuguuauca 1620
uuaauugcug uuggacugcu ccuauacugu aaggccagaa gcacaccagu cacacuaagc 1680
aaggaucaac ugagugguau aaauaauauu gcauuuagua acuga 1725

<210> SEQ ID NO 13
<211> LENGTH: 897
<212> TYPE: RNA
<213> ORGANISM: respiratory syncytial virus

<400> SEQUENCE: 13
auguccaaaa acaaggacca acgcaccgcu aagacacuag aaaagaccug ggacacucuc 60
aaucauuuau uauucauauc aucgggcuua uauaaguuaa aucuuaaauc uauagcacaa 120
aucacauuau ccauucuggc aaugauaauc ucaacuucac uuauaauuac agccaucaua 180
uucauagccu cggcaaacca caaagucaca cuaacaacug caaucauaca agaugcaaca 240
agccagauca agaacacaac cccaacauac cucacucagg auccucagcu uggaaucagc 300
uucuccaauc ugucugaaau uacaucacaa accaccacca uacuagcuuc aacaacacca 360
ggagucaagu caaaccugca acccacaaca gucaagacua aaaacacaac aacaacccaa 420
acacaaccca gcaagcccac uacaaaacaa cgccaaaaca aaccaccaaa caaacccaau 480
aaugauuuuc acuucgaagu guuuaacuuu guacccugca gcauaugcag caacaaucca 540
accugcuggg cuaucugcaa aagaauacca aacaaaaaac caggaaagaa aaccaccacc 600
aagccuacaa aaaaaccaac cuucaagaca accaaaaaag aucucaaacc ucaaaccacu 660
aaaccaaagg aaguacccac caccaagccc acagaagagc caaccaucaa caccaccaaa 720
acaaacauca caacuacacu gcucaccaac aacaccacag gaaauccaaa acucacaagu 780
caaauggaaa ccuuccacuc aaccuccucc gaaggcaauc uaagcccuuc ucaagucucc 840
acaacauccg agcacccauc acaacccuca ucuccaccca acacaacacg ccaguag 897

<210> SEQ ID NO 14
<211> LENGTH: 195
<212> TYPE: RNA
<213> ORGANISM: respiratory syncytial virus

<400> SEQUENCE: 14
auggaaaaua cauccauaac aauagaauuc ucaagcaaau ucuggccuua cuuuacacua 60
auacacauga ucacaacaau aaucucuuug cuaaucauaa ucuccaucau gacugcaaua 120
cuaaacaaac uuugugaaua uaacguauuc cauaacaaaa ccuuugaguu accaagagcu 180
cgagucaaca cauag 195

<210> SEQ ID NO 15
<211> LENGTH: 771
<212> TYPE: RNA
<213> ORGANISM: respiratory syncytial virus

<400> SEQUENCE: 15
auggaaacau acgugaacaa gcuucacgaa ggcuccacau acacagcugc uguucaauac 60
aauguccuag aaaaagacga ugacccugca ucacuuacaa uaugggugcc cauguuccaa 120
ucaucuaugc cagcagauuu acuuauaaaa gaacuagcua augucaacau acuagugaaa 180
caaauaucca cacccaaggg accuucacua agagucauga uaaacucaag aagugcauug 240
cuagcacaaa ugcccagcaa auuuaccaua ugugcuaaug uguccuugga ugaaagaagc 300
aaacuggcau augauguaac cacacccugu gaaaucaagg cauguagucu aacaugccua 360
aaaucaaaaa auauguuaac uacaguuaaa gaucucacua ugaagacacu caacccccaca 420 caugauauua uugcuuuaug ugaauuugaa aacauaguaa caucaaaaaa agucauaaua 480
ccaacauacc uaagauccau cagugucaga aauaaagauc ugaacacacu ugaaaauaua 540
acaaccacug aauucaaaaa ugccaucaca aaugcaaaaa ucaucccuua cucaggauua 600
cuauuaguca ucacagugac ugacaacaaa ggagcauuca aauacauaaa gccgcaaagu 660
caauucauag uagaucuugg agcuuaccua gaaaaagaaa guauauauua uguuaccaca 720
aauuggaagc acacagcuac acgauuugca aucaaaccca uggaagauua a 771

<210> SEQ ID NO 16
<211> LENGTH: 1176
<212> TYPE: RNA
<213> ORGANISM: respiratory syncytial virus

<400> SEQUENCE: 16
auggcucuua gcaaagucaa guugaaugau acacucaaca aagaucaacu ucugucaucu 60
agcaaauaca ccauccaacg gagcacagga gauaguauug auacuccuaa uuaugaugug 120
cagaaacaca ucaauaaguu auguggcaug uuauuaauca cagaagaugc uaaucauaaa 180
uucacugggu uaauagguau guuauaugcu augucuaggu uaggaagaga agacaccaua 240
aaaauacuca gagaugcggg auaucaugua aaagcaaaug gaguagaugu aacaacacau 300
cgucaagaca ucaaugggaa agaaaugaaa uuugaagugu uaacauuggc aagcuuaaca 360
acugaaauuc aaaucaacau ugagauagaa ucuagaaaau ccuacaaaaa aaugcuaaaa 420
gaaaugggag agguagcucc agaauacagg caugauucuc cugauugugg gaugauaaua 480
uuauguauag cagcauuagu aauaaccaaa uuggcagcag gggauagauc uggucuuaca 540
gccgugauua ggagagcuaa uaauguccua aaaaaugaaa ugaaacguua caaaggcuua 600
cuacccaagg auauagccaa cagcuucuau gaaguguuug aaaaacaucc ccacuuuaua 660
gauguuuuug uucauuuugg uauagcacaa ucuuccacca gagguggcag uagaguugaa 720
gggauuuuug caggauuguu uaugaaugcc uauggugcag ggcaaguaau gcuacggugg 780
ggagucuuag caaaaucagu uaaaaauauu auguuaggac augcuagugu gcaagcagaa 840
auggaacaag uuguugaggu uuaugaauau gcccaaaaau ugggugugga agcaggauuc 900
uaccauauau ugaacaaccc aaaagcauca uuauuaucuu ugacucaauu uccucacuuu 960
uccaguguag uauuaggcaa ugcugcuggc cuaggcauaa ugggagagua cagagguaca 1020
ccgaggaauc aagaucuaua ugaugcagca aaggcauaug cugaacaacu caaagaaaau 1080
ggugugauua acuacagugu auuagacuug acagcagaag aacuagaggc uaucaaacau 1140
cagcuuaauc caaaagauaa ugauguagag cuuuga 1176

<210> SEQ ID NO 17
<211> LENGTH: 6498
<212> TYPE: RNA
<213> ORGANISM: respiratory syncytial virus

<400> SEQUENCE: 17
auggauccca uuauuaaugg aaauucugcu aauguuuauc uaaccgauag uuauuuaaaa 60
gguguuaucu cuuucucaga guguaaugcu uuaggaaguu acauauucaa ugguccuuau 120
cucaaaaaug auuauaccaa cuuaauuagu agacaaaauc cauuaauaga acacaugaau 180
cuaaagaaac uaaauauaac acaguccuua auaucuaagu aucauaaagg ugaaauaaaa 240

-continued

```
uuagaagagc cuacuuauuu ucagucauua cuuaugacau acaagaguau gaccucguug    300
gaacagauug cuaccacuaa uuuacuuaaa aagauaauaa gaagagcuau agaaauaagu    360
gaugucaaag ucuaugcuau auugaauaaa cuagggcuua aagaaaagga caagauuaaa    420
uccaacaaug gacaggauga agacaacuca guuauuacga ccauaaucaa agaugauaua    480
cuuucagcug uuaaggauaa ucaaucucau cuuaaagcag acaaaaauca cucuacaaaa    540
caaaaagaca caaucaaaac aacacucuug aagaaauuaa uguguucaau gcagcauccu    600
ccaucauggu uaauacauug guuuaauuua uacacaaaau uaaacaacau auuaacacag    660
uaucgaucaa augagguuaa aaaccauggg uuuauauuga uagauaauca aacucuuagu    720
ggauuucaau uuauuuugaa ucaauauggu uguauaguuu aucauaagga acucaaaaga    780
auuacuguga caaccuauaa ucaauucuug acauggaaag auauuagccu uaguagauua    840
aauguuuguu uaauuacaug gauuaguaac ugcuugaaca cauuaaauaa aagcuuaggc    900
uuaagaugcg gauucaauaa uguuaucuug acacaacuau uccuuuaugg ugauuguaua    960
cuaaagcuau uucacaauga gggguucuac auaauaaaag agguagaggg auuuauuaug   1020
ucucuaauuu uaaauauaac agaagaagau caauucagaa aacgauuuua uaauaguaug   1080
cucaacaaca ucacagaugc ugcuaauaaa gcucagaaaa aucugcuauc aagaguaugu   1140
cauacauuau uagauaagac aguauccgau aauauaauaa auggcagaug gauaauucua   1200
uuaaguaagu uccuuaaauu aauuaagcuu gcaggugaca auaaccuuaa caaucugagu   1260
gaacuauauu uuuuguucag aauauuugga cacccaaugg uagaugaaag acaagccaug   1320
gaugcuguua aaguuaauug caaugagacc aaauuuuacu uguuaagcag uuugaguaug   1380
uuaagaggug ccuuuauaua uagaauuaua aaaggguuug uaaauaauua caacagaugg   1440
ccuacuuuaa gaaaugcuau uguuuuaccc uuaagauggu uaacuuacua uaaacuaaac   1500
acuuauccuu cuuuguugga acuuacagaa agagauuuga uuguguuauc aggacuacgu   1560
uucuaucgug aguuucgguu gccuaaaaaa guggaucuug aaaugauuau aaaugauaaa   1620
gcuauaucac ccccuaaaaa uuugauaugg acuaguuucc cuagaaauua uaugccguca   1680
cacauacaaa acuauauaga acaugaaaaa uuaaaauuuu ccgagaguga uaaaucaaga   1740
agaguauuag aguauuauuu aagagauaac aaauucaaug aaugugauuu auacaacugu   1800
guaguuaauc aaaguuaucu caacaacccu aaucaugugg uaucauugac aggcaaagaa   1860
agagaacuca guguagguag aauguuugca augcaaccgg gaauguucag acagguucaa   1920
auauuggcag agaaaaugau agcugaaaac auuuuacaau ucuuuccuga aagucuuaca   1980
agauauggug aucuagaacu acaaaaaaua uuagaauuga aagcaggaau aaguaacaaa   2040
ucaaaucgcu acaaugauaa uuacaacaau uacauuagua agugcucuau caucacagau   2100
cucagcaaau ucaaucaagc auuucgauau gaaacgucau guauuuguag ugaugugcug   2160
gaugaacugc augguguaca aucucuauuu uccugguuac auuuaacuau uccucauguc   2220
acaauaauau gcacauauag gcaugcaccc cccuauauaa gagaucauau uguagaucuu   2280
aacaauguag augaacaaag uggauuauau agauaucaca uggguggauu ugaagggugg   2340
ugucaaaaac uauggaccau agaagcuaua ucacuauugg aucuaauauc ucucaaaggg   2400
aaauucucaa uuacugcuuu aauuaauggu gacaaucaau caauagauau aagcaaacca   2460
gucagacuca uggaagguca aacucaugcu caagcagauu auuugcuagc auuaaauagc   2520
cuuaaauuac uguauaaaga guaugcaggc auaggucaca aauuaaaagg aacugagacu   2580
uauauaucac gagauaugca auuuaugagu aaaacaauuc aacauaacgg uguauauuac   2640
```

-continued

```
ccugcuagua uaaagaaagu ccuaagagug ggaccgugga uaaacacuau acuugaugau   2700
uucaaaguga gucuagaauc uauagguagu uugacacaag aauuagaaua uagaggugaa   2760
agucuauuau gcaguuuaau auuuagaaau guaugguuau auaaucaaau ugcucuacaa   2820
uuaaaaaauc augcguuaug uaacaauaaa uuuauauugg acauauuaaa gguucugaaa   2880
cacuuaaaaa ccuuuuuuaa ucuugauaau auugauacag cauuaacauu guauaugaau   2940
uuacccaugu uauuuggugg uggugauccc aacuuguuau aucgaaguuu cuauagaaga   3000
acuccugauu uccucacaga ggcuauaguu cacucugugu ucauacuuag uuauuauaca   3060
aaccaugacu uaaaagauaa acuucaagau uugucagaug auagauugaa uaaguucuua   3120
acaugcauaa ucacguuuga caaaaacccu aaugcugaau ucguaacauu gaugagagau   3180
ccucaagcuu uagggucuga gagacaagcu aaaauuacua gugaaaucaa uagacuggca   3240
guuacagagg uuuugaguac agcuccaaac aaaauauucu ccaaaagugc acaacauuau   3300
accacuacag agauagaucu aaaugauauu augcaaaaua uagaaccuac auauccucac   3360
gggcuaagag uuguuuauga aaguuuaccc uuuuauaaag cagagaaaau aguaaaucuu   3420
auaucaggua caaaaucuau aacuaacaua cuggaaaaga cuucugccau agacuuaaca   3480
gauauugaua gagccacuga gaugaugagg aaaaacauaa cuuugcuuau aaggauacuu   3540
ccauuggauu guaacagaga uaaaagagaa auauugagua uggaaaaccu aaguauuacu   3600
gaauuaagca aauauguuag ggaaagaucu uggucuuuau ccaauauagu ugguguuaca   3660
ucacccagua ucauguauac aauggacauc aaauauacaa caagcacuau agcuaguggc   3720
auaauuauag agaaauauaa uguuaacagu uuaacacgug gugagagagg accaacuaaa   3780
ccaugguuug guucaucuac acaagagaaa aaaacaaugc caguuuauaa uagacaaguu   3840
uuaaccaaaa aacaaagaga ucaaauagau cuauuagcaa aauuggauug gguguaugca   3900
ucuauagaua acaaggauga auucauggaa gaacucagca uaggaacccu uggguuaaca   3960
uaugaaaagg ccaaaaaauu auuuccacaa uauuuaagug ucaacuauuu gcaucgccuu   4020
acagucagua guagaccaug ugaauucccu gcaucaauac cagcuuauag aacaacaaau   4080
uaucacuuug acacuagccc uauuaaucgc auauuaacag aaaaguaugg ugaugaagau   4140
auugacauag uauuccaaaa cuguauaagc uuuggccuua gcuuaauguc aguaguagaa   4200
caauuuacua auguaugucc uaacagaauu auucucauac cuaagcuuaa ugagauacau   4260
uugaugaaac cucccauauu cacaggugau guugauauuc acaaguuaaa acaagugaua   4320
caaaaacagc auauguuuuu accagacaaa auaaguuuga cucaauaugu ggaauuauuc   4380
uuaaguaaca aaacacucaa aucuggaucu cauguuaauu cuaauuuaau auuggcacau   4440
aaaauaucug acuauuuuca uaauacuuac auuuuaagua cuaauuuagc uggacauugg   4500
auucuaauua uacaacuuau gaaagauucu aaagguauuu uugaaaaaga uuggggagag   4560
ggauauauaa cugaucauau guuuauuaau uugaaaguuu ucuucaaugc uuauaagacc   4620
uaucucuugu guuuucauaa agguuauggc aaagcaaaac uggagugug uaugaacacu   4680
ucagaucuuc uauguguauu ggaauuaaua gacaguaguu auuggaaguc uaugucuaag   4740
guauuuuuag aacaaaaagu uaucaaauac auucuuagcc aagaugcaag uuuacauaga   4800
guaaaaggau gucauagcuu caaauuaugg uuucuuaaac gucuuaaugu agcagaauuu   4860
acaguuugcc cuuggguugu uaacauagau uaucauccaa cacauaugaa agcaauauua   4920
acuuauauag aucuuguuag aaugggauug auaaauauag auagaauaca cauuaaaaau   4980
```

aaacacaaau ucaaugauga auuuuauacu ucuaaucucu uuuacauuaa uuauaacuuc 5040
ucagauaaua cucaucuauu aacuaaacau auaaggauug cuaauucaga auuagaaaau 5100
aauuacaaca aauuauauca uccuacacca gaaacccuag agaauauacu agccaauccg 5160
auuaaaagua augacaaaaa gacacugaac gacuauugua uagguaaaaa uguugacuca 5220
auaauguuac cauuguuauc uaauaagaag cuuguuaaau cgucugcaau gauuagaacc 5280
aauuacagca aacaagaccu guacaaucua uucccuacgg uugugaucga uagaauuaua 5340
gaucauucag guaauacagc caaauccaac caacuuuaca cuacuacuuc ccaucaaaua 5400
ucuuuagugc acaauagcac aucacuuuau ugcaugcuuc cuuggcauca uauuaauaga 5460
uucaauuuug uauuuaguuc uacagguugu aaaauuagua uagaguauau uuuaaaagac 5520
cuuaaaauua aagauccuaa uuguauagca uucauaggug aaggagcagg gaauuuauua 5580
uugcguacag ugguggaacu ucauccugac auaagauaua uuuacagaag ucugaaagau 5640
ugcaaugauc auaguuuacc uauugaguuu uuaaggcuau acaauggaca uaucaacauu 5700
gauuauggug aaaauuugac cauuccugcu acagaugcaa ccaacaacau ucauuggucu 5760
uauuuacaua uaaaguuugc ugaaccuauc agucuuuuug uaugugaugc cgaauugccu 5820
guaacaguca acuggaguaa aauuauaaua gaauggagca agcauguaag aaaaugcaag 5880
uacuguuccu caguuaauaa auguacguua auaguaaaau aucaugcuca agaugauauu 5940
gauuucaaau uagacaauau aacuauauua aaaacuuaug uaugcuuagg caguaaguua 6000
aagggaucgg agguuuacuu aguccuuaca auagguccug caaauauauu uccaguauuu 6060
aauguaguac aaaaugcuaa auugauacua ucaagaacca aaaauuucau caugccuaag 6120
aaagcugaua aagagucuau ugaugcaaau auuaaaaguu ugauacccuu ucuuuguuac 6180
ccuauaacaa aaaaaggaau uaauacugca uugucaaaac uaaagagugu uguuagugga 6240
gauauacuau cauauucuau agcuggacgg aaugaaguuu ucagcaauaa acuuauaaau 6300
cauaagcaua ugaacaucuu aaagugguuc aaucauguuu uaaauuucag aucaacagaa 6360
cuaaacuaua accauuuaua uaugguagaa ucuacauauc cuuaccuaag ugaauuguua 6420
aacagcuuga caacuaauga acuuaaaaaa cugauuaaaa ucacagguag ucuguuauac 6480
aacuuucaua augaauaa 6498

<210> SEQ ID NO 18
<211> LENGTH: 585
<212> TYPE: RNA
<213> ORGANISM: respiratory syncytial virus

<400> SEQUENCE: 18
augucacgaa ggaauccuug caaauuugaa auucgagguc auugcuugaa ugguaagaga 60
ugucauuuua gucauaauua uuuugaaugg ccaccccaug cacugcucgu aagacaaaac 120
uuuauguuaa acagaauacu uaagucuaug gauaaaagua uagauaccuu aucagaaaua 180
aguggagcug cagaguugga cagaacagaa gaguaugcuc uugguguagu uggagugcua 240
gagaguuaua uaggaucaau aaauaauaua acuaaacaau cagcaugugu ugccaugagc 300
aaacuccuca cugaacucaa uagugaugau aucaaaaaac ugagagacaa ugaagagcua 360
aauucaccca agauaagagu guacaauacu gucauaucau auauugaaag caacaggaaa 420
aacaauaaac aaacuaucca ucuguuaaaa agauugccag cagacguauu gaagaaaacc 480
aucaaaaaca cauuggauau ccacaagagc auaaccauca acaacccaaa agaauuaacu 540
guuagugaua caaaugacca ugccaaaaau aaugauacua ccuga 585

<210> SEQ ID NO 19
<211> LENGTH: 273
<212> TYPE: RNA
<213> ORGANISM: respiratory syncytial virus

<400> SEQUENCE: 19
augaccaugc caaaaauaau gauacuaccu gacaaauauc cuuguaguau aacuuccaua 60
cuaauaacaa guagauguag agucacuaug uauaaucgaa agaacacacu auauuucaau 120
caaaacaacc caaauaacca uauguacuca ccgaaucaaa cauucaauga aauccauugg 180
accucacaag acuugauuga cacaauucaa aauuuucuac agcaucuagg uguuauugag 240
gauauauaua caauauauau auuaguguca uaa 273

<210> SEQ ID NO 20
<211> LENGTH: 726
<212> TYPE: RNA
<213> ORGANISM: respiratory syncytial virus

<400> SEQUENCE: 20
auggaaaagu uugcuccuga auuccaugga gaagaugcaa acaacagggc uacuaaauuc 60
cuagaaucaa uaaagggcaa auucacauca ccuaaagauc ccaagaaaaa agauaguauc 120
auaucuguca acucaauaga uauagaagua accaaagaaa gcccuauaac aucaaauuca 180
accauuauua acccaacaaa ugagacagau gauaaugcag ggaacaagcc caauuaucaa 240
agaaaaccuc uaguaaguuu caaagaagac ccuauaccaa gugauaaucc cuuuucaaaa 300
cuauacaaag aaaccauaga gacauuugau aacaaugaag aagaaucuag cuauucauau 360
gaagaaauaa augaucagac gaacgauaau auaacugcaa gauuagauag gauugaugaa 420
aaauuaagug aaauacuagg aaugcuucac acauuaguag uagcaagugc aggaccuaca 480
ucugcuaggg augguauaag agaugccaug guugguuuaa gagaagaaau gauagaaaaa 540
aucagaacug aagcauuaau gaccaaugac agauuagaag cuauggcaag acucaggaau 600
gaggaaagug aaaagauggc aaaagacaca ucagaugaag ugucucucaa uccaacauca 660
gagaaauuga acaaccuguu ggaagggaau gauagugaca augaucuauc acuugaagau 720
uucuga 726

<210> SEQ ID NO 21
<211> LENGTH: 420
<212> TYPE: RNA
<213> ORGANISM: respiratory syncytial virus

<400> SEQUENCE: 21
augggcagca auucguugag uaugauaaaa guuagauuac aaaauuuguu ugacaaugau 60
gaaguagcau uguuaaaaau aacaugcuau acugacaaau uaauacauuu aacuaaugcu 120
uuggcuaagg cagugauaca uacaaucaaa uugaauggca uuguguuugu gcauguuauu 180
acaaguagug auauuugccc uaauaauaau auuguaguaa aauccaauuu cacaacaaug 240
ccagugcuac aaaauggagg uuauauaugg gaaaugaugg aauuaacaca uugcucucaa 300
ccuaaugguc uaauagauga caauugugaa auuaaauucu ccaaaaaacu aagugauuca 360
acaaugacca auuauaugaa ucaauuaucu gaauuacuug gauuugaucu uaauccauaa 420

<210> SEQ ID NO 22
<211> LENGTH: 375
<212> TYPE: RNA

<213> ORGANISM: respiratory syncytial virus

<400> SEQUENCE: 22
auggacacaa cccacaauga uaccacacca caaagacuga ugaucacaga caugagaccg 60
uugucacuug agacuacaau aacaucacua accagagaca ucauaacaca cagauuuaua 120
uacuuaauaa aucaugaaug cauagugaga aaacuugaug aaagacaggc cacauuuaca 180
uuccugguca acuaugaaau gaaacuauug cacaaaguag gaagcacuaa auauaaaaaa 240
uauacugaau acaacacaaa auauggcacu uucccuaugc cgauauucau caaucaugau 300
ggguucuuag aaugcauugg cauuaagccu acaaagcaua cucccauaau auacaaguau 360
gaucucaauc cauag 375

<210> SEQ ID NO 23
<211> LENGTH: 42
<212> TYPE: DNA
<213> ORGANISM: Homo sapiens

<400> SEQUENCE: 23
ggcgctgcct acggaggtgg cagccatctc cttctcggca tc 42

<210> SEQ ID NO 24
<211> LENGTH: 186
<212> TYPE: DNA
<213> ORGANISM: Homo sapiens

<400> SEQUENCE: 24
catcacattt aaaagcatct cagcctacca tgagaataag agaaagaaaa tgaagatcaa 60
aagcttattc atctgttttt ctttttcgtt ggtgtaaagc caacaccctg tctaaaaaac 120
ataaatttct ttaatcattt tgcctctttt ctctgtgctt caattaataa aaaatggaaa 180
gaatct 186

<210> SEQ ID NO 25
<211> LENGTH: 186
<212> TYPE: DNA
<213> ORGANISM: Homo sapiens

<400> SEQUENCE: 25
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacct 186

<210> SEQ ID NO 26
<211> LENGTH: 110
<212> TYPE: DNA
<213> ORGANISM: Homo sapiens

<400> SEQUENCE: 26
gctggagcct cggtggccat gcttcttgcc ccttgggcct ccccccagcc cctcctcccc 60
ttcctgcacc cgtacccccg tggtctttga ataaagtctg agtgggcggc 110

<210> SEQ ID NO 27
<211> LENGTH: 108
<212> TYPE: DNA
<213> ORGANISM: Homo sapiens

<400> SEQUENCE: 27
gctggagcct cggtagccgt tcctcctgcc cgctgggcct cccaacgggc cctcctcccc 60
tccttgcacc ggcccttcct ggtctttgaa taaagtctga gtgggcag 108

<210> SEQ ID NO 28
<211> LENGTH: 132
<212> TYPE: DNA
<213> ORGANISM: Homo sapiens

<400> SEQUENCE: 28
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 29
<211> LENGTH: 44
<212> TYPE: DNA
<213> ORGANISM: Artificial Sequence
<220> FEATURE:
<223> OTHER INFORMATION: Center, alpha-complex-binding portion of the 3'UTR of an alpha-globin gene (muag)

<400> SEQUENCE: 29
gcccgatggg cctcccaacg ggccctcctc ccctccttgc accg 44

<210> SEQ ID NO 30
<211> LENGTH: 24
<212> TYPE: DNA
<213> ORGANISM: Artificial Sequence
<220> FEATURE:
<223> OTHER INFORMATION: particular preferred histone stem-loop sequence

<400> SEQUENCE: 30
caaaggctct tttcagagcc acca 24

<210> SEQ ID NO 31
<211> LENGTH: 1942
<212> TYPE: RNA
<213> ORGANISM: Artificial Sequence
<220> FEATURE:
<223> OTHER INFORMATION: RSV-F long (GC) R1691

<400> SEQUENCE: 31
gggagaaagc uuaccaugga gcugcccauc cucaaggcca acgccaucac caccauccug 60
gcggccguga cguucugcuu cgccagcucc cagaacauca ccgaggaguu cuaccagagc 120
accugcuccg ccgucagcaa gggcuaccug uccgcccucc ggaccgggug guacacgagc 180
gugaucacca ucgagcuguc caacaucaag gagaacaagu gcaacggcac cgacgcgaag 240
gugaagcuga ucaaccagga gcucgacaag uacaagaacg ccgucaccga gcugcagcug 300
cucaugcaga gcacgaccgc cgccaacaac cgcgcgcggc gcgagcugcc gcgguucaug 360
aacuacaccc ugaacaacac caagaagacg aacgugaccc ucuccaagaa gcgcaagcgg 420
cgcuuccugg gguuccugcu cggcgugggg agcgccaucg ccuccggcau cgccgucagc 480
aaggugcugc accuggaggg cgaggugaac aagaucaagu ccgcccuccu gagcaccaac 540
aaggcggucg ugucccugag caacggggug uccguccuca ccagcaaggu gcuggaccug 600
aagaacuaca ucgacaagca gcuccugccc aucgugaaca agcaguccug ccggaucagc 660
aacaucgaga cggucaucga guuccagcag aagaacaacc gccugcucga gaucacccgg 720
gaguucagcg ugaacgccgg cgugaccacc cccgucucca cguacaugcu gaccaacagc 780
gagcugcucu cccugaucaa cgacaugccc aucaccaacg accagaagaa gcugaugagc 840
aacaacgugc agaucgugcg ccagcagucc uacagcauca uguccaucau caaggaggag 900
guccucgccu acguggugca gcugccgcug uacgggguca ucgacacccc cugcuggaag 960
cuccacacga gcccccugug caccaccaac accaaggagg gcuccaacau cugccugacg 1020
cggaccgacc gcggguggua cugcgacaac gccggcagcg uguccuucuu cccccaggcc 1080
gagaccugca agguccagag caaccgggug uucugcgaca ccaugaacuc ccucacgcug 1140
ccgagcgagg ugaaccugug caacgucgac aucuucaacc ccaaguacga cugcaagauc 1200
augaccucca agaccgacgu gagcuccagc gugaucaccu cccucggcgc gaucgucagc 1260
ugcuacggga agacgaagug caccgccagc aacaagaacc gcggcaucau caagaccuuc 1320
uccaacgggu gcgacuacgu gagcaacaag ggcguggaca ccgucuccgu gggcaacacc 1380
cuguacuacg ugaacaagca ggaggggaag agccuguacg ucaagggcga gcccaucauc 1440
aacuucuacg acccccucgu guucccgucc gacgaguucg acgccagcau cucccaggug 1500
aacgagaaga ucaaccagag ccuggccuuc auccggaagu ccgacgagcu gcugcaccac 1560
gucaacgccg ggaagagcac gaccaacauc augaucacca ccaucaucau cgugaucauc 1620
gugauccucc ugucccugau cgcggucggc cuccugcugu acugcaaggc ccgcagcacg 1680
cccgugaccc ucuccaagga ccagcugagc gggaucaaca acaucgccuu cuccaacuga 1740
ggacuaguua uaagacugac uagcccgaug ggccucccaa cgggcccucc uccccuccuu 1800
gcaccgagau uaauaaaaaa aaaaaaaaaa aaaaaaaaaa aaaaaaaaaa aaaaaaaaaa 1860
aaaaaaaaaa aaaaaaaaug caucccccc cccccccccc cccccccccc ccccaaaggc 1920
ucuuuucaga gccaccagaa uu 1942

<210> SEQ ID NO 32
<211> LENGTH: 2107
<212> TYPE: RNA
<213> ORGANISM: Artificial Sequence
<220> FEATURE:
<223> OTHER INFORMATION: RSV-F long (GC) R2510

<400> SEQUENCE: 32
ggggcgcugc cuacggaggu ggcagccauc uccuucucgg caucaagcuu accauggagc 60
ugcccauccu caaggccaac gccaucacca ccauccuggc ggccgugacg uucugcuucg 120
ccagcuccca gaacaucacc gaggaguucu accagagcac cugcuccgcc gucagcaagg 180
gcuaccuguc cgcccuccgg accgggugu acacgagcgu gaucaccauc gagcugucca 240
acaucaagga gaacaagugc aacggcaccg acgcgaaggu gaagcugauc aaccaggagc 300
ucgacaagua caagaacgcc gucaccgagc ugcagcugcu caugcagagc acgaccgccg 360
ccaacaaccg cgcgcggcgc gagcugccgc gguucaugaa cuacacccug aacaacacca 420
agaagacgaa cgugacccuc uccaagaagc gcaagcggcg cuuccugggg uuccugcucg 480
gcguggggag cgccaucgcc uccggcaucg ccgucagcaa ggugcugcac cuggagggcg 540
aggugaacaa gaucaagucc gcccuccuga gcaccaacaa ggcggucgug ucccugagca 600 acggggugc cguccucacc agcaaggugc uggaccugaa gaacuacauc gacaagcagc 660
uccugcccau cgugaacaag caguccugcc ggaucagcaa caucgagacg gucaucgagu 720
uccagcagaa gaacaaccgc cugcucgaga ucacccggga guucagcgug aacgccggcg 780
ugaccacccc cgucuccacg uacaugcuga ccaacagcga gcugcucucc cugaucaacg 840
acaugcccau caccaacgac cagaagaagc ugaugagcaa caacgugcag aucgugcgcc 900
agcaguccua cagcaucaug uccaucauca aggaggaggu ccucgccuac guggugcagc 960
ugccgcugua cggggucauc gacacccccu gcuggaagcu ccacacgagc cccugugca 1020 ccaccaacac caaggagggc uccaacaucu gccugacgcg gaccgaccgc gggugguacu 1080
gcgacaacgc cggcagcgug uccuucuucc cccaggccga gaccugcaag guccagagca 1140
accggguguu cugcgacacc augaacuccc ucacgcugcc gagcgaggug aaccugugca 1200
acgucgacau cuucaacccc aaguacgacu gcaagaucau gaccuccaag accgacguga 1260
gcuccagcgu gaucaccucc cucggcgcga ucgucagcug cuacgggaag acgaagugca 1320
ccgccagcaa caagaaccgc ggcaucauca agaccuucuc caacgggugc gacuacguga 1380
gcaacaaggg cguggacacc gucuccgugg gcaacacccu guacuacgug aacaagcagg 1440
aggggaagag ccuguacguc aagggcgagc ccaucaucaa cuucuacgac cccucgugu 1500 ucccguccga cgaguucgac gccagcaucu cccaggugaa cgagaagauc aaccagagcc 1560
uggccuucau ccggaagucc gacgagcugc ugcaccacgu caacgccggg aagagcacga 1620
ccaacaucau gaucaccacc aucaucaucg ugaucaucgu gauccuccug ucccugaucg 1680
cggucggccu ccugcuguac ugcaaggccc gcagcacgcc cgugacccuc uccaaggacc 1740
agcugagcgg gaucaacaac aucgccuucu ccaacugagg acuagugcau cacauuuaaa 1800
agcaucucag ccuaccauga gaauaagaga aagaaaauga agaucaauag cuuauucauc 1860
ucuuuuucuu uuucguuggu guaaagccaa cacccugucu aaaaaacaua aauuucuuua 1920
aucauuuugc cucuuuucuc ugugcuucaa uuaauaaaaa auggaaagaa ccuagaucua 1980
aaaaaaaaaa aaaaaaaaaa aaaaaaaaaa aaaaaaaaaa aaaaaaaaaa aaaaaaaaaa 2040
aaaugcaucc cccccccccc cccccccccc cccccccccca aaggcucuuu ucagagccac 2100
cagaauu 2107

<210> SEQ ID NO 33
<211> LENGTH: 2044
<212> TYPE: RNA
<213> ORGANISM: Artificial Sequence
<220> FEATURE:
<223> OTHER INFORMATION: RSV-Fdel554-574 long (GC) R2821

<400> SEQUENCE: 33
ggggcgcugc cuacggaggu ggcagccauc uccuucucgg caucaagcuu accauggagc 60
ugcccauccu caaggccaac gccaucacca ccauccuggc ggccgugacg uucugcuucg 120
ccagcuccca gaacaucacc gaggaguucu accagagcac cugcuccgcc gucagcaagg 180
gcuaccuguc cgcccuccgg accgggguggu acacgagcgu gaucaccauc gagcugucca 240
acaucaagga gaacaagugc aacggcaccg acgcgaaggu gaagcugauc aaccaggagc 300
ucgacaagua caagaacgcc gucaccgagc ugcagcugcu caugcagagc acgaccgccg 360
ccaacaaccg cgcgcggcgc gagcugccgc gguucaugaa cuacacccug aacaacacca 420
agaagacgaa cgugacccuc uccaagaagc gcaagcggcg cuuccugggg uuccugcucg 480
gcguggggag cgccaucgcc uccggcaucg ccgucagcaa ggugcugcac cuggagggcg 540
aggugaacaa gaucaagucc gcccuccuga gcaccaacaa ggcggucgug ucccugagca 600 acggggguguc cguccucacc agcaaggugc uggaccugaa gaacuacauc gacaagcagc 660
uccugcccau cgugaacaag caguccugcc ggaucagcaa caucgagacg gucaucgagu 720
uccagcagaa gaacaaccgc cugcucgaga ucacccggga guucagcgug aacgccggcg 780
ugaccacccc cgucuccacg uacaugcuga ccaacagcga gcugcucucc cugaucaacg 840
acaugcccau caccaacgac cagaagaagc ugaugagcaa caacgugcag aucgugcgcc 900
agcaguccua cagcaucaug uccaucauca aggaggaggu ccucgccuac gugguggcagc 960 ugccgcugua cggggucauc gacacccccu gcuggaagcu ccacacgagc cccugugca 1020 ccaccaacac caaggagggc uccaacaucu gccugacgcg gaccgaccgc gggugguacu 1080
gcgacaacgc cggcagcgug uccuucuucc cccaggccga gaccugcaag guccagagca 1140 accgggugu cugcgacacc augaacuccc ucacgcugcc gagcgaggug aaccugugca 1200
acgucgacau cuucaacccc aaguacgacu gcaagaucau gaccuccaag accgacguga 1260
gcuccagcgu gaucaccucc cucggcgcga ucgucagcug cuacgggaag acgaagugca 1320
ccgccagcaa caagaaccgc ggcaucauca agaccuucuc caacgggugc gacuacguga 1380
gcaacaaggg cguggacacc gucuccgugg gcaacacccu guacuacgug aacaagcagg 1440
aggggaagag ccuguacguc aagggcgagc ccaucaucaa cuucuacgac cccucgugu 1500 ucccguccga cgaguucgac gccagcaucu cccaggugaa cgagaagauc aaccagagcc 1560
uggccuucau ccggaagucc gacgagcugc ugcaccacgu caacgccggg aagagcacga 1620
ccaacaucau gaucaccacc aucaucaucg ugaucaucgu gauccuccug ucccugaucg 1680
cggucggccu ccugcuguac ugcaaggccc gcugaggacu agugcaucac auuuaaaagc 1740
aucucagccu accaugagaa uaagagaaag aaaaugaaga ucaauagcuu auucaucucu 1800
uuuucuuuuu cguuggugua aagccaacac ccugucuaaa aaacauaaau uucuuuaauc 1860
auuuugccuc uuuucucugu gcuucaauua auaaaaaaug gaaagaaccu agaucuaaaa 1920
aaaaaaaaaa aaaaaaaaaa aaaaaaaaaa aaaaaaaaaa aaaaaaaaaa aaaaaaaaaa 1980 ugcaucccc cccccccccc cccccccccc ccccccaaag gcucuuuuca gagccaccag 2040
aauu 2044

<210> SEQ ID NO 34
<211> LENGTH: 1558
<212> TYPE: RNA
<213> ORGANISM: Artificial Sequence
<220> FEATURE:
<223> OTHER INFORMATION: RSV-N (GC) R2831

<400> SEQUENCE: 34
ggggcgcugc cuacggaggu ggcagccauc uccuucucgg caucaagcuu accauggccc 60
ugagcaaggu gaagcucaac gacacccuga acaaggacca gcugcucucc agcuccaagu 120
acaccaucca gcgcagcacg ggcgacucca ucgacacccc caacuacgac guccagaagc 180
acaucaacaa gcugugcggg augcugcuca ucaccgagga cgccaaccac aaguucaccg 240
gccugaucgg gaugcuguac gcgaugagcc ggcucggccg cgaggacacg aucaagaucc 300
ugcgggacgc cggguaccac gugaaggcca acggcgugga cgucaccacc caccgccagg 360
acaucaacgg caaggagaug aaguucgagg ugcugacccu cgccucccug acgaccgaga 420
uccagaucaa caucgagauc gagagccgga aguccuacaa gaagaugcug aaggagaugg 480
gggagguggc cccggaguac cgccacgaca gccccgacug cggcaugauc auccucugca 540
ucgcggcccu ggucaucacc aagcuggccg ccggggaccg guccggccuc accgcgguga 600
uccgccgggc caacaacgug cugaagaacg agaugaagcg cuacaagggg cugcuccca 660 aggacaucgc caacagcuuc uacgaggucu ucgagaagca cccccacuuc aucgacgugu 720

-continued ucgugcacuu cggcaucgcc caguccagca cgcggggcgg gucccgcguc gagggcaucu 780
ucgccgggcu guucaugaac gcguacggcg ccggccaggu gaugcugcgg uggggcgugc 840
ucgccaagag cgucaagaac aucaugcugg ggcacgccuc cgugcaggcc gagauggagc 900
agguggucga gguguacgag uacgcgcaga agcugggcgg cgaggccggg uucuaccaca 960
uccucaacaa cccgaaggcc agccugcugu cccucaccca guucccgcac uucagcagcg 1020
ugguccuggg gaacgccgcc ggccugggga ucaugggcga guaccgcggg accccgcgga 1080
accaggaccu cuacgacgcg gccaaggccu acgccgagca gcugaaggag aacggcguga 1140
ucaacuacuc cgugcuggac cucaccgccg aggagcugga ggcgaucaag caccagcuga 1200
accccaagga caacgacguc gagcucugag gacuagugca ucacauuuaa aagcaucuca 1260
gccuaccaug agaauaagag aaagaaaaug aagaucaaua gcuuauucau cucuuuuucu 1320
uuuucguugg uguaaagcca acacccuguc uaaaaaacau aaauuucuuu aaucauuuug 1380
ccucuuuucu cugugcuuca auuaauaaaa aauggaaaga accuagaucu aaaaaaaaaa 1440
aaaaaaaaaa aaaaaaaaaa aaaaaaaaaa aaaaaaaaaa aaaaaaaaaa aaaaugcauc 1500
cccccccccc cccccccccc cccccccccc aaaggcucuu uucagagcca ccagaauu 1558

<210> SEQ ID NO 35
<211> LENGTH: 967
<212> TYPE: RNA
<213> ORGANISM: Artificial Sequence
<220> FEATURE:
<223> OTHER INFORMATION: RSV-M2-1 (GC) R2833

<400> SEQUENCE: 35
ggggcgcugc cuacggaggu ggcagccauc uccuucucgg caucaagcuu accaugagcc 60
gccggaaccc cugcaaguuc gagauccgcg gccacugccu gaacgggaag cggugccacu 120
ucucccacaa cuacuucgag uggccgcccc acgcccuccu ggugcgccag aacuucaugc 180
ugaaccggau ccucaagagc auggacaagu ccaucgacac ccugagcgag aucuccggcg 240
ccgcggagcu ggaccgcacc gaggaguacg cccucggggu cgugggcgug cuggagagcu 300 acaucgggguc caucaacaac aucacgaagc agagcgccug cgucgccaug uccaagcugc 360
ucaccgagcu gaacagcgac gacaucaaga agcugcggga caacgaggag cucaacuccc 420
ccaagauccg cguguacaac accgugauca gcuacaucga guccaaccgg aagaacaaca 480
agcagaccau ccaccugcug aagcgccucc ccgccgacgu ccugaagaag acgaucaaga 540
acacccugga cauccacaag agcaucacca ucaacaaccc gaaggagcuc accgugucgg 600
acacgaacga ccacgcgaag aacaacgaca ccaccugagg acuagugcau cacauuuaaa 660
agcaucucag ccuaccauga gaauaagaga aagaaaauga agaucaauag cuuauucauc 720
ucuuuuucuu uuucguuggu guaaagccaa cacccugucu aaaaaacaua aauuucuuua 780
aucauuuugc cucuuuucuc ugugcuucaa uuaauaaaaa auggaaagaa ccuagaucua 840
aaaaaaaaaa aaaaaaaaaa aaaaaaaaaa aaaaaaaaaa aaaaaaaaaa aaaaaaaaaa 900
aaaugcaucc cccccccccc cccccccccc cccccccccca aaggcucuuu ucagagccac 960
cagaauu 967

<210> SEQ ID NO 36
<211> LENGTH: 75
<212> TYPE: DNA
<213> ORGANISM: Homo sapiens

<400> SEQUENCE: 36

-continued

```
gcggctcggc cattttgtcc cagtcagtcc ggaggctgcg gctgcagaag taccgcctgc      60

ggagtaactg caaag                                                       75


<210> SEQ ID NO 37
<211> LENGTH: 24
<212> TYPE: RNA
<213> ORGANISM: Artificial Sequence
<220> FEATURE:
<223> OTHER INFORMATION: histone stem-loop sequence

<400> SEQUENCE: 37

caaaggcucu uuucagagcc acca                                             24
```